US010736608B2

(12) United States Patent
Matsumoto

(10) Patent No.: US 10,736,608 B2
(45) Date of Patent: Aug. 11, 2020

(54) ULTRASOUND DIAGNOSTIC DEVICE AND ULTRASOUND IMAGE PROCESSING METHOD

(71) Applicant: KONICA MINOLTA, INC, Chiyoda-ku (JP)

(72) Inventor: Yuki Matsumoto, Hirakata (JP)

(73) Assignee: Konica Minolta, Inc., Tokyo (JP)

( * ) Notice: Subject to any disclaimer, the term of this patent is extended or adjusted under 35 U.S.C. 154(b) by 681 days.

(21) Appl. No.: 15/467,825

(22) Filed: Mar. 23, 2017

(65) Prior Publication Data

US 2017/0273668 A1   Sep. 28, 2017

(30) Foreign Application Priority Data

Mar. 23, 2016  (JP) .................. 2016-059015

(51) Int. Cl.
*A61B 8/00* (2006.01)
*A61B 8/08* (2006.01)
*A61B 8/14* (2006.01)

(52) U.S. Cl.
CPC .......... *A61B 8/5223* (2013.01); *A61B 8/0875* (2013.01); *A61B 8/145* (2013.01); *A61B 8/463* (2013.01); *A61B 8/5292* (2013.01); *A61B 8/54* (2013.01)

(58) Field of Classification Search
CPC ....... A61B 8/5223; A61B 8/54; A61B 8/5292; A61B 8/463; A61B 8/145; A61B 8/0875
See application file for complete search history.

(56) References Cited

U.S. PATENT DOCUMENTS 8,777,854 B2 * 7/2014 Patwardhan ......... G06K 9/3241
600/407

FOREIGN PATENT DOCUMENTS

JP       2013-056156        3/2013

* cited by examiner

*Primary Examiner* — Joel Lamprecht
(74) *Attorney, Agent, or Firm* — Cozen O'Connor

(57) ABSTRACT

An ultrasound diagnostic device including an ultrasound image acquirer that acquires a plurality of ultrasound image signal frames; an angle information acquirer that acquires angle information of an ultrasound probe when each frame is being acquired; an evaluation determiner that analyzes the frames to determine whether an object image portion is included; a disease score calculator that calculates a disease score that quantitatively indicates a degree of disease from a signal of the object image portion; and a display controller that makes the diagnostic image be displayed. A diagnostic image includes an ultrasound image of a frame selected from the frames, a disease activity information indicator that indicates a degree of disease, and an angle information image portion that indicates angle information.

23 Claims, 40 Drawing Sheets

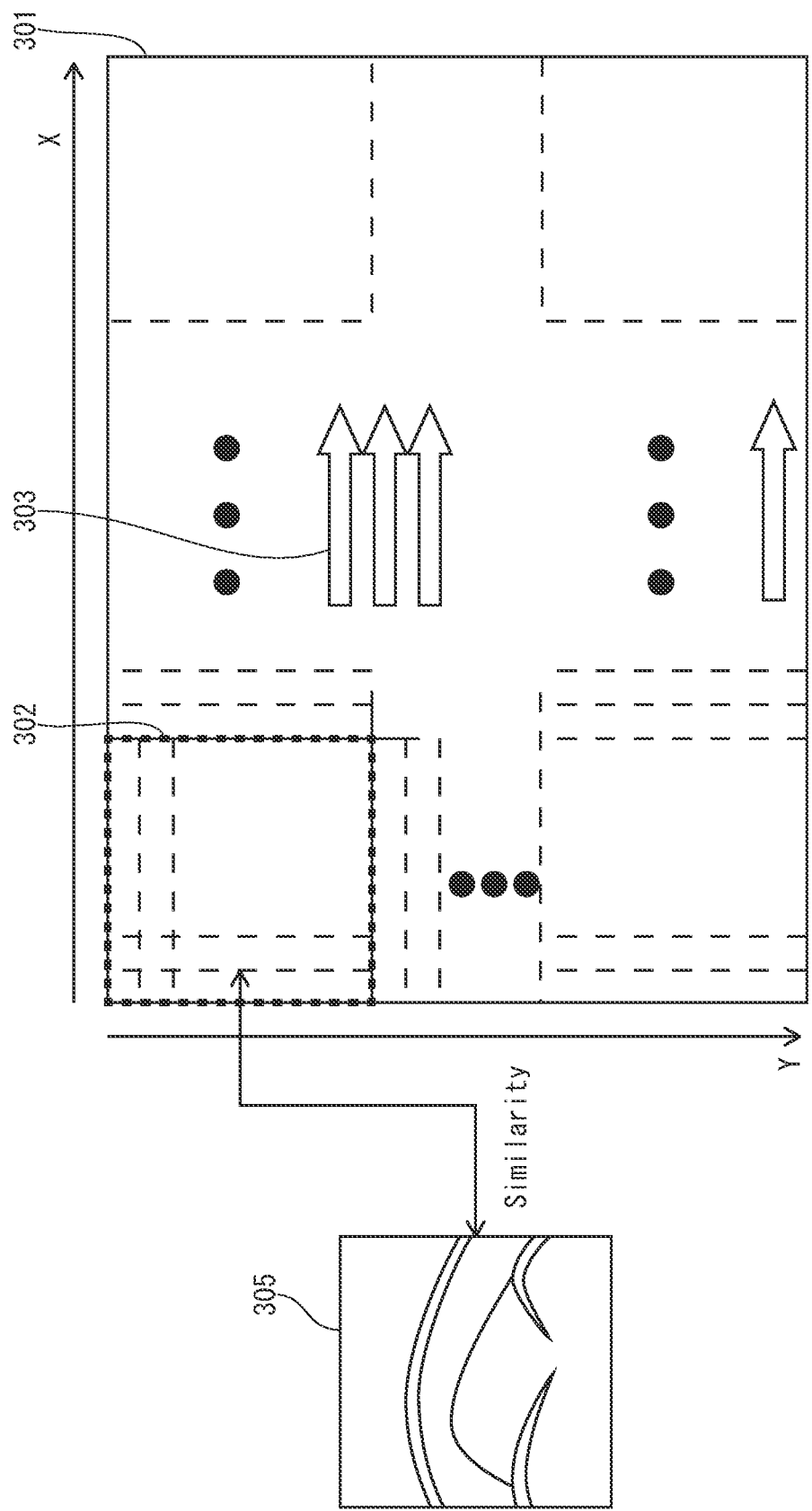

ULTRASOUND DIAGNOSTIC DEVICE AND ULTRASOUND IMAGE PROCESSING METHOD

This application is based on application No. 2016-059015 filed in Japan, the contents of which are hereby incorporated by reference.

TECHNICAL BACKGROUND (1) Technical Field

The present disclosure belongs to the technical field of ultrasound image processing, and in particular relates to ultrasound image processing methods for quantifying extent of rheumatism for diagnostic purposes and ultrasound diagnostic devices using same.

(2) Description of Related Art

Recently it is becoming common to use ultrasound diagnostic devices to evaluate disease activity of arthritis, including rheumatoid arthritis (for example, JP 2013-056156). Primarily B-mode images and power Doppler images are used in disease activity evaluation; synovial thickening, synovial fluid retention, and bone erosion being observable in B-mode images, and synovial inflammation being observable in power Doppler images.

SUMMARY OF THE INVENTION

Problems to be Solved by the Invention

In ultrasound image diagnosis, different evaluation results can be obtained depending on the cross-section of a subject from which an ultrasound image is acquired for evaluation. Thus, when performing ultrasound image diagnosis, there are cases in which it is necessary to select from a plurality of ultrasound images a cross-section image from which disease activity can be appropriately evaluated. Thus, there is demand for an ultrasound diagnostic device capable of easily searching for an appropriate cross-section image when there is a plurality of ultrasound images.

The present disclosure aims to solve the problems described above, and aims to provide an ultrasound diagnostic device capable of easily searching for a desired cross-section image when an operator selects a cross-section image that appropriately indicates a degree of disease (disease activity).

Means for Solving the Problems

To achieve the above aims, the ultrasound diagnostic device pertaining to one aspect of the present invention is an ultrasound diagnostic device for generating a diagnostic image based on a plurality of ultrasound image signal frames acquired from a subject via an ultrasound probe, the ultrasound diagnostic device comprising: an ultrasound signal processing circuit, the ultrasound signal processing circuit comprising: an ultrasound image acquirer that acquires the plurality of ultrasound image signal frames; an angle information acquirer that acquires angle information of an angle of the ultrasound probe relative to the subject when each frame of the plurality of ultrasound image signal frames is being acquired; an evaluation determiner that analyzes the plurality of ultrasound image signal frames, and, when an object image portion that satisfies a predefined condition is included in a frame, determines that the frame is an evaluation object frame; a disease score calculator that calculates a disease score that quantitatively indicates a degree of disease from a signal of the object image portion in the evaluation object frame; and a display controller that generates the diagnostic image and makes the diagnostic image be displayed on a display, wherein the diagnostic image includes an ultrasound image of a frame selected from the plurality of ultrasound image signal frames, a disease activity information indicator that indicates a degree of disease in the selected frame, and an angle information image portion that indicates angle information corresponding to the selected frame.

BRIEF DESCRIPTION OF THE DRAWINGS

These and the other aims, advantages and features of the invention will become apparent from the following description thereof taken in conjunction with the accompanying drawings which illustrate a specific embodiment of the invention. In the drawings:

FIG. 10 is a schematic diagram for describing operation of joint search processing;

DESCRIPTION OF EMBODIMENT

Embodiment

<Configuration>

The following describes, pertaining to the embodiment, an ultrasound diagnostic device 1100, an ultrasound image processing method, and an ultrasound diagnostic system 1000 including the ultrasound diagnostic device 1100, with reference to the drawings.

<1. Overall Configuration of Ultrasound Diagnostic System 1000>

Figure 1:
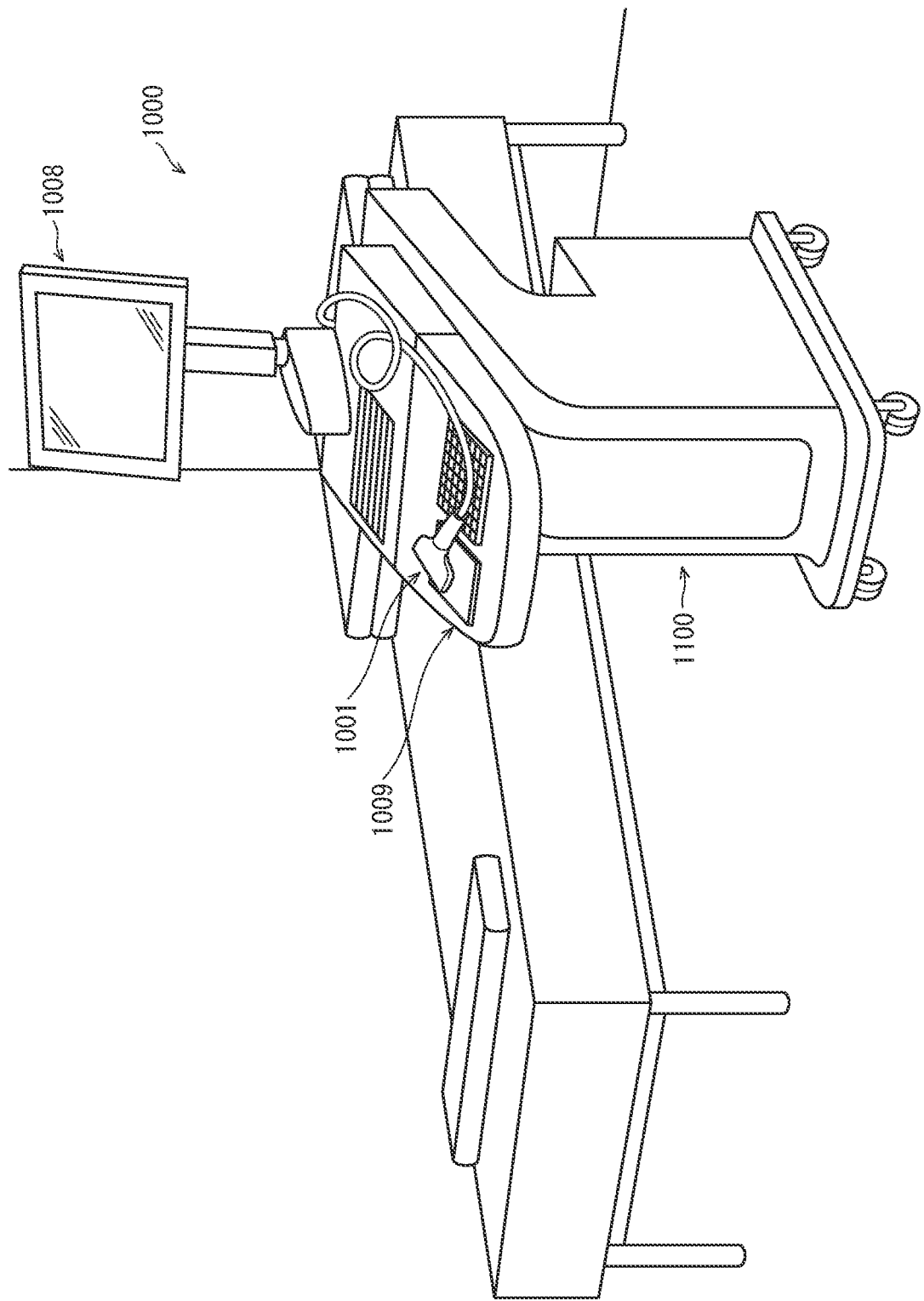
FIG. 1 is a perspective view of an ultrasound diagnostic system including an ultrasound diagnostic device pertaining to an embodiment.
Figure 2:
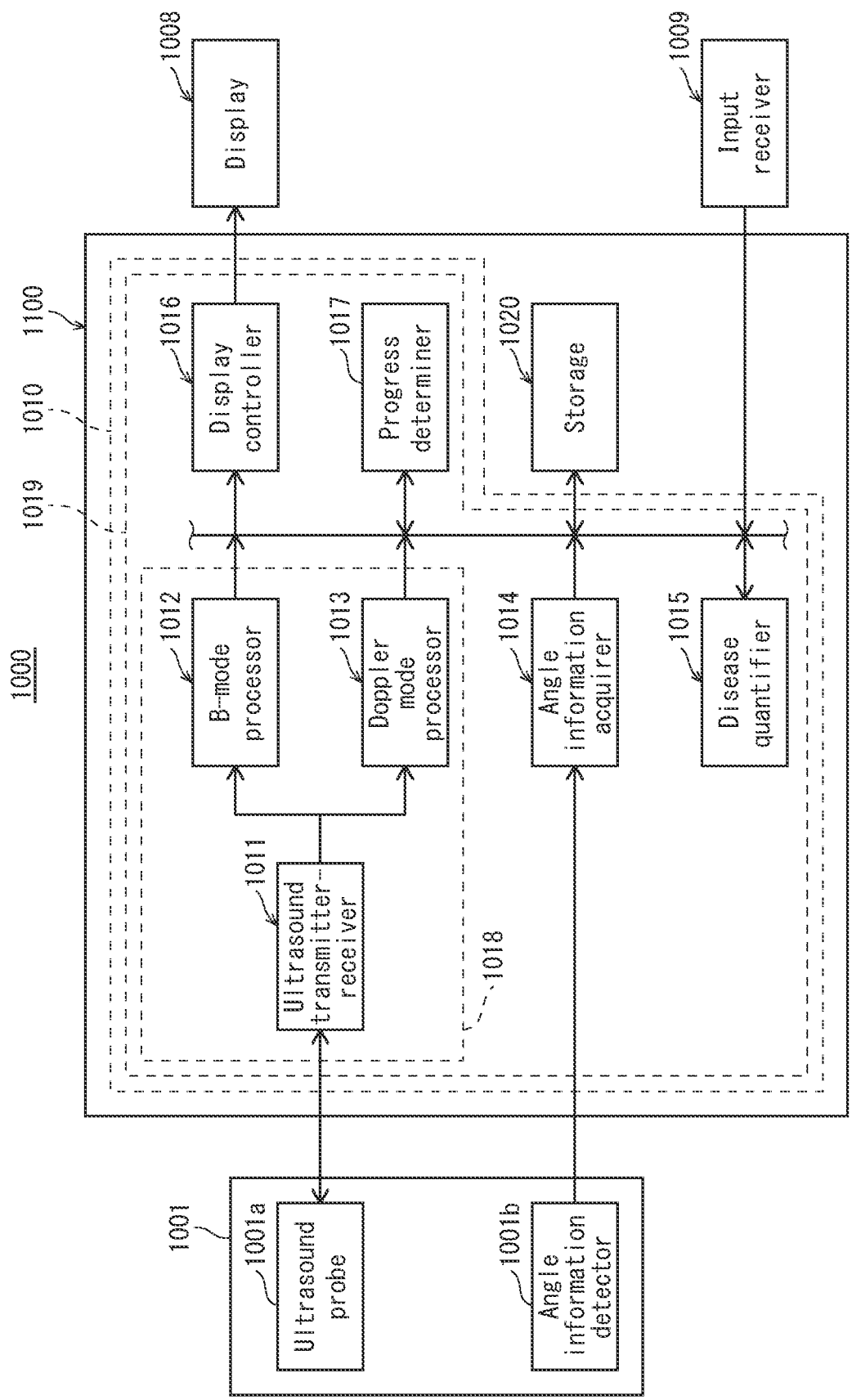
FIG. 2 is a block diagram showing a configuration of an ultrasound diagnostic device pertaining to the embodiment.

The following describes a schematic configuration of the ultrasound diagnostic device 1100 pertaining to the embodiment. FIG. 1 is a perspective view of the ultrasound diagnostic system 1000 including the ultrasound diagnostic device 1100. FIG. 2 is a function block diagram of the ultrasound diagnostic system 1000.

The ultrasound diagnostic system 1000 includes the ultrasound diagnostic device 1100, a probe unit 1001, a display 1008, and an input receiver 1009. The following describes the components of the ultrasound diagnostic system 1000.

(1-1) Probe Unit 1001

The probe unit 1001 includes an ultrasound probe 1001a and an angle information detector 1001b.

The ultrasound probe 1001a transmits transmission ultrasound generated by an ultrasound transmitter-receiver 1011 into a subject and receives reflected ultrasound that is reflected in the subject. Reflected ultrasound received by the ultrasound probe 1001a is outputted as an echo signal to the ultrasound transmitter-receiver 1011.

The ultrasound probe 1001a has, for example, a transducer array consisting of a plurality of piezoelectric elements (not illustrated) arranged in a one-dimensional direction (hereinafter, "transducer array direction"), and converts a pulsed electric signal supplied from the ultrasound transmitter-receiver 1011 (hereinafter, "transmit ultrasound signal") into pulsed ultrasound. At such time, while piezoelectric element outer surfaces are in contact with a skin surface of a subject, the ultrasound probe 1001a transmits an ultrasound beam composed from ultrasound emitted from a plurality of transducers towards a measurement object. Subsequently, the ultrasound probe 1001a receives reflected ultrasound from the subject, converts the reflected ultrasound into electric signals (hereinafter, "reception ultrasound signals") via a plurality of transducers, and outputs the reception ultrasound signals to the ultrasound transmitter-receiver 1011.

According to such ultrasound scanning via the ultrasound probe 1001a, in which an ultrasound beam is transmitted towards a predefined region (diagnostic site) of a subject facing the transducer array and reflected ultrasound reflected in the subject is received, an ultrasound image can be acquired in a cross-section taken along the transducer array direction and a depth direction perpendicular to the transducer array direction. A unit of an ultrasound image acquired by one ultrasound scan is defined as a frame and is expressed as a unit of a single combined signal necessary to construct one cross-section image. By repeating such an ultrasound scan, a plurality of frames of ultrasound images can be acquired.

The angle information detector 1001b detects angle information of the ultrasound probe 1001a relative to the subject and transmits same to an angle information acquirer 1014. According to the present embodiment, the angle information detector 1001b is integrated with the ultrasound probe 1001a as the probe unit 1001. More specifically, an angle sensor, an angular velocity sensor (gyro sensor), or the like can be used as the angle information detector 1001b.

Note that herein, angle information relative to the subject means angle of a transmission direction of an ultrasound beam from the ultrasound probe 1001a relative to the horizontal.

(1-2) Display 1008

The display 1008 is an image display device that displays image output from a display controller, described later, to a display screen. A liquid crystal display, CRT, organic EL display or the like can be used as the display 1008.

(1-3) Input Receiver 1009

The input receiver 1009 is an input device that receives various types of operation input from an operator such as settings and operations with respect to the ultrasound diagnostic device 1100, and outputs same to a controller 1010. Information inputted by an operator may include patient name, examination date, screen playback/stop commands, image quality adjustment, etc. Such input information is stored in a storage 1020.

More specifically, the input receiver 1009 corresponds to, for example, a keyboard, a mouse, a trackball, a touch panel, or the like. In the case of a touch panel, the input receiver 1009 may be integrated with the display 1008. In such a case, various settings and operations of the ultrasound diagnostic device 1100 can be performed by touch and drag operations on operation keys displayed on the display 1008, and the ultrasound diagnostic device 1100 is configured to be operable by the touch panel.

Further, the input receiver 1009 may be an operation panel that has a keyboard with various specialized keys, various specialized buttons, levers, etc. Further, the input receiver 1009 may be a trackball, mouse, etc., for moving a cursor displayed on the display 1008. Further, the input receiver 1009 may use a combination of any of the above.

(1-4) Ultrasound Diagnostic Device 1100

The ultrasound diagnostic device 1100 performs ultrasound signal transmission and reception for ultrasound diagnosis via the ultrasound probe 1001a and performs imaging of reflected ultrasound signals received. The following describes configuration of the ultrasound diagnostic device 1100. FIG. 2 is a function block diagram showing configuration of the ultrasound diagnostic device 1100, which shows the ultrasound diagnostic device 1100 connected to the probe unit 1001, the display 1008, and the input receiver 1009.

As shown in FIG. 2, the ultrasound diagnostic device 1100 includes the controller 1010 and the storage 1020, which are connected to each other.

The controller 1010 includes the ultrasound transmitter-receiver 1011, a B-mode processor 1012, a Doppler mode processor 1013, the angle information acquirer 1014, a disease quantifier 1015, a display controller 1016, and a progress determiner 1017. Of these, the ultrasound transmitter-receiver 1011, the B-mode processor 1012, and the Doppler mode processor 1013 constitute the ultrasound image acquirer 1018. The ultrasound image acquirer 1018, the angle information acquirer 1014, the disease quantifier 1015, the display controller 1016, and the progress determiner 1017 constitute ultrasound signal processing circuitry 1019. Among components of the disease quantifier 1015, only an evaluation determiner 2002 (see FIG. 3) and a disease score calculator 2003 (see FIG. 3) may be included in the ultrasound signal processing circuitry 1019. The ultrasound transmitter-receiver 1011, the B-mode processor 1012, the Doppler mode processor 1013, the angle information acquirer 1014, the disease quantifier 1015, the display controller 1016, and the progress determiner 1017 are each implemented by hardware such as a field programmable gate array (FPGA) or application specific integrated circuit (ASIC). Alternatively, these elements may be implemented by software and a programmable device such as a central processing unit (CPU), a graphics processing unit (GPU), or a processor. Each of these elements can be implemented as one circuit, or an aggregate of a plurality of circuits. Further, a plurality of these elements can be combined into a single circuit or an aggregate of a plurality of circuits.

The ultrasound transmitter-receiver 1011 is connectable to the ultrasound probe 1001a, the angle information acquirer 1014 is connectable to the angle information detector 1001b, and the display controller 1016 is connectable to the display 1008. Further, the controller 1010 is connectable to the input receiver 1009, which receives input from an operator.

The above describes the components of the ultrasound diagnostic system 1000.

<2. Components of Ultrasound Diagnostic Device 1100>

The following describes each element included in the ultrasound diagnostic device 1100.

(2-1) Ultrasound Transmitter-Receiver 1011

The ultrasound transmitter-receiver 1011 is connected to the ultrasound probe 1001a. The ultrasound transmitter-receiver 1011 performs transmission processing supplying a pulsed transmit ultrasound signal to make the ultrasound probe 1001a transmit an ultrasound beam. More specifically, the ultrasound transmitter-receiver 1011 is provided with a clock generation circuit, a pulse generation circuit, and a delay circuit. The clock generation circuit is a circuit that generates a clock signal that determines transmission timing of an ultrasound beam. The pulse generation circuit is a circuit for generating a pulse signal that drives each transducer. The delay circuit sets a delay for transmission timing of an ultrasound beam for each transducer, delaying transmission of the ultrasound beam for focusing and steering of the ultrasound beam.

Further, the ultrasound transmitter-receiver 1011 performs beamforming for ultrasound scanning based on an echo signal inputted from the ultrasound probe 1001a, and performs reception processing on acoustic line signals outputted to the B-mode processor 1012 and the Doppler mode processor 1013.

In beamforming, after amplifying a reception ultrasound signal acquired from the ultrasound probe 1001a, an analog-to-digital (A/D) converted radio frequency (RF) signal is subjected to delay-and-sum to generate an acoustic line signal that is continuous in a depth direction. Herein, an RF signal is, for example, composed of a plurality of signals in a direction perpendicular to the transducer array direction, which is an ultrasound transmission direction, each signal being an electrical signal converted from amplitude of reflected ultrasound, A/D converted to a digital signal. An acoustic line signal is continuous data in a depth direction made from RF signals after delay-and-sum processing.

The ultrasound transmitter-receiver 1011 repeatedly and continuously performs transmission processing and reception processing.

(2-2) B-Mode Processor 1012

The B-mode processor 1012 generates a B-mode image signal based on an acoustic line signal inputted by the ultrasound transmitter-receiver 1011. A generated B-mode image signal is stored in the storage 1020.

More specifically, the B-mode processor 1012 generates a B-mode image signal by carrying out processing such as envelope detection and logarithmic compression on an acoustic line signal, converting it to a brightness signal corresponding to intensity, and subjects the brightness signal to coordinate transformation to an orthogonal coordinate system. The B-mode processor sequentially performs this processing for each frame, and a generated frame B-mode image signal is outputted to the storage 1020 each time ultrasound scanning is performed. Further, as described later, a B-mode image signal is supplied to the image controller 1016 and displayed on the display 1008.

(2-3) Doppler Mode Processor 1013

The Doppler mode processor 1013 subjects an acoustic line signal inputted from the ultrasound transmitter-receiver 1011 to an autocorrelation operation to extract a Doppler component that is source data of a Doppler signal that indicates change over time of blood flow in a living body. Then the Doppler mode processor 1013 generates a Doppler mode image signal that expresses intensity of blood flow information such as average velocity, dispersion, power, etc., in color.

More specifically, the Doppler mode processor 1013 performs an autocorrelation operation on an acoustic line signal, converts it into flow velocity, then extracts, via filtering, a velocity component indicating a blood flow component. The Doppler mode processor 1013 then calculates dispersion and power of average velocity of the blood flow component and generates a Doppler mode image signal. A generated Doppler mode image signal is outputted to the storage 1020 each time ultrasound scanning is performed. Further, as described later, a Doppler mode image signal is supplied to the display controller 1016 and displayed on the display 1008.

(2-4) Angle Information Acquirer 1014

The angle information acquirer 1014 is connected to the angle information detector 1001b. The angle information acquirer 1014 is a circuit for acquiring from the angle information detector 1001b angle information of the ultrasound probe 1001a relative to the subject, and causing angle information to be stored in the storage 1020.

(2-5) Disease Quantifier 1015

The disease quantifier 1015 analyzes a B-mode image signal and a Doppler mode image signal stored in the storage 1020, to quantify a degree of rheumatism. A method of quantification is described later. A result of quantification is stored in the storage 1020 for each ultrasound image signal frame.

(2-6) Display Controller 1016

The display controller 1016 creates an ultrasound image based on a B-mode image signal and a Doppler mode image signal stored in the storage 1020. Then the display controller 1016 overlays onto the ultrasound image information such as examiner name, patient name, time, ultrasound diagnostic device settings, score calculated by the disease quantifier 1015, and angle to generate a diagnostic image, and causes the diagnostic image to be displayed on the display 1008 that is externally connected. Note that the ultrasound diagnostic device 1100 may be configured as required to include a part or all of the probe unit 1001, the input receiver 1009, and the display 1008.

(2-7) Progress Determiner 1017

The progress determiner 1017 determines whether a disease is improving, maintaining, or worsening in comparison to a previous measurement, based on a result of quantification of a degree of rheumatism from the previous measurement stored in the storage 1020.

(2-8) Storage 1020

The storage 1020 is a storage device that stores B-mode image signals and Doppler mode image signals acquired for each frame. Each time ultrasound scanning is performed, B-mode image signals and Doppler mode image signals are inputted to the storage 1020 and stored. Further, the storage 1020 stores a disease score calculated by the disease quantifier 1015 (a numerical value quantifying a degree of disease; according the present embodiment, disease score means a swelling score and an inflammation score, which are described in detail later).

The storage 1020 is configured from RAM including dynamic random access memory (DRAM), static random access memory (SRAM), and the like, using semiconductor memory. Further, the storage 1020 may be implemented by a hard disk drive, optical disk drive, magnetic storage device, or the like, or may be configured from a combination of RAM and one or more of these. According to the present disclosure, an ultrasound image signal comprises a B-mode image signal and a Doppler mode image signal.

<3. Detailed Configuration of Disease Quantifier 1015>

Figure 3:
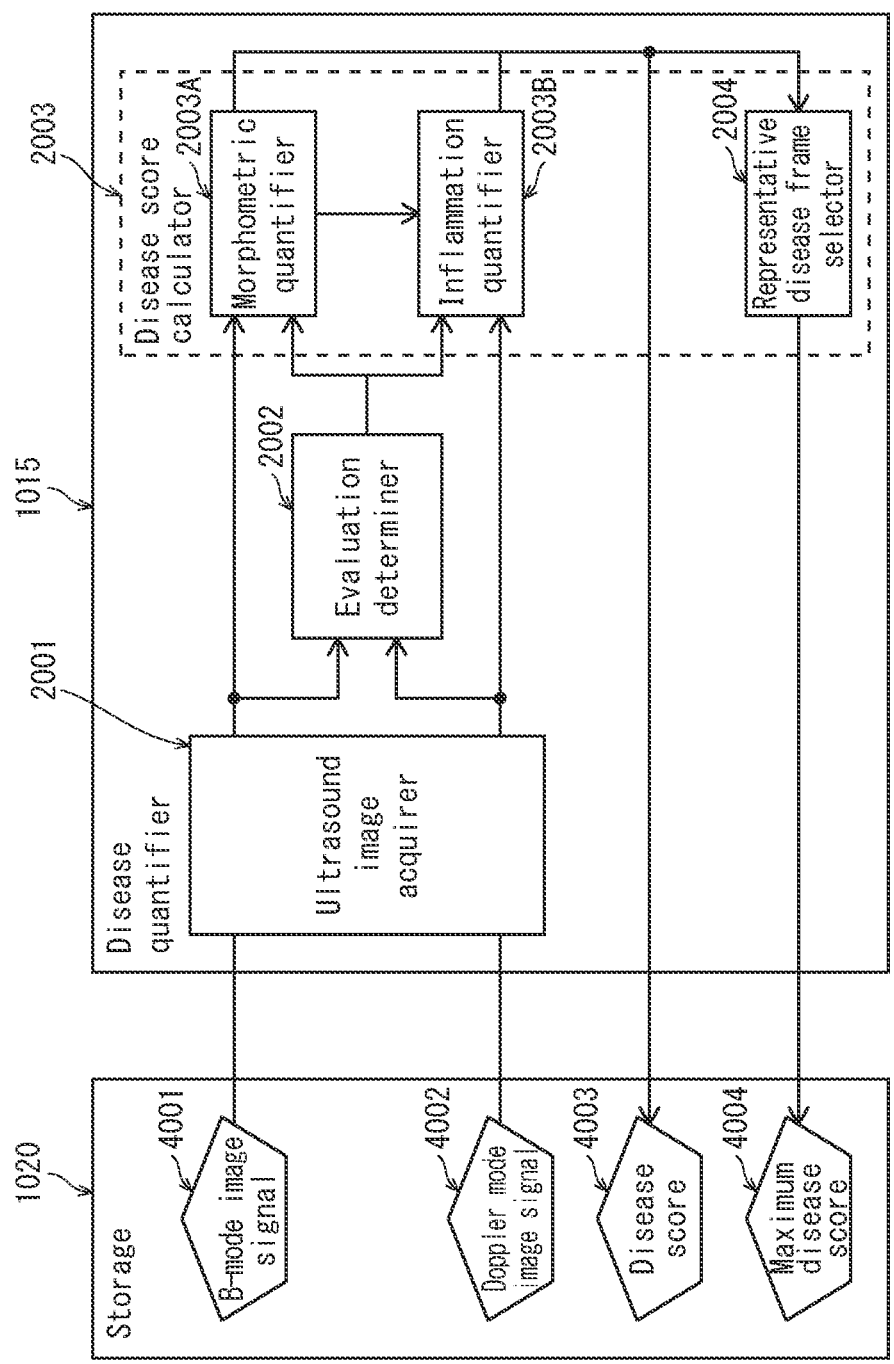
FIG. 3 is a block diagram showing a configuration of a disease quantifier.

The following describes configuration of the disease quantifier 1015 in detail, with reference to the drawings. FIG. 3 is a block diagram of the disease quantifier 1015.

The disease quantifier 1015 includes an ultrasound image acquirer 2001, the evaluation determiner 2002, the disease score calculator 2003, and a representative disease frame selector 2004. The disease score calculator 2003 includes a morphometric quantifier 2003A and an inflammation quantifier 2003B. The disease score calculator 1015 uses a B-mode image signal 4001 and a Doppler mode image signal 4002 stored in the storage 1020 as input, and outputs to the storage 1020 a disease score 4003 that indicates a degree of disease and a maximum disease score 4004 that is, for example, a maximum value of the disease score 4003.

(3-1) Ultrasound Image Acquirer 2001

The ultrasound image acquirer 2001 reads a B-mode image signal 4001 and a Doppler mode image signal 4002 for each frame from B-mode image signals 4001 and Doppler mode image signals 4002 of a plurality of frames stored in the storage 1020.

(3-2) Evaluation Determiner 2002

The evaluation determiner 2002 uses the B-mode image signal 4001 and the Doppler mode image signal 4002 outputted from the ultrasound image acquirer 2001 as input, determines whether or not an operator acquires an ultrasound image according to proper procedure, and outputs a result of this determination to the morphometric quantifier 2003A and the inflammation quantifier 2003B.

Figure 4:
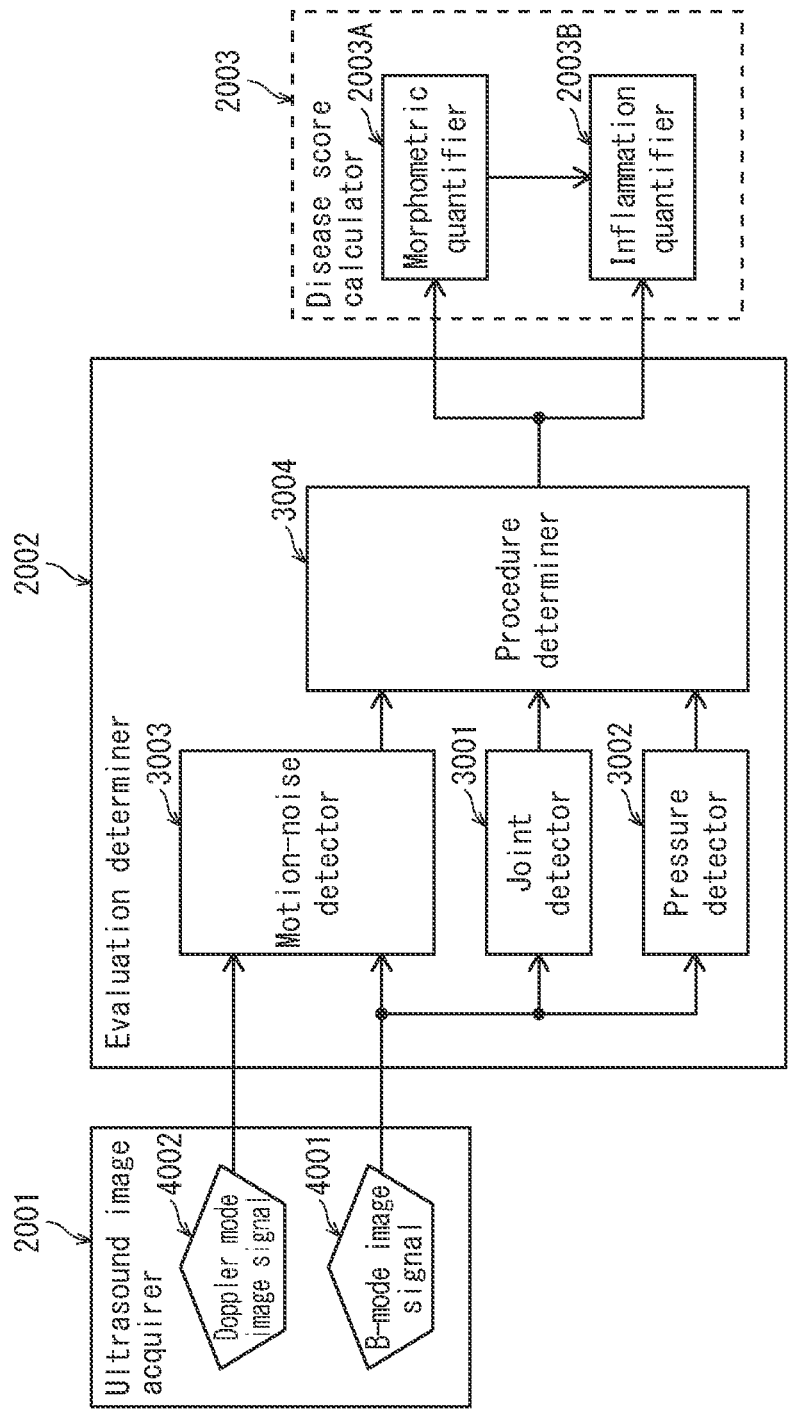
FIG. 4 is a block diagram showing a configuration of an evaluation determiner.

The following describes configuration of the evaluation determiner 2002 in detail, with reference to the drawings. FIG. 4 is a block diagram of the evaluation determiner 2002. As shown in FIG. 4, the evaluation determiner 2002 includes a joint detector 3001, a compression detector 3002, a motion-noise detector 3003, and a procedure determiner 3004.

i) Joint Detector 3001

The joint detector 3001 uses a B-mode image signal 4001 outputted from the ultrasound image acquirer 2001 as input, and determines whether or not an object image portion indicating a joint site is in an ultrasound image signal frame. A result of either "joint present" or "joint absent" is outputted to the procedure determiner 3004. A method of determination is described later.

ii) Compression Detector 3002

The compression detector 3002 uses a B-mode image signal 4001 outputted from the ultrasound image acquirer 2001 as input, and determines whether or not an image of an ultrasound image signal frame is acquired when no compression of a subject's body surface occurs due to the ultrasound probe. A result of either "compression present" or "compression absent" is outputted to the procedure determiner 3004. A method of determination is described later.

iii) Motion-Noise Detector 3003

The motion-noise detector 3003 uses a B-mode image signal 4001 and a Doppler mode image signal 4002 outputted from the ultrasound image acquirer 2001 as input, and determines whether or not the Doppler mode image signal 4002 in an ultrasound image signal frame is caused by motion-noise. A result of either "motion-noise present" or "motion-noise absent" is outputted to the procedure determiner 3004. A method of determination is described later.

iv) Procedure Determiner 3004

The procedure determiner 3004 uses results from each of the joint detector 3001, the compression detector 3002, and the motion-noise detector 3003 as input. When a determination result is "joint capsule present", it is determined that the image was obtained under appropriate procedure. Alternatively, when a determination result is "joint capsule present", and one or both of "compression absent" and "motion-noise absent" are satisfied, it is determined that the image was obtained under appropriate procedure. At such time, the procedure determiner 3004 outputs "execute quantification" to the morphometric quantifier 2003A and the inflammation quantifier 2003B. In any other case, the procedure determiner 3004 outputs "stop quantification".

<4. Detailed Configuration of Disease Score Calculator 2003>

Returning to FIG. 3, the following describes configuration of the disease score calculator 2003. As stated above, the disease score calculator 2003 includes the morphometric quantifier 2003A and the inflammation quantifier 2003B.

(4-1) Morphometric Quantifier 2003A

First, configuration of the morphometric quantifier 2003A is described. A B-mode image signal 4001 outputted from the ultrasound image acquirer 2001 and a determination result from the evaluation determiner 2002 are inputted to the morphometric quantifier 2003A. When a determination result is "stop quantification", the morphometric quantifier 2003A does not execute quantification and invalidates disease score. On the other hand, when a determination result is "execute quantification", the morphometric quantifier 2003A calculates a disease score based on size of an image portion indicating synovial thickening and brightness pattern of an image portion indicating bone in the B-mode image signal 4001. A disease score calculated by the morphometric quantifier 2003A is referred to as a swelling score (gray scale (GS)). Swelling score is stored in the storage 1020. A method of calculating swelling score is described later.

(4-2) Inflammation Quantifier 2003B

The following describes configuration of the inflammation quantifier 2003B. A Doppler mode image signal 4002 outputted from the ultrasound image acquirer 2001, a determination result from the evaluation determiner 2002, and information indicating synovial thickening from the morphometric quantifier 2003A are inputted to the inflammation quantifier 2003B. When a determination result is "stop quantification", the inflammation quantifier 2003B does not execute quantification and invalidates disease score. On the other hand, when a determination result is "execute quantification", the inflammation quantifier 2003B calculates a disease score from size of an image region in which a Doppler signal is detected in synovial thickening 6 located between a joint capsule 5 and a bone surface in the Doppler mode image signal 4002. A disease score calculated by the inflammation quantifier 2003B is referred to as an inflammation score (power Doppler (PD)). Inflammation score is stored in the storage 1020. A method of calculating inflammation score is described later.

(4-3) Representative Disease Frame Selector 2004

Disease scores (swelling score, inflammation score) calculated by the morphometric quantifier 2003A and the inflammation quantifier 2003B and stored in the storage 1020 are inputted to the representative disease frame selector 2004. The representative disease frame selector 2004 selects one or more appropriate disease scores (representative disease score) based on predefined numerical processing, and selects a representative disease frame corresponding to the representative disease score. For example, a maximum value of disease score in a plurality of frames may be selected as a representative disease score. Alternatively, a median value or mean value of disease score in a plurality of frames may be selected as a representative disease score. When a representative disease score is a median value or mean value, if a frame exists indicating a disease score that matches the value of the representative disease score that frame is selected as a representative disease frame. When a frame does not exist indicating a disease score that matches the representative disease score, a frame indicating a disease score closest to the representative disease score may be selected as a representative disease frame. One or more representative disease scores and representative disease frames are outputted to and stored by the storage 1020.

Further, in a case in which a maximum value of disease score in a plurality of frames is selected as a most appropriate disease score, an inflammation score calculated by the morphometric quantifier 2003A and the inflammation quantifier 2003B is inputted to the representative disease frame selector 2004 and temporarily stored, and after disease scores of all frames are inputted to the representative disease frame selector 2004, a maximum value of disease score is set as a representative disease score and outputted from the representative disease frame selector 2004 to the storage 1020.

According to the present embodiment, swelling score and inflammation score are totaled, a maximum value is selected as a representative disease score, and a corresponding frame is selected as a representative disease frame. Further, swelling score and inflammation score in a representative disease frame are referred to as representative swelling score and representative inflammation score, respectively. Accordingly, a frame indicating a maximum value of swelling score and a frame indicating a maximum value of inflammation score may be different from each other, and may be different from the representative disease frame. When selecting a representative disease score, it is not necessary to use a simple total value of swelling score and inflammation score. Representative disease score may be selected based on values reached by numerical processing other than a total sum.

<Operations>

1. Operations of Ultrasound Diagnostic Device 1100

The following describes operations of the ultrasound diagnostic device 1100 when rheumatism examination is performed, using an example of a finger joint. In rheumatism examination of a finger joint, examination is performed on a joint (diagnostic site) selected from all finger joints of a subject. In examination of one joint, ultrasound examination is performed of a plurality of different cross-sections of the joint.

Figure 5:
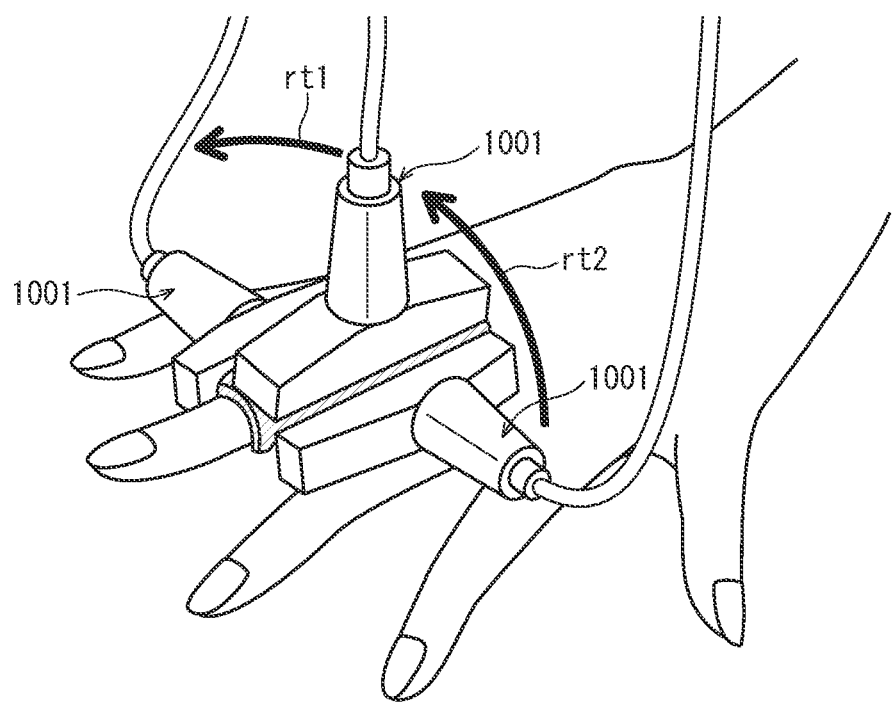
FIG. 5 is a schematic perspective view showing rheumatism examination of a finger joint.

FIG. 5 is a schematic diagram showing rheumatism examination of a finger joint using the ultrasound diagnostic device 1100. As shown in FIG. 5, the probe unit 1001 is positioned along a finger joint so the transducer array is parallel to a longitudinal direction of the finger. In this state, ultrasound scanning is performed a plurality of times at different angles of inclination relative to the joint site by rotating the probe unit 1001 about an axis of the finger as shown by rt1 and rt2, capturing a plurality of frames of ultrasound images for one finger joint. In other words, a plurality of frames of ultrasound images are captured while rotating the probe unit 1001 about an axis of the finger, each frame on a virtual plane orthogonal to the longitudinal direction of the finger and passing through the diagnostic site. Thus, rheumatism examination of one finger joint is performed based on acquisition of a plurality of frames of ultrasound images.

(1) Outline of Disease Score Calculation Processing

Figure 6:
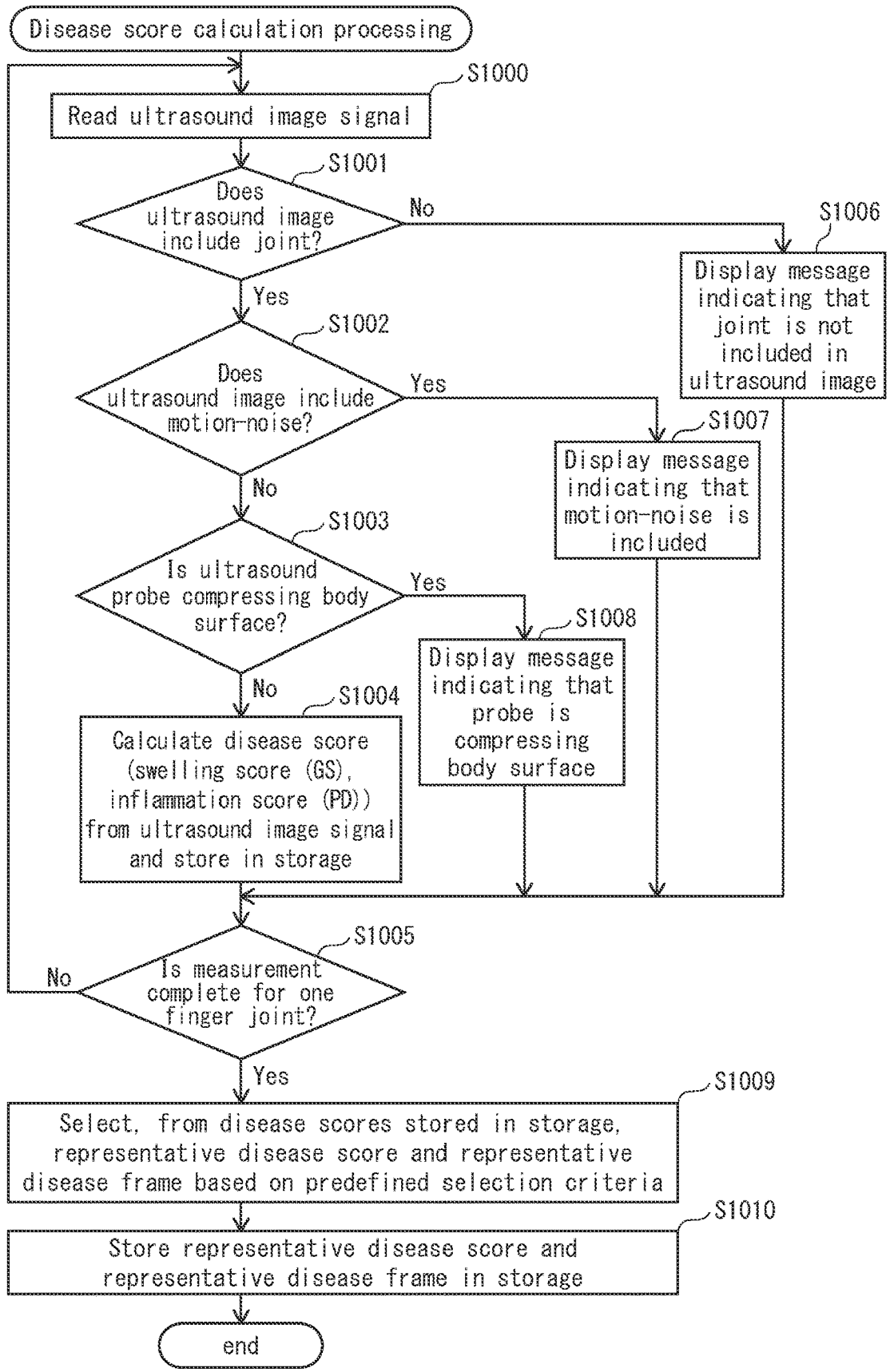
FIG. 6 is a flowchart showing disease score calculation processing.
Figure 24:
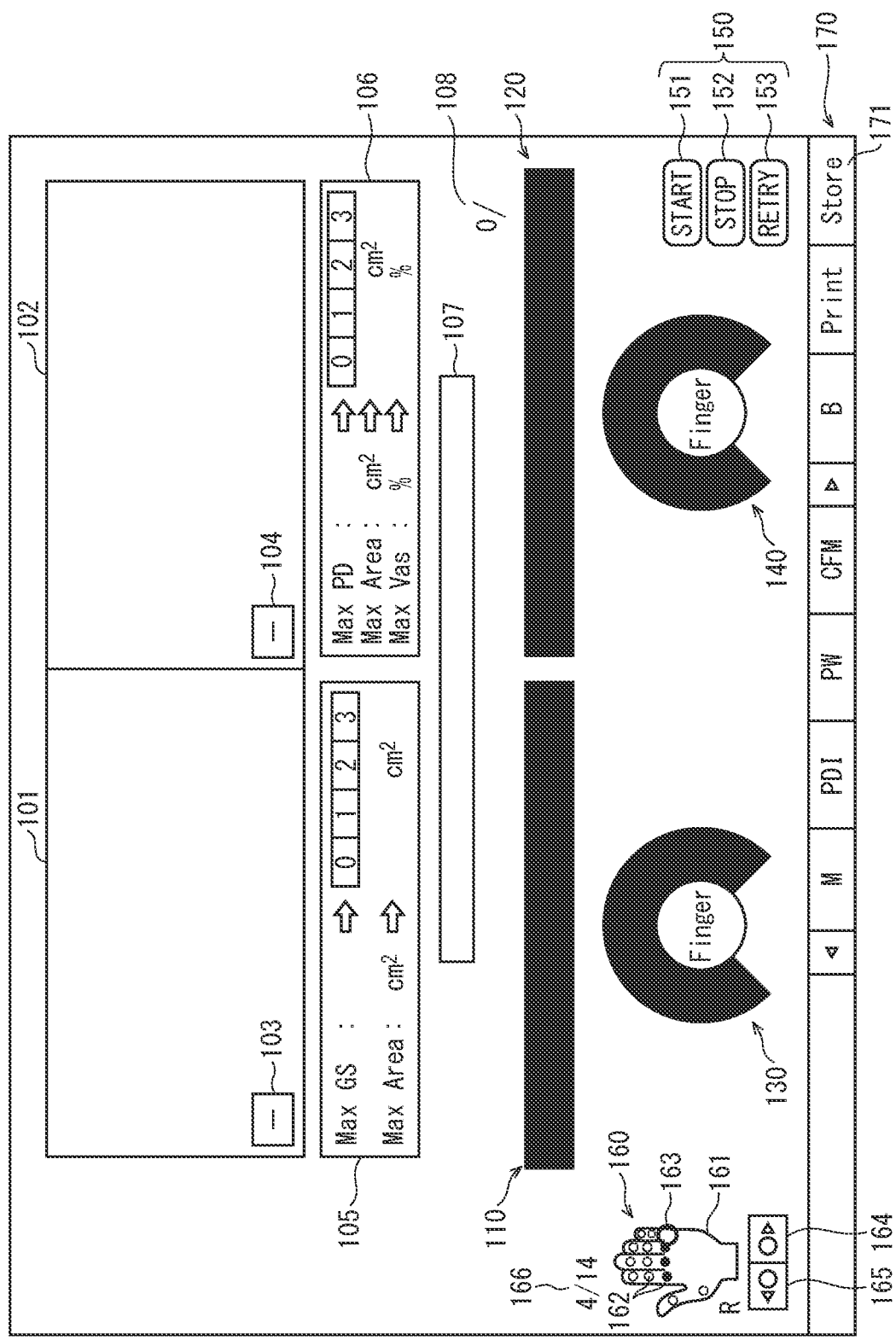
FIG. 24 shows an example of a display screen prior to starting ultrasound measurement.

FIG. 6 is a flowchart showing disease score calculation processing in the ultrasound diagnostic device 1100 pertaining to the present embodiment. A main routine (not shown) is additionally provided that controls the ultrasound diagnostic device 1100 and this subroutine of disease score calculation processing is executed each time it is called by the main routine. The subroutine of disease score calculation processing is called when ultrasound measurement is started for one diagnostic site. More specifically, according to the present embodiment, the subroutine of disease score calculation processing is called when an operator touches a START button 151 on a display screen shown prior to ultrasound measurement starting, as shown in FIG. 24.

i) Determining Evaluation Object Image

In step S1000, the ultrasound image acquirer 2001 reads a B-mode image signal 4001 and a Doppler mode image signal 4002 for each frame from B-mode image signals 4001 and Doppler mode image signals 4002 of a plurality of frames stored in the storage 1020 (that is, reads an ultrasound image signal).

Subsequently, in step S1001, the joint detector 1001 uses the B-mode image signals 4001 as input, and determines whether or not an object image portion indicating a joint site is in an ultrasound image for each ultrasound image signal frame. When an object image portion indicating a joint site is included, processing proceeds to step S1002, to determine whether or not motion-noise is included in the ultrasound image ("Yes" at step S1001, then step S1002).

In step S1002, the motion-noise detector 3003 determines whether or not a Doppler mode image signal 4002 of the ultrasound image of one frame is caused by motion-noise. When the Doppler mode image signal 4002 is not caused by motion-noise, i.e., the ultrasound image does not contain motion-noise, processing proceeds to step S1003, to determine whether or not the ultrasound probe 1001a is compressing a body surface ("No" at step S1002, then step S1003).

In step S1003, the compression detector 3002 determines whether or not the ultrasound probe 1001a is compressing a body surface of the subject. When the ultrasound probe 1001a is not compressing a body surface of the subject, processing proceeds to step S1004, in which disease scores (swelling score GS and inflammation score PD) are calculated from the ultrasound image signal and calculated disease scores are associated with frames and stored in the storage 1020.

In step S1005 it is determined whether or not disease score calculation processing has been completed for all necessary ultrasound image signal frames in examination of one finger joint (diagnostic site).

Here, in step S1001, when it is determined that an object image portion is not included in an ultrasound image, that is, when it is determined that a joint is not included in the ultrasound image ("No" at step S1001), the display controller 1016 instructs the display 1008 to display a message informing the operator that a joint is not included in the ultrasound image (step S1006). Subsequently, processing proceeds to step S1005, and whether or not disease score calculation processing has been completed for all necessary ultrasound image signal frames is determined.

Further, in step S1002, when it is determined that motion-noise is included in an ultrasound image ("Yes" at step S1002), the display controller 1016 instructs the display 1008 to display a message informing the operator that motion-noise is included in the ultrasound image (step S1007). Subsequently, processing proceeds to step S1005, and whether or not disease score calculation processing has been completed for all necessary ultrasound image signal frames is determined.

Further, in step S1003, when it is determined that the ultrasound probe 1001a is compressing a body surface ("Yes" at step S1005), the display controller 1016 instructs the display 1008 to display a message informing the operator that the ultrasound probe 1001a is compressing a body surface (step S1008). Subsequently, processing proceeds to step S1005, and whether or not disease score calculation processing has been completed for all necessary ultrasound image signal frames is determined.

In step S1005, when it is determined that disease score calculation processing is not complete for all necessary ultrasound image signal frames ("No" at step S1005), processing returns to step S1000, and an ultrasound image signal frame for which disease score calculation processing is not complete is read.

In step S1005, when it is determined that disease score calculation processing is complete for all necessary ultrasound image signal frames ("Yes" at step S1005), processing proceeds to step S1009, a representative disease score and corresponding representative disease frame are selected, and processing ends.

Here, processing of steps S1001 to S1003 in the flow of FIG. 6 corresponding to processing of the procedure determiner 3004 shown in FIG. 4. In FIG. 6, when the result of step S1001 is "joint present", the result of step S1002 is "motion-noise absent", and the result of step S1003 is "compression absent", the procedure determiner 3004 determines that the image of the object frame is an image obtained by proper procedure, and outputs the B-mode image signal 4001 and the Doppler mode image signal 4002 of the frame to the morphometric quantifier 2003A and the inflammation quantifier 2003B. The disease score calculator 2003 performs the following disease score calculation processing ("execute quantification") with respect to the B-mode image signal 4001 and the Doppler mode image signal 4002 of the frame received from the procedure determiner 3004.

ii) Disease Score Calculation

Calculation of disease score in step S1004 is performed by the disease score calculator 2003 (see FIG. 4). The morphometric quantifier 2003A outputs swelling score to the storage 1020, which the storage 1020 stores. The inflammation quantifier 2003B outputs inflammation score to the storage 1020, which the storage 1020 stores.

iii) Selection of Representative Disease Score and Representative Disease Frame

In step S1009, the representative disease frame selector 2004 (see FIG. 3) uses disease score (swelling score, inflammation score) stored by the storage 1020 as input, selects one or more representative disease scores based on predefined numerical processing, and selects representative disease frames that are corresponding ultrasound image signal frames.

Thus, it is possible to evaluate a degree of disease based on a representative disease score and corresponding representative disease frame selected based on predefined numerical processing, independent of procedure and subjectivity of an operator at the time of examination.

The following describes operation of the ultrasound diagnostic device 1100 in each step.

(2) Joint Detection Processing

Processing of step S1001 in the flow of FIG. 6 (joint detection processing) is performed by the joint detector 3001 (see FIG. 4).

Figure 7:
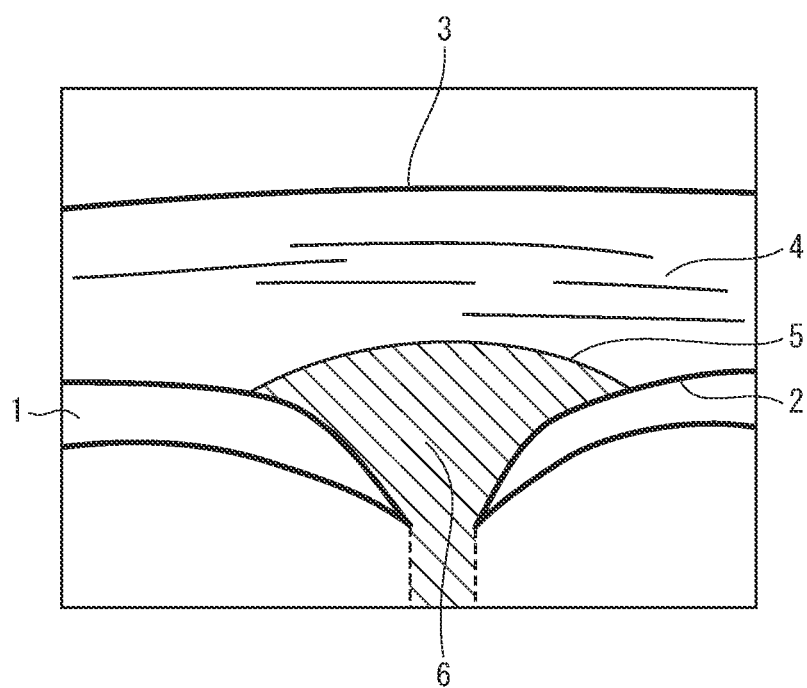
FIG. 7 is a schematic diagram showing an ultrasound image captured when a finger joint is a measurement object.

FIG. 7 is a schematic diagram showing an ultrasound image captured as a measurement object of a finger joint by using the ultrasound diagnostic device 1100, and is a B-mode image acquired by ultrasound scanning of the finger joint when the transducer array is positioned parallel to a longitudinal direction of the finger. As shown in FIG. 7, a finger joint site is drawn in the B-mode image, and includes image portions indicating bone (hereinafter, "bone") 1 and 2, an image portion indicating skin (hereinafter, "skin") 3, an image portion indicating sinew (hereinafter, "sinew") 4, and an image portion indicating a joint capsule (hereinafter, "joint capsule") 5. Bone, skin, and sinew are relatively hard tissues, and therefore the bone 1, the bone 2, the skin 3, and the sinew 4 are drawn at high brightness on the ultrasound image. A large portion of ultrasound waves are reflected at bone surfaces, and therefore bone interiors are not drawn, and only portions corresponding to bone surface and bone cortex are drawn at high brightness. The synovial thickening 6 is drawn at a lower brightness than the bone 1, the bone 2, and the skin 3. Further, synovial membrane and cartilage portions have almost no brightness value and are not displayed.

Accordingly, tissues drawn with relatively high brightness in ultrasonic images of joints are skin, sinew, and bone surfaces. The joint detector 3001 of the ultrasound diagnostic device (see FIG. 4) detects the joint capsule 5, the bone 1 and the bone 2 from the B-mode image signal to specify the synovial thickening 6 surrounded by same. Then the joint detector 3001 specifies an image portion that indicates a joint site composed of the joint capsule 5, the bone 1, the bone 2, and the synovial thickening 6.

Figure 8:
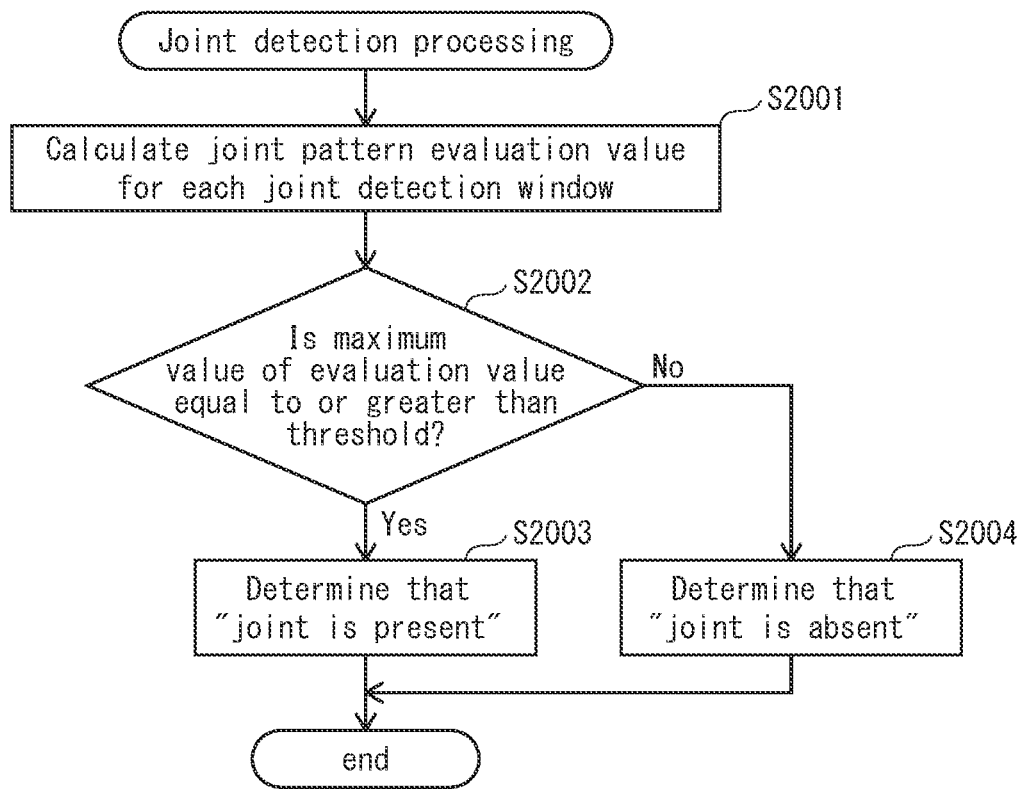
FIG. 8 is a flowchart showing joint detection processing.
Figure 9A:
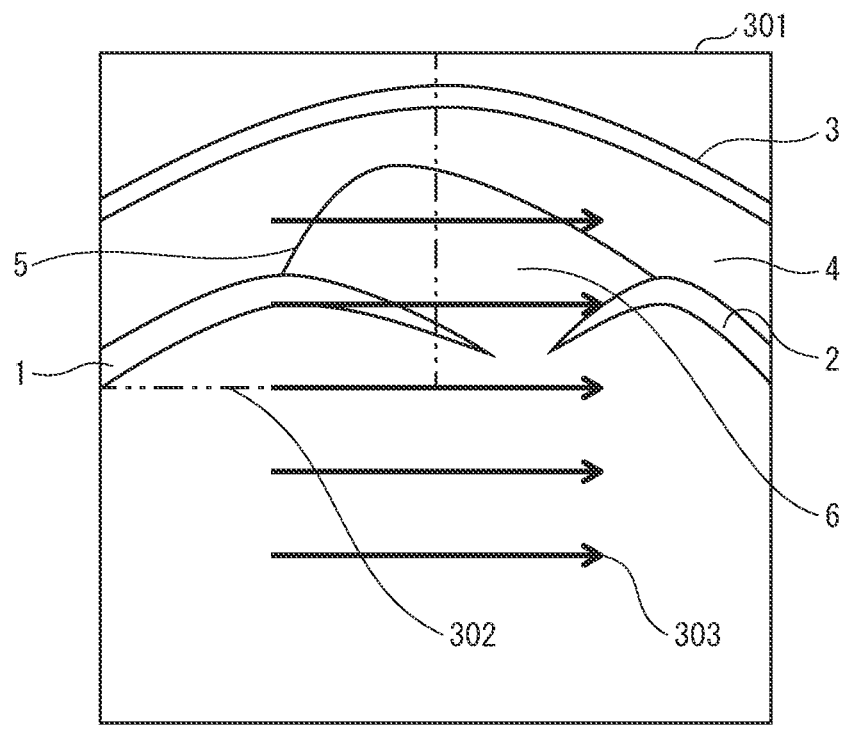
FIG. 9A is a schematic diagram for describing a joint detection window used in joint search processing and operations of joint search processing.
Figure 9B:
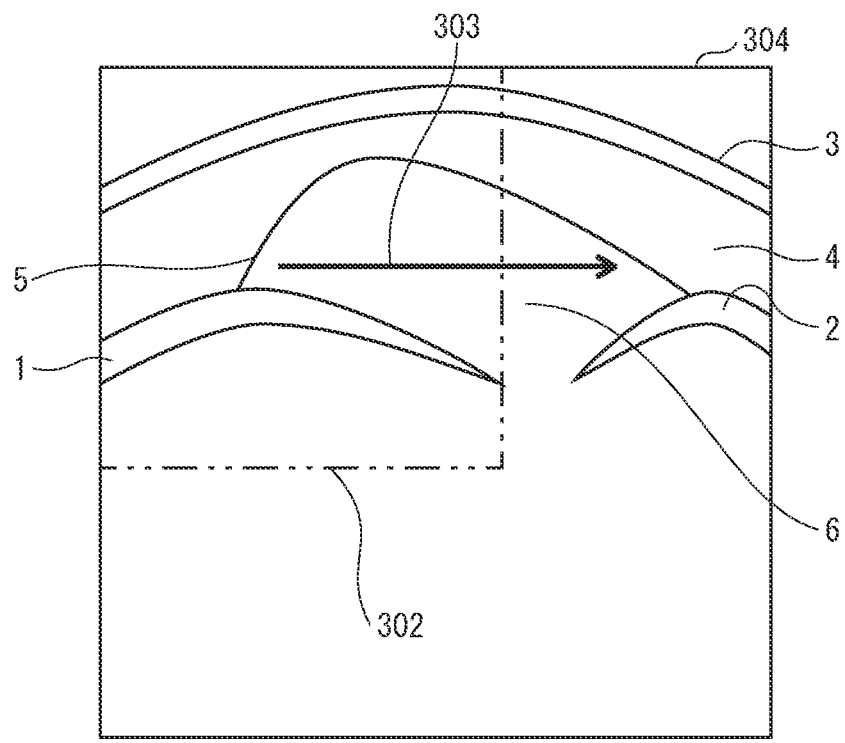
FIG. 9B is a schematic diagram showing an example of a joint detection window that has a maximum evaluation value.

FIG. 8 is a flowchart showing joint detection processing. FIG. 9A and FIG. 9B are schematic diagrams showing joint detection windows used in joint search processing. Here, the joint detector 3001 (see FIG. 4) acquires a B-mode image signal of one frame stored in the storage 1020 (see FIG. 2), via the ultrasound image acquirer 2001, and performs a search of the image that shows a joint site.

First, in step S2001 of the flow shown in FIG. 8, the joint detector 3001 calculates an evaluation value indicating likelihood of a joint pattern for each joint detection window 302, and searches for a position at which the evaluation value is maximized. Searching for a position of the joint detection window 302 at which the evaluation value is maximized is performed as follows. The joint detection window 302 is set in the B-mode image 301 and moved in a direction of scan lines 303 to perform search processing for each portion of the B-mode image 301 in the joint detection window 302 at each position, thereby performing search processing across the entirety of the B-mode image 301. Alternatively, in order to detect joints of various sizes, instead of the B-mode image 301, the B-mode image 301 may be enlarged or reduced to create a B-mode image 304, and scanning in the B-mode image 304 may be performed by the joint detection window 302.

FIG. 10 is a diagram of operations in joint search processing in the ultrasound diagnostic device 1100. As shown in FIG. 10, in joint search processing pertaining to the present embodiment, the joint detection window 302 is set on the B-mode image 301, and a template matching method is used of calculating similarity (error value, correlation value, etc.) as an evaluation value indicating likelihood of a joint pattern of the image portion in the joint detection window 302, by comparison with a template 305 showing a typical image pattern of a joint. For example, a B-mode image showing an average image pattern of a joint can be used as the template 305. The joint detection window 302 is moved in a direction of the scan lines 303 to perform search processing for each portion of the B-mode image in the joint detection window 302 at each position. The processing is repeated while moving the joint detection window 302 so that the joint detection window sweeps the entirety of the B-mode image 301, and the image portion in the joint detection window 302 at the position where the evaluation value is maximized is specified.

Figure 11:
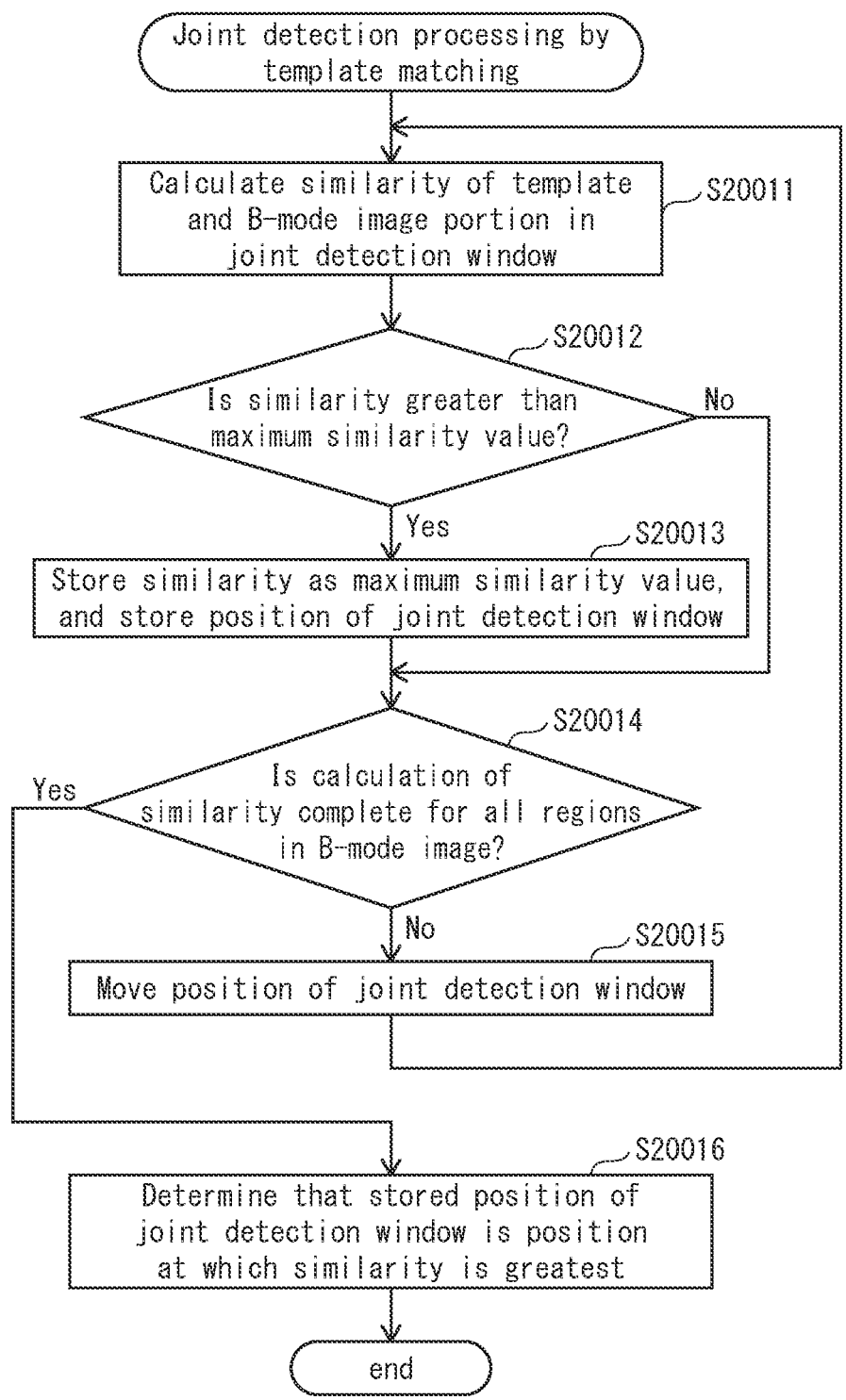
FIG. 11 is a flowchart showing joint detection processing according to template matching.

FIG. 11 is a flowchart showing joint detection processing according to a template matching method, and shows an example of processing in step S2001 of FIG. 8.

First, as shown in FIG. 10, the joint detection window 302 is set to an initial position in a top-left corner of the B-mode image 301, and similarity is calculated between the B-mode image portion in the joint detection window 302 and the template 305, which shows a typical image pattern of a joint (step S20011). Similarity is calculated by calculating a difference value in brightness information between the template 305 and the B-mode image portion in the joint detection window 302 for each pixel, and summing for all pixels included in the joint detection window 302. Alternatively, similarity is calculated by calculating a correlation value of brightness information between the template 305 and the B-mode image portion in the joint detection window 302.

When the joint detection window 302 is at the initial position, the calculated similarity is taken as the maximum value, and otherwise the calculated similarity is compared with the maximum value of similarity (step S20012).

When the calculated similarity is greater than the maximum value, the calculated similarity replaces the maximum value and the position of the joint detection window 302 is saved ("Yes" at step S20012, then step S20013). When the calculated similarity is less than or equal to the maximum value, processing proceeds to step S20014.

Subsequently, it is determined whether or not similarity calculation is complete for the entire area of the B-mode image 301 (step S20014). When it is determined that similarity calculation is not complete for the entire area of the B-mode image 301 ("No" at step S20014), position of the joint detection window 302 on the B-mode image 301 is moved by a tiny amount in an X direction or Y direction, as indicated by the scan lines 303 (step S20015), and processing returns to step S20011 to calculate similarity at the position after the move. Until similarity calculation is complete for the entire area of the B-mode image 301 in step S20014, steps S20011 to S20015 are repeated.

In step S20014, when it is determined that similarity calculation is complete for the entire area of the B-mode image 301 ("Yes" at step S20014), the position of the joint detection window 302 that is saved is specified as the position of the joint detection window 302 at which similarity is greatest (step S20016), and processing ends.

Figure 12:
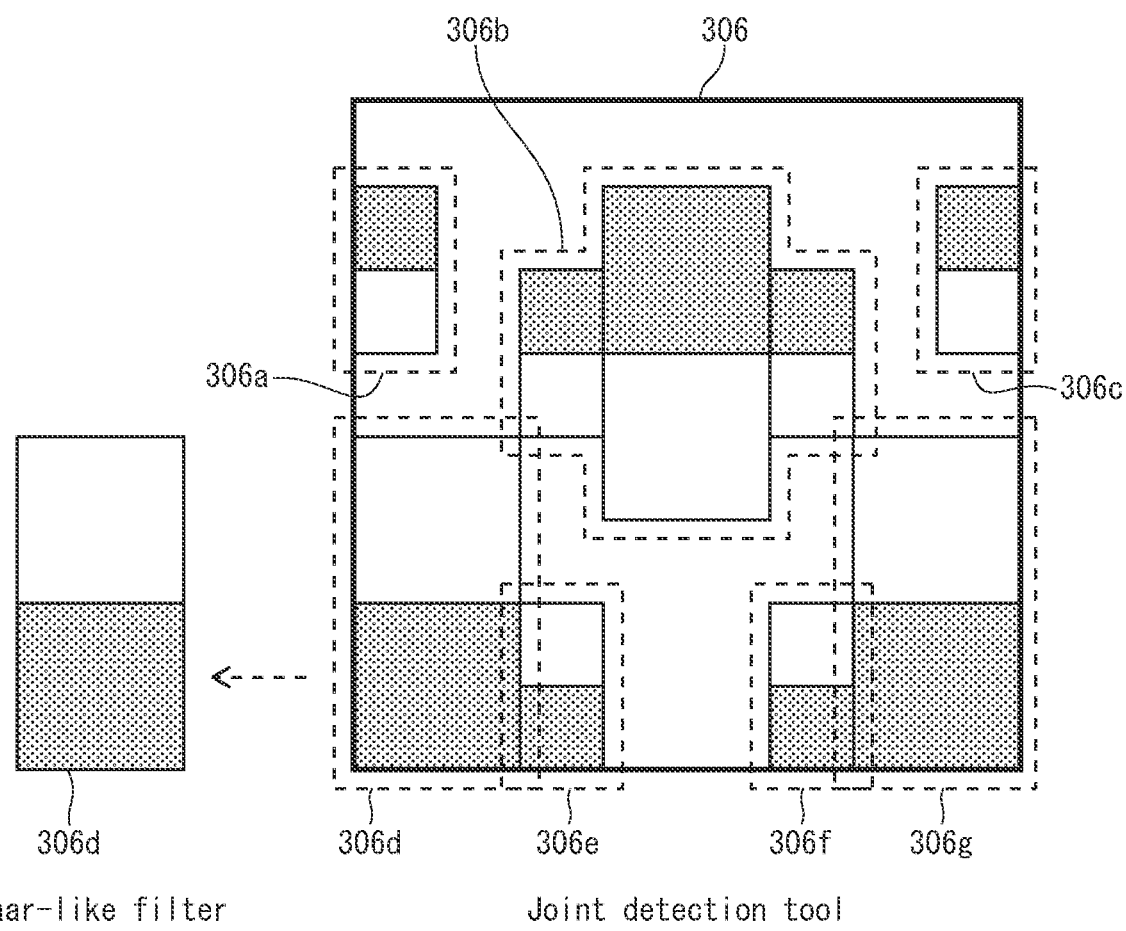
FIG. 12 is a schematic diagram showing an example of joint searching using machine learning.

Aside from the template matching method described above, the evaluation value may be a discriminator of a joint pattern/non-joint pattern using Haar-like filtering obtained by a machine learning method, for example. FIG. 12 is a schematic diagram showing an example of a joint detection tool used in machine learning. In joint searching processing using machine learning, processing similar to the flow shown in FIG. 11 is performed by using a joint detection tool 306 including a plurality of Haar-like filters 306a, 306b, 306c, 306d, 306e, 306f, 306g, instead of the template 305 that shows a typical image pattern of a joint site. Each of the Haar-like filters 306a . . . 306g is a filter for detecting brightness changes, and sensitivity and weight for position and size of the detection window, and brightness changes therein, can be obtained by a machine learning method such as AdaBoost. Output values of each filter are calculated when specifying the joint site in step S20016, and a linear combination sum of output values of each filter and weight obtained by machine learning is calculated as similarity.

Returning to FIG. 8, in step S2002, the joint detector 3001 compares the maximum value of the evaluation value and magnitude of a threshold value. The joint detector 3001, when the maximum value of the evaluation value is greater than or equal to the threshold value, determines "joint present" ("Yes" at step S2002, then step S2003); when the maximum value of the evaluation value is less than the threshold value, determines "joint absent" ("No" at step S2002, then step S2004); and outputs the result to the procedure determiner 3004. At this time, the joint detector 3001 outputs information indicating the position of the joint detection window 302 when the evaluation value is greatest to the procedure determiner 3004.

(3) Motion-Noise Detection Processing

In step S1002 of FIG. 6, the motion-noise detector 3003 (see FIG. 4) determines whether or not a Doppler mode image signal in one frame of an ultrasound image is caused by motion-noise. According to the present disclosure, motion-noise indicates a Doppler signal caused something other than blood flow, such as the operator significantly moving the probe unit 1001.

When a Doppler signal does not appear in one frame of a Doppler mode image signal, "motion-noise absent" is determined.

In the case of a Doppler signal appearing in one frame of an ultrasound image:

1) Brightness change values are calculated for each pixel between the B-mode image signal of a frame and B-mode image signal of the previous frame (hereinafter, "frame brightness difference");

2) An area ratio occupied by an area in which a Doppler signal appears in the B-mode image signal of the frame is calculated (hereinafter, "Doppler signal detection area"); and 3) The possibility of presence of motion-noise is determined by the area ratio occupied by the area in which the Doppler signal appears in a high brightness region in the B-mode image signal of the frame.

Figure 13:
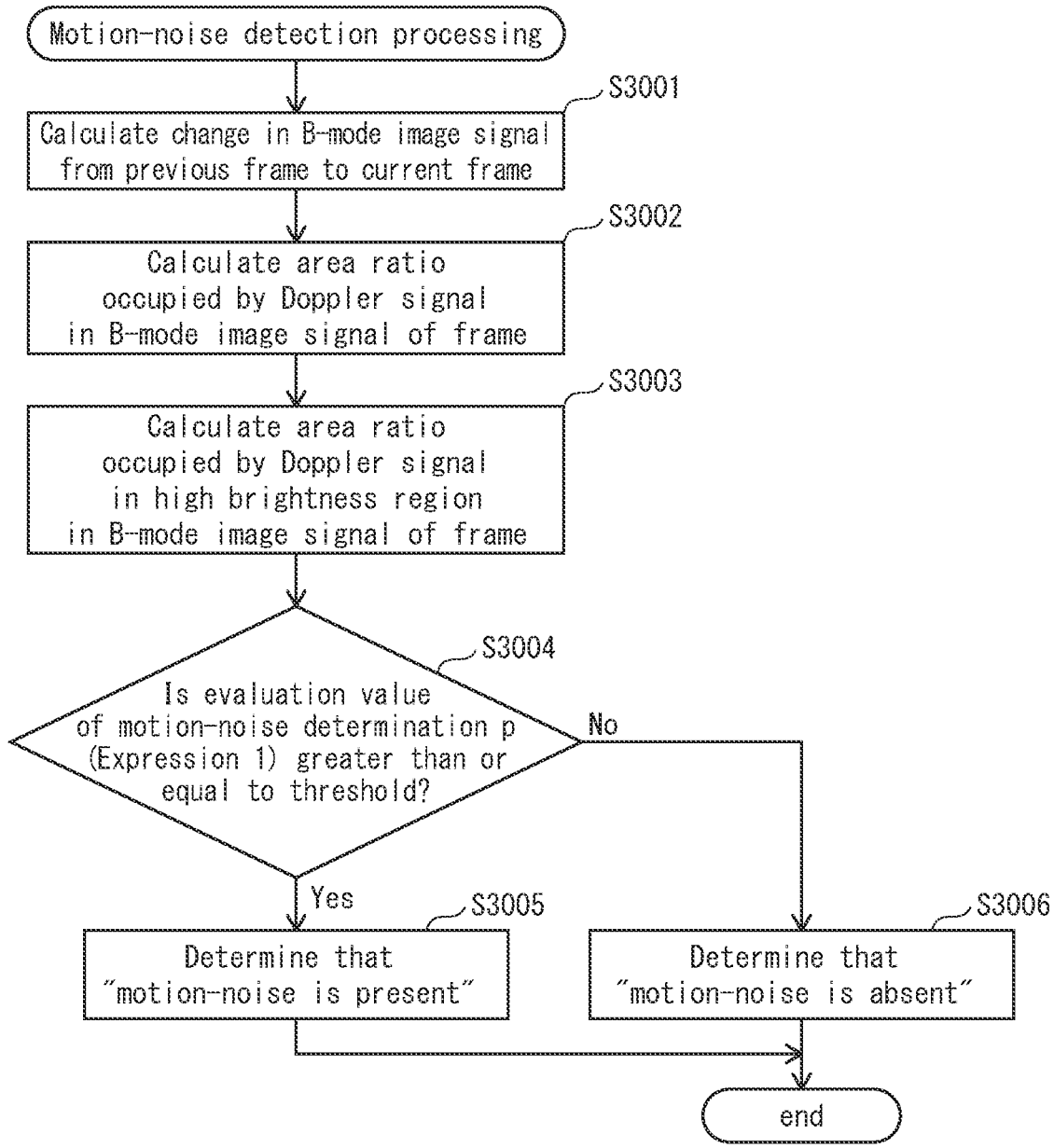
FIG. 13 is a flowchart showing motion-noise detection processing.

FIG. 13 is a flowchart showing motion-noise detection processing.

First, in step S3001, the motion-noise detector 3003 calculates a brightness change value for each pixel, comparing the B-mode image signal of the frame and the B-mode image signal of a previous frame. The brightness change value is a correlation value between frames, and when the operator significantly moves the ultrasound probe, the correlation value between frames becomes low. As an alternative to correlation value, a difference sum of pixel values may be used.

Next, in step S3002, the motion-noise detector 3003 calculates an area ratio occupied by a Doppler signal detected region in the B-mode image signal of one frame. More specifically, a ratio is calculated between a pixel count in which a Doppler signal appears and a total pixel count in the B-mode image signal of the frame.

Figure 14A:
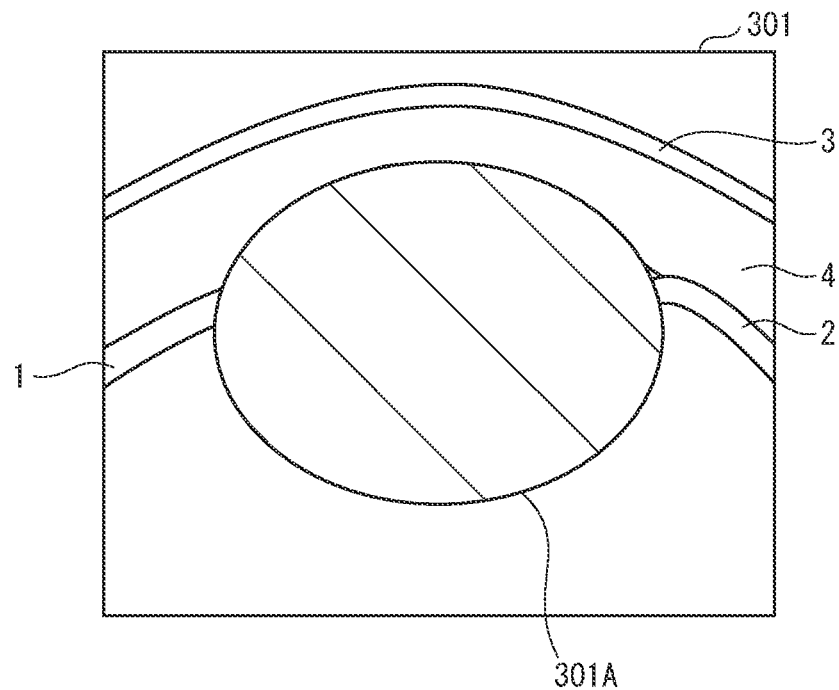
FIG. 14A is a schematic diagram showing an example of a B-mode image in which motion-noise is generated in a relatively large range.
Figure 14B:
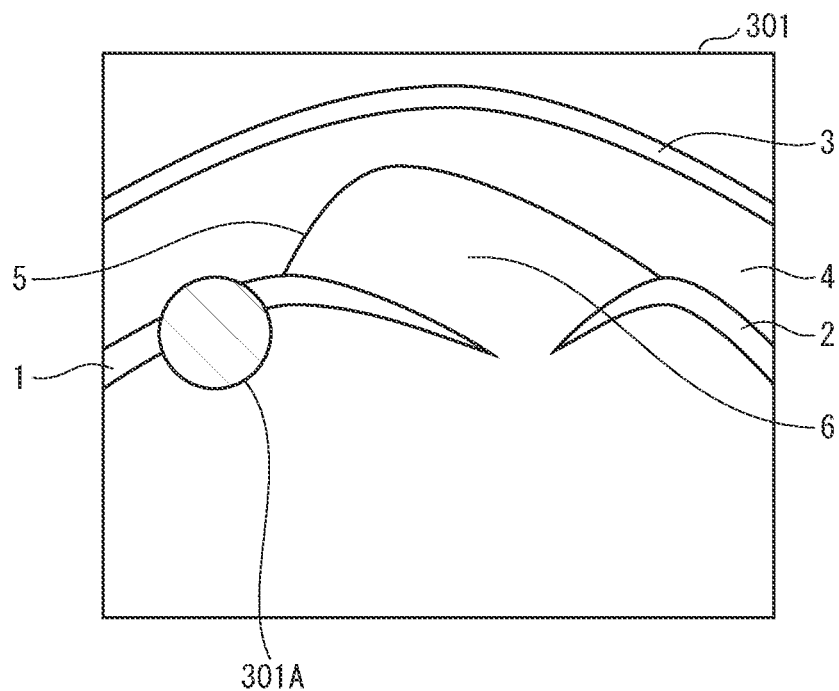
FIG. 14B is a schematic diagram showing an example of a B-mode image in which motion-noise is generated in a region of high brightness.

FIG. 14A and FIG. 14B are schematic diagrams showing examples of motion-noise occurring in single frames of B-mode images. In FIG. 14A, a Doppler signal detected region 301A is present in a large range in the B-mode image 301. A Doppler signal is used as a signal indicating blood flow velocity, but in principle is a signal that captures movement of a substance and isn't limited to blood flow. Accordingly, when the operator significantly moves the probe unit 1001, the subject moves significantly relative to the probe unit 1001, which may cause a Doppler signal to be generated as movement of a portion of a substance in the subject. In such a case, as shown in FIG. 14A, the Doppler signal detected region 301A occupies a large range in the B-mode image 301. Accordingly, when the area ratio of the Doppler signal detected region 301A is large in the B-mode image 301, it can be determined that motion-noise is occurring.

Next, in step S3003 of the flow in FIG. 13, the motion-noise detector 3003 (see FIG. 4) calculates an area ratio occupied by a Doppler signal detected region in a high brightness region in the B-mode image signal of the frame. More specifically, the motion-noise detector 3003 calculates a pixel ratio of pixels in which a Doppler signal appears in a region occupied by pixels that indicate a predefined brightness in the B-mode image signal of the frame. In a B-mode image, regions of high brightness are regions of hard tissues in the subject, and correspond to bones and the like. Blood flow does not exist in such regions, and therefore, as shown in FIG. 14B, it can be determined that motion-noise is occurring when a portion of the Doppler signal detected region 301A exists in the bone 1, which is a region of high brightness in the B-mode image 301.

Next, in step S3004, the motion-noise detector 3003 calculates an evaluation value of motion-noise determination, and determines whether or not it is less than a threshold value. A motion-noise determination evaluation value p is given by Expression 1. In Expression 1, Mx is brightness difference between frames in B-mode image signals, My is an area ratio occupied by a Doppler signal detected region in the B-mode image signal of one frame, Mz is an area ratio occupied by a Doppler signal detection region in a high brightness region in the B-mode image signal of the one frame, and ma, mb, and mc are constants.

$$p = ma \cdot Mx + mb \cdot My + mc \cdot Mz \qquad \text{[Expression 1]}$$

Mx, My, and Mz may be normalized, using 0 to 1 as minimum and maximum values. The greater the evaluation value p, the greater the possibility of motion-noise. The motion-noise detector 3003 determines "motion-noise present" when the motion-noise determination evaluation value p is equal to or greater than a threshold value, determines "motion-noise absent" when lower than the threshold value, and outputs the result of determination to the procedure determiner 3004.

(4) Body Surface Compression Detection Processing

In step S1003 of FIG. 6, the compression detector 3002 (see FIG. 4) determines whether or not the ultrasound probe 1001a is compressing the body surface of the subject. While acquiring an ultrasound image, when a body surface of the subject is compressed by the ultrasound probe 1001a, new blood vessels in the subject may be compressed, and may not appear as an inflammation reaction in the ultrasound image. Thus, an ultrasound image acquired when a body surface of the subject is being compressed by the ultrasound probe 1001a is not appropriate as a rheumatism evaluation image, and is excluded from consideration as an evaluation object.

Angiogenesis is a physiological phenomenon in which a new blood vessel branch branches from an existing blood vessel to construct a vascular network. When a joint develops inflammation and synovial thickening occurs, new blood vessels are generated to supply oxygen and nutrients to cells of thickened tissue. The greater the degree of inflammation, the greater the number and size of new blood vessels.

A specific determination in step S1003 is performed based on whether or not an image portion indicating an ultrasound gel medium layer satisfying a predefined criterion of thickness is present between the body surface of the subject and the surface of the ultrasound probe 1001a.

Figure 15:
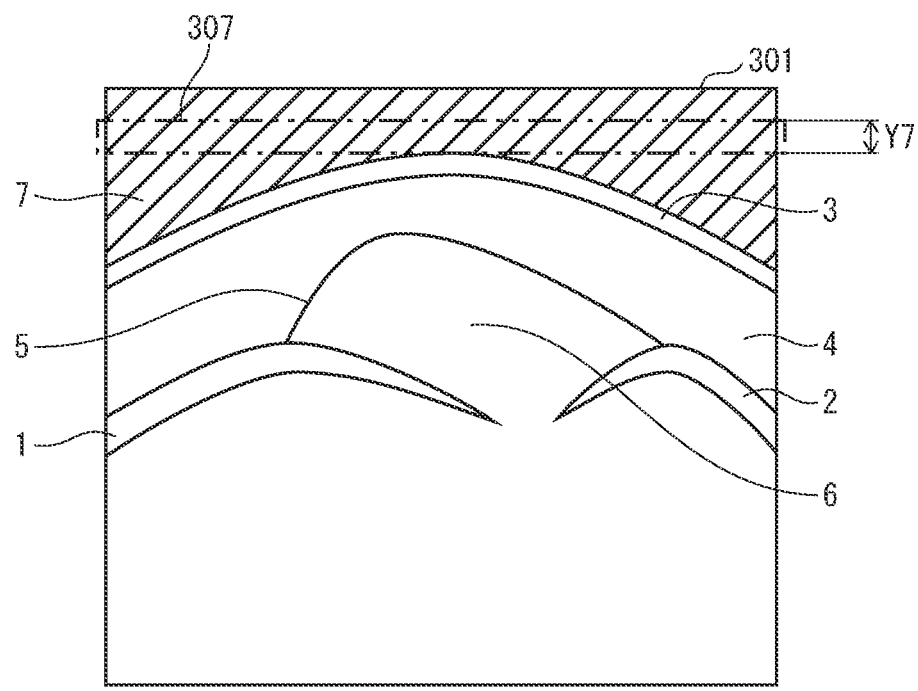
FIG. 15 is a schematic diagram of a B-mode image for describing body surface compression detection processing.

FIG. 15 is a schematic diagram of a B-mode image for describing body surface compression detection processing. It is determined whether or not the image portion indicating an ultrasound gel medium layer (hatched portion in FIG. 15, hereinafter "ultrasound gel medium layer") 7 exists between the ultrasound probe 1001a and the skin 3 at an upper edge portion of the B-mode image 301. The ultrasound gel medium layer 7 is low brightness and low variance, indicated by solid black in the image, and therefore whether or not the ultrasound gel medium layer 7 exists can be determined by whether or not a low brightness, low variance region exists at an upper portion of the B-mode image 301. Thus, as shown in FIG. 15, a gel determination region 307 that is rectangular in a predefined range is set in the upper portion of the B-mode image 301, and average brightness and variance of pixels in the gel determination region 307 are calculated and compared to threshold values. A range Y7 (length in depth direction) of the gel determination region 307 is preferably set 3 mm to 5 mm from the top of the B-mode image 301. In the upper end portion of the B-mode image 301, a region having brightness may appear due to multiple reflection of ultrasound waves in the ultrasound probe 1001a. By excluding a range of less than 3 mm from the top of the B-mode image 301, the influence of multiple reflections can be avoided, and presence or absence of the ultrasound gel medium layer 7 can be determined more accurately.

Figure 16:
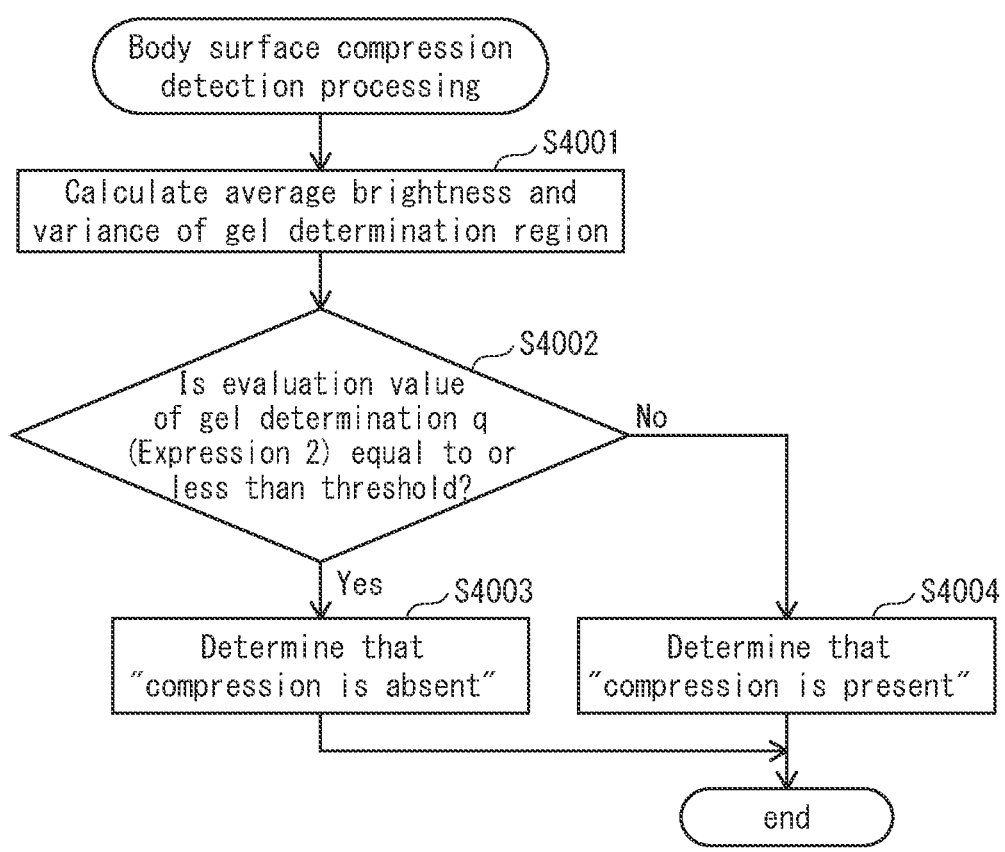
FIG. 16 is a flowchart showing body surface compression detection processing.

FIG. 16 is a flowchart showing body surface compression detection processing.

In step S4001, the compression detector 3002 (see FIG. 4) calculates an average value and variance value of brightness of the gel determination region 307 in the B-mode image 301, and calculates, from the variation value, whether brightness distribution of the ultrasound gel medium layer 7 is uniform.

Subsequently, in step S4002, a gel determination evaluation value q is calculated and compared to a threshold value. Gx is an average value of brightness of the gel determination region 307, Gx is variance, gd and ge are constants, and the gel determination evaluation value q is given by Expression 2.

$$q = ga \cdot Gx + gb \cdot Gy \qquad \text{[Expression 2]}$$

The smaller the gel determination evaluation value q, the higher the probability the ultrasound gel medium layer 7 is present. When the gel determination evaluation value q is equal to or less than the threshold value, the compression detector 3002 determines that the ultrasound gel medium layer 7 is present at a sufficient thickness, and therefore determines "compression absent" ("Yes" at step S4002, then step S4003).

When the gel determination evaluation value q is greater than the threshold value, the compression detector 3002 determines that the ultrasound gel medium layer 7 is not present at a sufficient thickness, and therefore determines "compression present" ("No" at step S4002, then step S4004), and outputs the result to the procedure determiner 3004 (see FIG. 4).

(5) Determining Evaluation Object

When, according to the flow in FIG. 6, the result at step S1001 is "joint present", the result at step S1002 is "motion-noise absent", and the result at step S1003 is "compression absent", the procedure determiner 3004 (see FIG. 4) determines that the image of the frame is an image obtained by proper procedure, and outputs, along with date of the frame, information indicating that the frame is an object for disease score calculation processing to the morphometric quantifier 2003A (see FIG. 4) and the inflammation quantifier 2003B (see FIG. 4). In addition, information indicating position of the joint detection window 302 at a maximum evaluation value is outputted to the morphometric quantifier 2003A and the inflammation quantifier 2003B.

When the result at step S1001 is "joint absent", the result at step S1002 is "motion-noise present", or the result at step S1003 is "compression present", the procedure determiner 3004 determines that the image of the frame is not an image obtained by proper procedure, and outputs information indicating the frame is not an object for disease score calculation processing to the morphometric quantifier 2003A and the inflammation quantifier 2003B, and processing ends.

The procedure determiner 3004 determines whether or not an ultrasound image of a frame is an image obtained by proper procedure as described above, and because only ultrasound images determined to be obtained by proper procedure are designated as objects for disease score calculation processing, more accurate disease scores can be obtained.

(6) Calculation of Swelling Score (GS)

Figure 17:
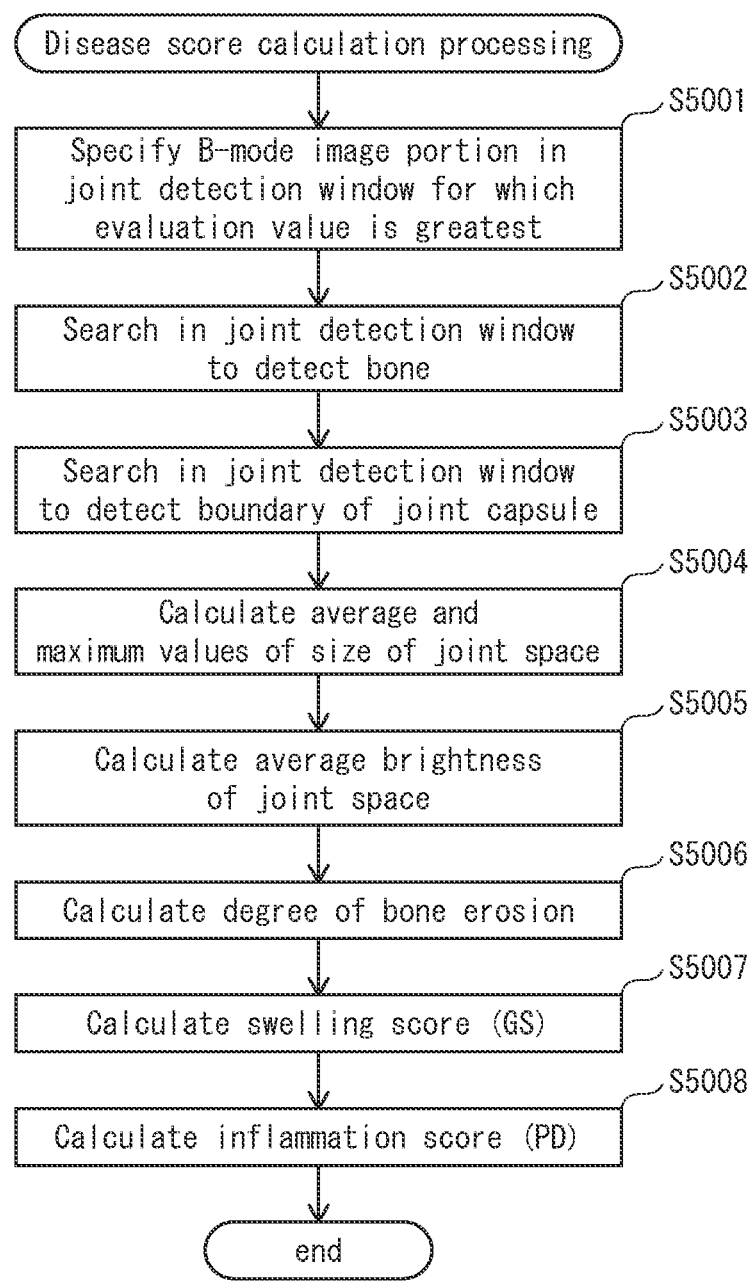
FIG. 17 is a flowchart showing disease score calculation processing.

The disease score calculation processing in step S1004 of FIG. 6 is performed by the disease score calculator 2003 (see FIG. 4). More specifically, the morphometric quantifier 2003A of the disease score calculator 2003 (see FIG. 4) calculates a disease score (swelling score) from size of synovial thickening, brightness, and degree of bone erosion in a B-mode image. FIG. 17 is a flowchart showing disease score calculation processing.

i) Calculation of Synovial Thickening Size and Brightness

First, the morphometric quantifier 2003A specifies a portion of the B-mode image 301 indicating a joint site, based on information indicating a position of the joint detection window 302 (see FIG. 9B) at a maximum evaluation value (S5001), then detects bone from the portion of the B-mode image 301 in the joint detection window 302.

Figure 18:
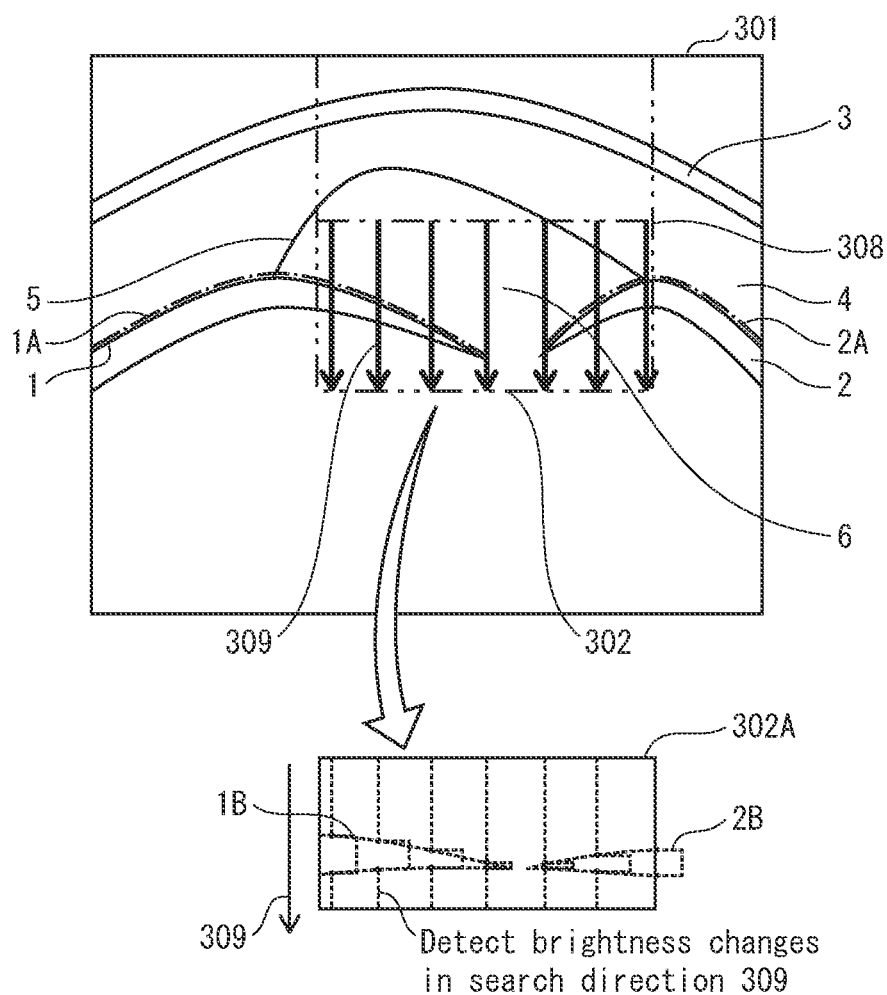
FIG. 18 is a schematic diagram for describing detection of bone 1 and bone 2 in a B-mode image.

FIG. 18 is a schematic diagram for describing processing detecting the bone 1 and the bone 2. As stated above, bone is relatively hard tissue, and therefore drawn at high brightness in an ultrasound image. A large portion of ultrasound waves are reflected at bone surfaces, and therefore bone interiors are not drawn, and only portions corresponding to bone surface and bone cortex are drawn at high brightness.

The bone 1 and the bone 2 are present in the joint detection window 302, below a depth center position 308 of the joint detection window 308. Thus, a portion of the B-mode image 301 in a region below the depth center position 308 of the joint detection window 302 is designated as a search range. Taking the depth center position 308 of the joint detection window 302 as a start point, and a direction downwards therefrom as a search direction 309 (direction of arrows in the drawing), brightness changes in the search direction 309 are detected (S5002). It is possible to decrease erroneous detection of a boundary by performing search processing in a direction in which detected brightness goes from low brightness to high brightness. The bone 1 and the bone 2 are high brightness in the B-mode image 301, and therefore boundaries 1A and 2A between the bone 1 and the bone 2 and a surrounding image portion can be detected by using an active contour model (snakes) or the like. As shown in FIG. 18, when detected boundaries 1B and 2B are sudden changes in the search direction 309 and changes in a direction perpendicular to the search direction at a position of the boundaries 1B and 2B are gradual, the boundaries 1B and 2B can be specified as the boundaries 1A and 2A of the bone 1 and the bone 2, respectively.

Figure 19:
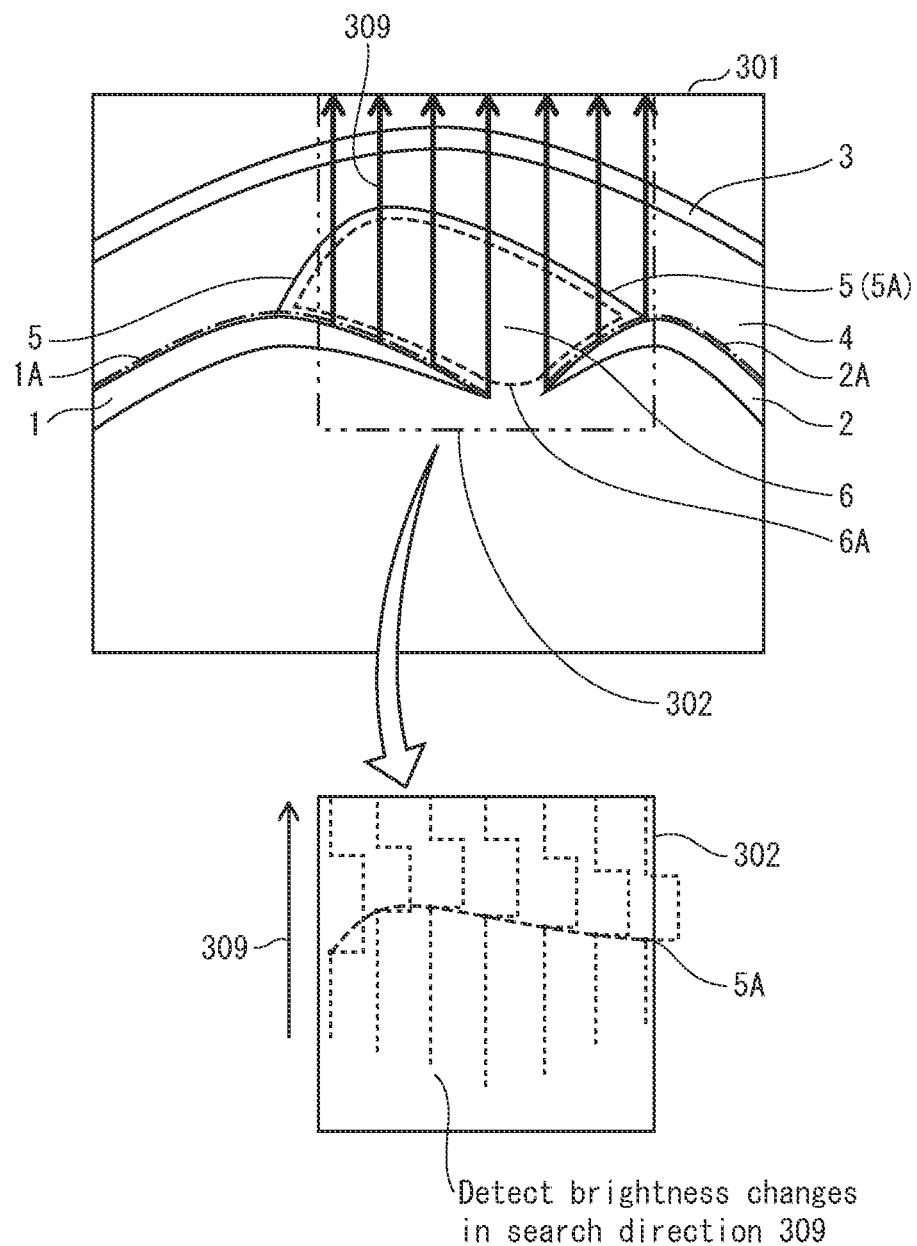
FIG. 19 is a schematic diagram for describing detection of a boundary of a joint capsule in a B-mode image.

Subsequently, the morphometric quantifier 2003A detects a boundary of the joint capsule. FIG. 19 is a schematic diagram for describing processing detecting the joint capsule 5. The joint capsule 5 is present above the bone 1 and the bone 2 in the joint detection window 302. Thus, a portion of the B-mode image 301 in a region above the bone 1 and the bone 2 in the joint detection window 302 is designated as a search range. As mentioned above, performing search processing in a direction from low brightness to high brightness decreases inaccurate detection of boundaries. Taking the area surrounding the bone 1 and the bone 2 and the boundaries 1A and 2A in the joint detection window 302 as a start point, and a direction upwards therefrom as the search direction 309 (direction of arrows in the drawing), brightness changes in the search direction 309 are detected (S5003).

In the B-mode image 301, brightness of an image portion indicating a fat layer or muscle layer above the joint capsule 5 is higher than that of the synovial thickening 6, and using an active contour model (snakes) a boundary 5A can be detected between the joint capsule 5 and the synovial thickening 6. As shown in FIG. 19, when the boundary 5A is a sudden change in the search direction 309 and changes in a direction perpendicular to the search direction at a position of the boundary 5A are gradual, the boundary 5A can be specified as the joint capsule 5. Alternatively, the joint capsule 5 may be specified by image processing such as a region expansion method based on similarity of brightness values.

Subsequently, it can be evaluated that the greater the synovial thickening 6, the higher the degree of disease, and therefore the morphometric quantifier 2003A (see FIG. 4) calculates the size of the synovial thickening 6. Size of the synovial thickening 6 can be calculated as area or distance in the depth direction between the boundaries 1A, 2A and the joint capsule 5 (5A).

First, an average value and a maximum value of length of the synovial thickening along a direction perpendicular to the search direction 309 are calculated (step S5004).

Subsequently, the morphometric quantifier 2003A calculates average brightness of the synovial thickening 6 (step S5005). When average brightness of the synovial thickening 6 is low, it can be evaluated that the degree of disease is high. Average brightness of the synovial thickening 6 can be calculated by averaging brightness of each pixel included in the synovial thickening 6, which is a portion surrounded by the bone boundaries 1A, 2A and the joint capsule 5 (5A). The synovial thickening 6, in FIG. 19, is a range surrounded by a periphery 6A of the synovial thickening 6. Alternatively, instead of average brightness, a median value of brightness in the synovial thickening 6 may be calculated.

ii) Calculating Degree of Bone Erosion

Subsequently, the morphometric quantifier 2003A (see FIG. 4) calculates a degree of bone erosion 7 (step S5006). When the degree of bone erosion 7 is high, it can be evaluated that the degree of disease is high.

Figure 20:
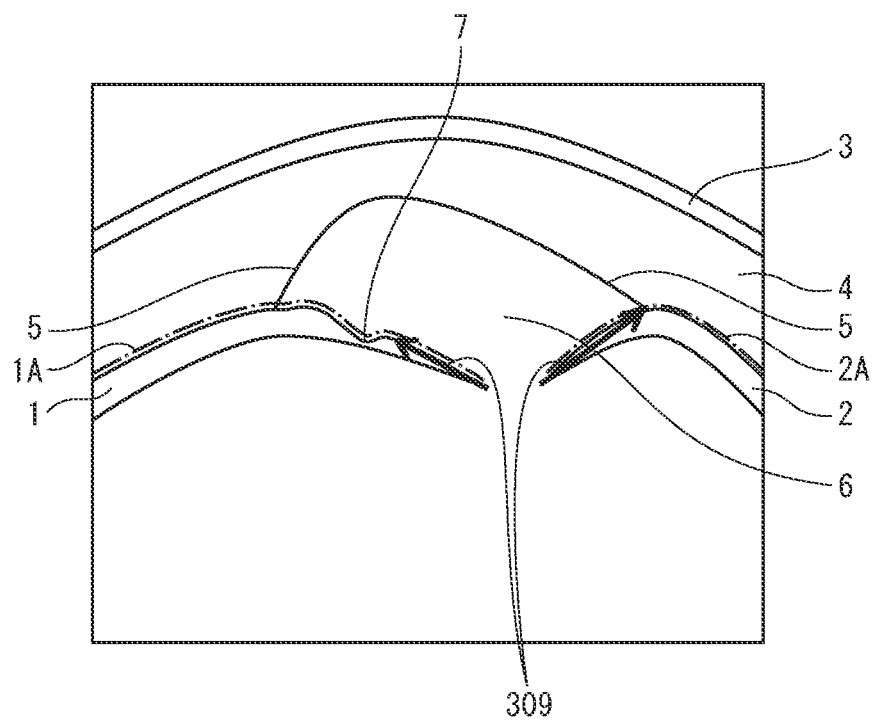
FIG. 20 is a schematic diagram for describing evaluation of bone erosion in a B-mode image.

FIG. 20 is a schematic diagram for describing processing evaluating a degree of bone erosion 7. A degree of bone erosion 7 can be evaluated according to smoothness of the boundary 1A between the synovial thickening 6 and the bone 1 and the boundary 2A between the synovial thickening 6 and the bone 2. More specifically, as shown in FIG. 20, evaluation of smoothness is performed along the boundary 1A and the boundary 2A from the deepest ends thereof in the search direction 309. More specifically, for example, smoothness is evaluated by fitting the boundaries 1A, 2A to fitting curves and calculating fitting error.

Figure 21:
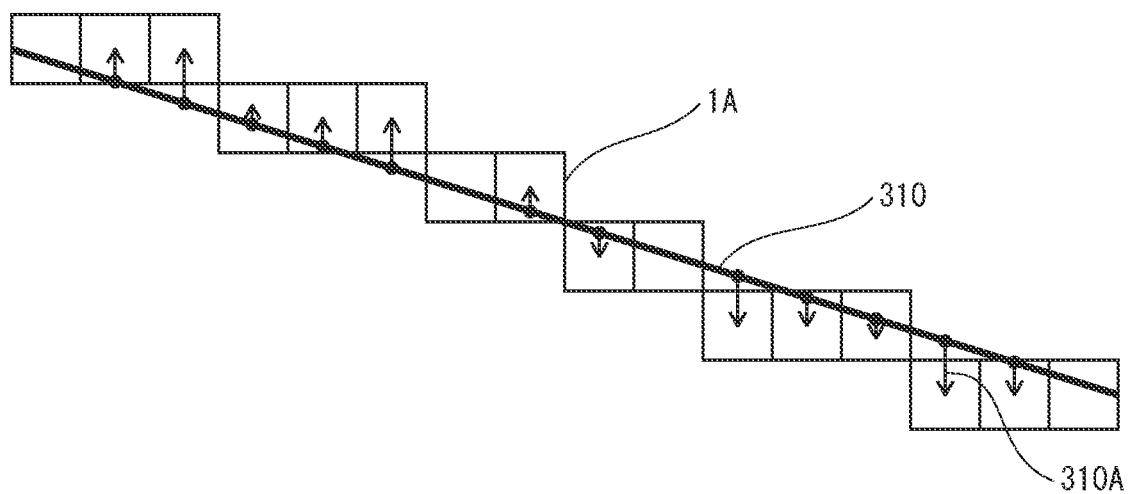
FIG. 21 is a schematic diagram showing an example of fitting at a boundary of a normal bone surface.
Figure 22:
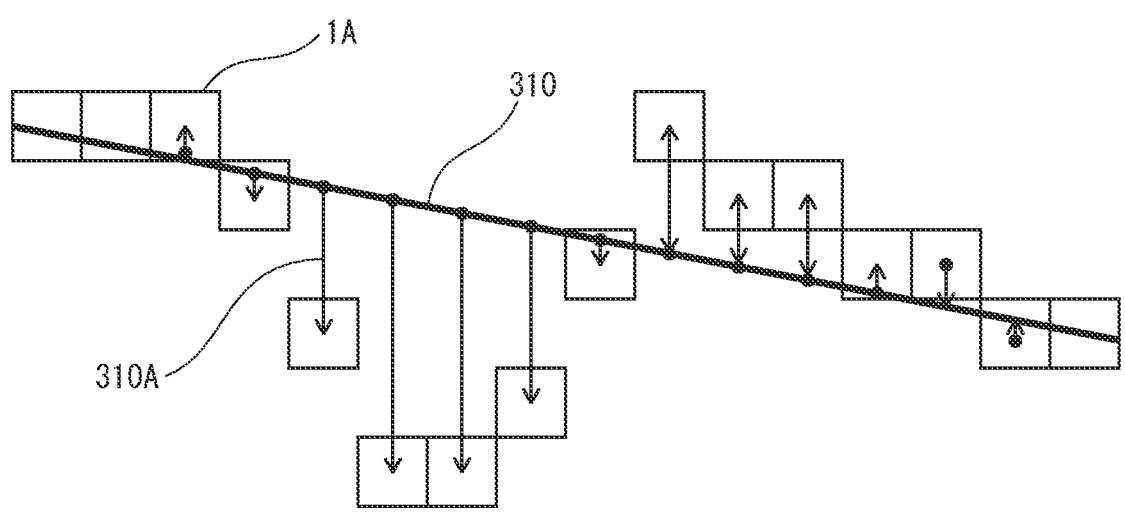
FIG. 22 is a schematic diagram showing an example of fitting at a boundary of an eroded bone surface.

FIG. 21 is a schematic diagram showing an example of fitting a boundary of a normal bone surface. FIG. 22 is a schematic diagram showing an example of fitting a boundary of an eroded bone surface. FIG. 21 and FIG. 22 each show an image indicating a bone boundary (hereinafter, "boundary") 1A and an example of a fitting curve 310. At the boundary of the eroded bone surface shown in FIG. 22, a fitting error 310A (magnitude of deviation between the boundary 1A and the fitting curve 310) is larger than that of the boundary of the normal bone surface shown in FIG. 21; the greater the degree of bone erosion, the greater the fitting error 310A. Accordingly, the degree of bone erosion can be evaluated by accumulating the fitting error 310A along the fitting curve 310. Although the curve used for fitting is arbitrary, if a curve that fits the eroded part of bone is used the fitting error becomes small and the degree of bone erosion cannot be accurately evaluated. Accordingly, it is preferable to select a degree that does not fit the eroded part for the function of the fitting curve.

Alternatively, instead of using the fitting curve method described above, smoothness of a bone surface may be evaluated by detecting change in a direction along the bone surface by first-order differentiation or second-order differentiation of the bone boundary. According to such a method, it is possible to eliminate influence of shape changes between bone surfaces when evaluating smoothness of the bone surfaces.

iii) Calculating Swelling Score

Returning to FIG. 17, the morphometric quantifier 2003A (see FIG. 4) next calculates a swelling score, which is one type of disease score. The swelling score is given by Expression 3, when GSz is size of the synovial thickening 6, GSy is brightness of the synovial thickening 6, GSz is degree of bone erosion, and gsa, gsb, and gsc are constants.

$$GS = gsa \cdot GSx + gsb \cdot GSy + gsc \cdot GSz \qquad \text{[Expression 3]}$$

According to investigation by the inventors, it is possible to evaluate degree of disease more accurately by using a swelling score (GS) in which three parameters that are highly correlated with disease progression, GSx, GSy, and GSz, are linearly combined. GSx, GSy, and GSz may be normalized to a minimum value and maximum value from zero to one. Subsequently, as described above, the morphometric quantifier 2003A outputs the swelling score to the storage 1020 (see FIG. 2), which the storage 1020 stores (step S1004 in FIG. 6). The morphometric quantifier 2003A outputs position information indicating the synovial thickening 6 to the inflammation quantifier 2003B (see FIG. 4).

According to the above configuration, a disease score that quantifies a degree of disease can be calculated for each evaluation object frame from object image portion signals in evaluation object frame B-mode image signals, and objectivity of evaluation is improved.

(7) Calculating Inflammation Score (PD)

(7-1) Specification of New Blood Vessels

As a method of image diagnosis for evaluating joint disease, including rheumatoid arthritis, a region of blood flow is specified and presence or absence of angiogenesis due to disease is determined. When a substance in a subject moves, a Doppler signal is generated due to the movement. Blood flow, which is blood movement, is movement of substances including erythrocytes and the like in the blood, and therefore generates a Doppler signal, from which a region in which blood flow is present can be specified.

However, in a Doppler mode image itself, only a region in which blood flow is present can be specified. Thus, it is important to make a distinction as to whether a region in which blood flow is present indicates a new blood vessel caused by disease or a blood vessel that existed prior to the disease (existing blood vessel), to specify new blood vessels.

The following are examples of methods that can be used to distinguish new blood vessels and existing blood vessels and specify new blood vessels.

A new blood vessel is usually a finer blood vessel than an existing blood vessel, and therefore the smaller the area of the blood flow region or width of the blood flow region, the higher the possibility that it is a new blood vessel. Thus, a feature amount related to area or width of a blood flow region (hereinafter, "self-feature amount") is extracted from the Doppler mode image.

Further, new blood vessels usually develop within a synovial thickening region, and therefore the nearer a blood flow region is to a joint center in a horizontal distance, the more likely it is a new blood vessel. Furthermore, existing blood vessels are usually arranged in a direction along skin or bone, and therefore the higher the degree of coincidence between shape of a blood flow region and shape of skin surface or bone surface, the more likely the blood flow region indicates an existing blood vessel, and conversely the lower the degree of coincidence, the more likely it indicates a new blood vessel. Thus, a feature amount related to degree of coincidence between shape of a blood flow region and shape of a skin surface or bone surface (hereinafter, "relative feature amount") is extracted from the Doppler mode image.

Then, the possibility of being a new blood vessel is quantitatively evaluated based on the self-feature amount and the relative feature amount, and a new blood vessel is specified. Specification of a new blood vessel may be performed when the possibility is equal to or greater than a threshold value, for example.

According to the present embodiment, in addition to specifying a new blood vessel by a method described above, a region for which the possibility of being a new blood vessel is less than the threshold value but still high is specified as a possible new blood vessel. For example, when a threshold value for determining a new blood vessel is a first threshold value, a second threshold value is set lower than the first threshold value, and if the possibility of being a new blood vessel is equal to or greater than the second threshold value and less than the first threshold value it may be specified as a possible new blood vessel.

(7-2) Calculating Inflammation Score (PD)

In the flow of FIG. 17, the inflammation quantifier 2003B (see FIG. 4) uses position information indicating the synovial thickening 6 from the morphometric quantifier 2003A (see FIG. 4) as input, and calculates an inflammation score based on a Doppler image signal (step S5008).

In step S5005, the inflammation quantifier 2003B sets the synovial thickening 6 as a region of interest (ROI), based on a range of the synovial thickening 6 specified by the morphometric quantifier 2003A, and calculates an area (PDy) occupied by the region of interest. Further, the inflammation quantifier 2003B calculates an area (PDx) occupied by pixels of the region specified as a new blood vessel among pixels included in the synovial thickening 6, which is the region of interest. An inflammation score is given by Expression 4 as a value obtained by dividing the area (PDx) occupied by pixels of the region specified as a new blood vessel by the area (PDy) occupied by the region of interest.

$$PD = \frac{PDx}{PDy} \quad \text{[Expression 4]}$$

At this time, by setting an image portion composed of a part of the synovial thickening 6 (for example, a rectangular fixed-size image portion) as a region of interest from a bone detection result, the area (PDy) of the region of interest and the area (PDx) of the region specified as a new blood vessel in the region of interest may be calculated. In this case, the area (PDy) is a fixed value.

Thus, degree of disease can be evaluated more accurately by distinguishing existing blood vessels and new blood vessels, and calculating inflammation score (PD) by using only a region specified as being a new blood vessel.

When calculation of inflammation score (PD) is complete, the inflammation quantifier 2003B outputs the inflammation score to the storage 1020 (see FIG. 2), which the storage 1020 stores (step S1004 in FIG. 6).

According to the configuration above, a disease score that quantifies degree of disease can be calculated for each evaluation object frame from object image portion signals in B-mode image signals and Doppler mode image signals of evaluation object frames, and it is possible to improve objectivity in evaluating degree of disease.

(8) Selection of Representative Disease Score and Representative Disease Frame

In step S1009 in the flow of FIG. 6, the representative disease frame selector 2004 (see FIG. 3) uses disease scores stored in the storage 1020 (see FIG. 2) as input, selects one or more representative disease scores based on predefined numerical processing, and selects a frame corresponding to the representative disease score as a representative disease frame. The representative disease frame selector 2004 outputs a selected representative disease score and representative disease frame to the storage 1020, which the storage 1020 stores.

According to the present embodiment, the representative disease frame selector 2004 selects a maximum disease score stored in the storage 1020 as a representative disease score, and selects the frame indicating the representative disease score as a representative disease frame. However, the present invention is not limited thereto, and an average disease score indicating a mean degree of disease or a median disease score indicating a median degree of disease may be selected as a representative disease score.

When a representative disease score is a mean value or median value and there is no disease score matching the numerical value, a disease score closest to the numerical value is selected as the representative disease score and a frame indicating the closest disease score is selected as the representative disease frame.

Thus, selection criterion of a representative disease score can be appropriately set based on various conditions such as examination guidelines according to doctors and hospitals, disease conditions, subject characteristics, and the like.

Further, a configuration may have a plurality of selection criteria based on predefined numerical processing, and select one selection criterion from the plurality of selection criteria for use in diagnosis according to various conditions such as disease state, subject characteristics, and the like. In this case, selection criteria used to select a representative disease score are preferably stored in the storage 1020. This makes it possible to select a representative disease score using the same selection criteria as a disease score calculated in the past, and to compare a past evaluation result with follow-up observation such as periodical examination.

When correcting disease score, correction information is acquired from the operator via the input receiver 1009 and stored in the storage 1020. When there is an error in an image region determined to be a joint capsule or an image region determined to be a Doppler signal and the error is corrected, the disease score is recalculated in the morphometric quantifier 2003A and the inflammation quantifier 2003B, based on the corrected information. Further, a representative disease score is re-selected based on the recalculated disease score.

2. Display Screen According to Ultrasound Diagnostic Device 1100

(1) Operation Screen

The following describes an operation screen of the ultrasound diagnostic device 1100. The operation screen is displayed on the display 1008 according to instruction from the display controller 1016. According to the present embodiment, the display 1008 includes a touch panel display, and input to the ultrasound diagnostic device 1100 can be performed via the touch panel. That is, the display 1008 also functions as the input receiver 1009.

Figure 23:
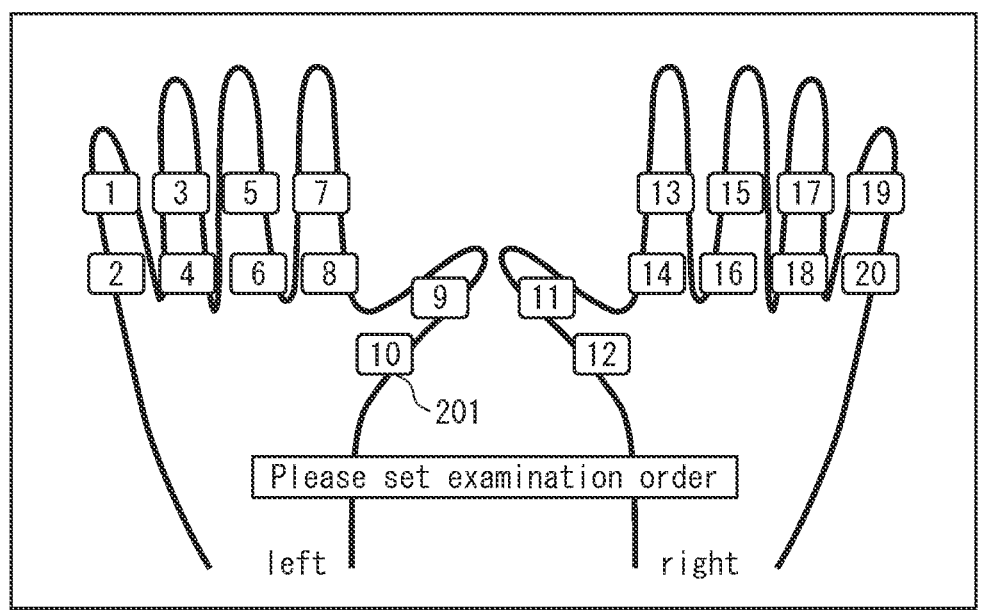
FIG. 23 shows an example of an input screen for recording an examination order.

Prior to examination, an operator registers an examination order of finger joints. FIG. 23 shows an example of an operation input screen of the ultrasound diagnostic device 1100 for registering examination order. When an operator touches icons 201 indicating joint positions, the icons 201 display numbers in the order touched. The numbers are registered as an examination order of corresponding joints (diagnostic sites). Further, when changing a registered examination order, when the icons 201 are displaying numbers indicating the examination order, if the icons 201 are touched again, the order of the second touches may be re-registered as the examination order.

The following describes an operation screen of the ultrasound diagnostic device 1100 in examination of one finger joint.

FIG. 24 shows an example of a display screen prior to starting ultrasound measurement. As shown in FIG. 24, the display screen includes a B-mode image portion 101, a Doppler mode image portion 102, a swelling score display portion 103, an inflammation score display portion 104, a representative swelling score information image portion 105, a representative inflammation score information image portion 106, a message display portion 107, and a frame number display portion 108. The display screen further includes a swelling time series display portion 110, an inflammation time series display portion 120, a swelling angle disease information display portion 130, an inflammation angle disease information display portion 140, an examination button portion 150, a diagnostic site display portion 160, and an operation button portion 170.

The operation button portion 150 includes a START button 151, a STOP button 152, and a RETRY button 153. The START button 151 is a button for starting or restarting ultrasound measurement, and the STOP button 152 is for stopping or interrupting ultrasound measurement. The RETRY button 153 is a button for retrying ultrasound measurement. For example, when a warning message (described later) is displayed in the message display portion 107 during ultrasound measurement, and when a warning state cannot be immediately resolved and measurement is to be retried, if the RETRY button 153 is touched, measurement can be restarted from the beginning. This procedure may require touching the STOP button 152 to stop measurement, followed by the RETRY button 153.

The diagnostic display region 160 includes a subject icon 161 schematically representing an exterior shape of the subject, diagnostic site icons 162 indicating locations of registered diagnostic sites of the subject, a measurement diagnostic site icon 163 indicating a location of a diagnostic site being measured, a next button 164 for selecting and displaying the next diagnostic site in the registered order, a return button 165 for selecting and displaying the immediately preceding diagnostic site in the registered order, and an order display portion that indicates the number of the currently displayed diagnostic site (currently being measured) in the registered order.

In the present embodiment, as shown in FIG. 24, the measurement diagnostic site icon 163 is larger than each of the diagnostic site icons 162. However, the present invention is not limited thereto, and it suffices that the measurement diagnostic site icon 163 and the diagnostic site icons 162 can be distinguished, such as by different display colors.

Further, according to the present embodiment, as shown in FIG. 24, the diagnostic site icons 162 are displayed as solid filled circles for diagnostic sites that have been measured, and hollow circles for diagnostic sites that have not yet been measured. However, the present invention is not limited thereto, and it suffices that measured and unmeasured sites can be distinguished from each other. For example, a configuration may be used in which measured diagnostic sites and unmeasured diagnostic sites are displayed in mutually different colors.

Figure 25:
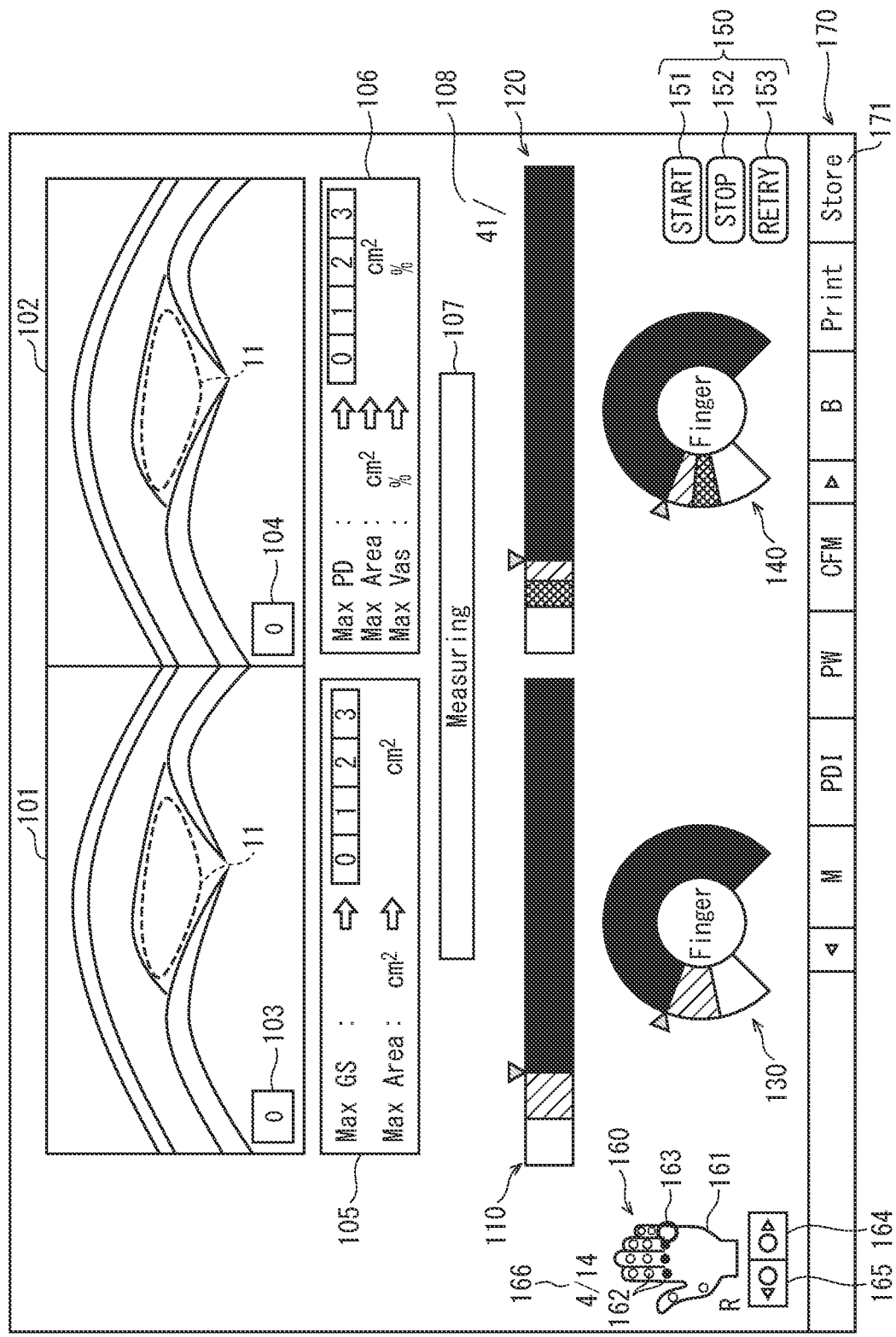
FIG. 25 shows an example of a display screen during ultrasound measurement.

In the state shown in FIG. 24, when an operator presses the START button 151, the flow of FIG. 6 starts and the display screen during measurement shown in FIG. 25 is displayed on the display 1008 (see FIG. 1, FIG. 2). Further, at this time, a message indicating that measurement is underway is displayed in the message display portion 107 of the display screen. A B-mode image is displayed in real-time in the B-mode image portion 101 and a Doppler mode image is displayed in real-time in the Doppler mode image portion 102. Further, in each image, the joint capsule boundary 11 detected by the diagnostic device is superimposed and displayed.

Figure 26:
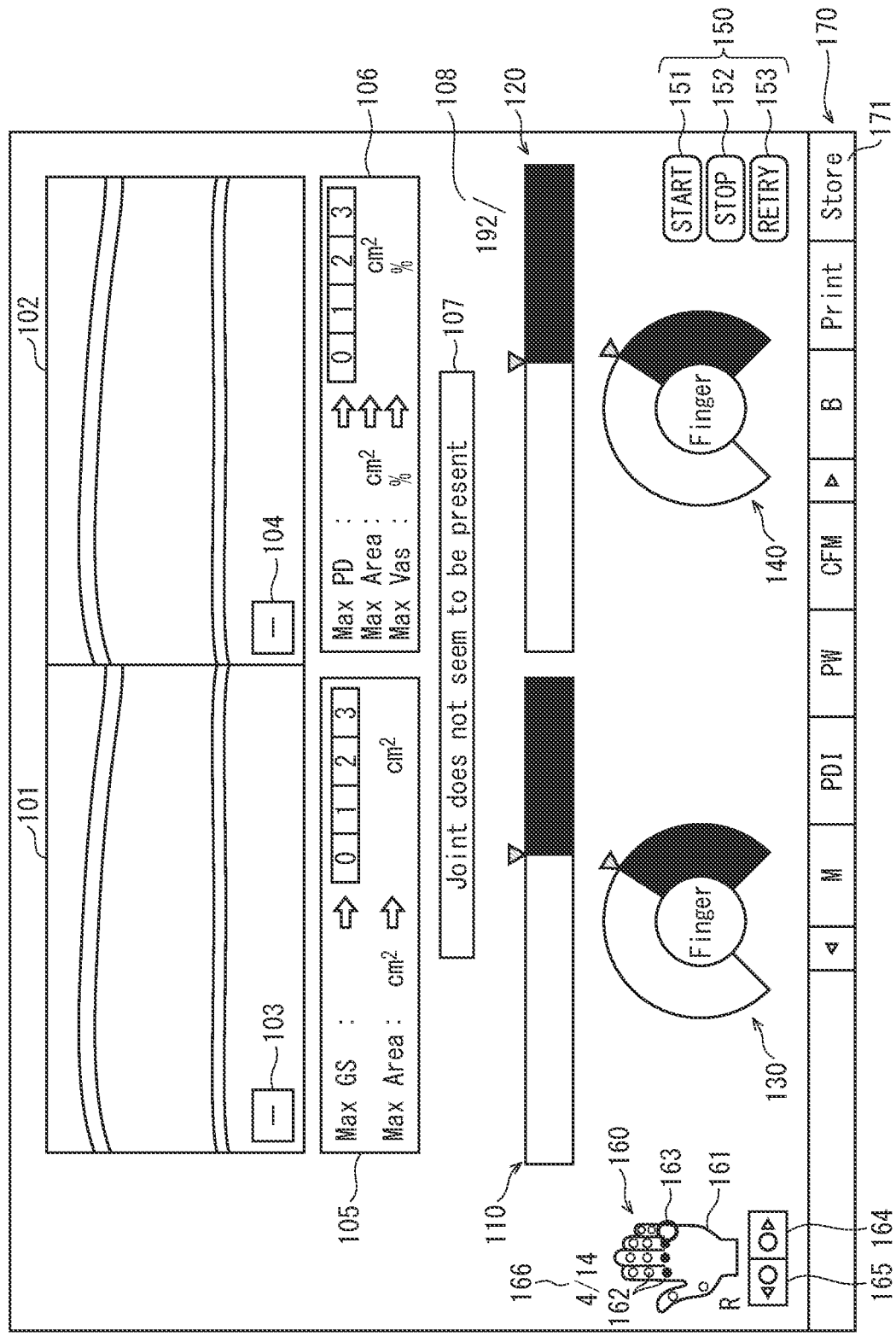
FIG. 26 shows an example of a display screen in which a warning message is displayed indicating that a joint is not included in an ultrasound image.
Figure 27:
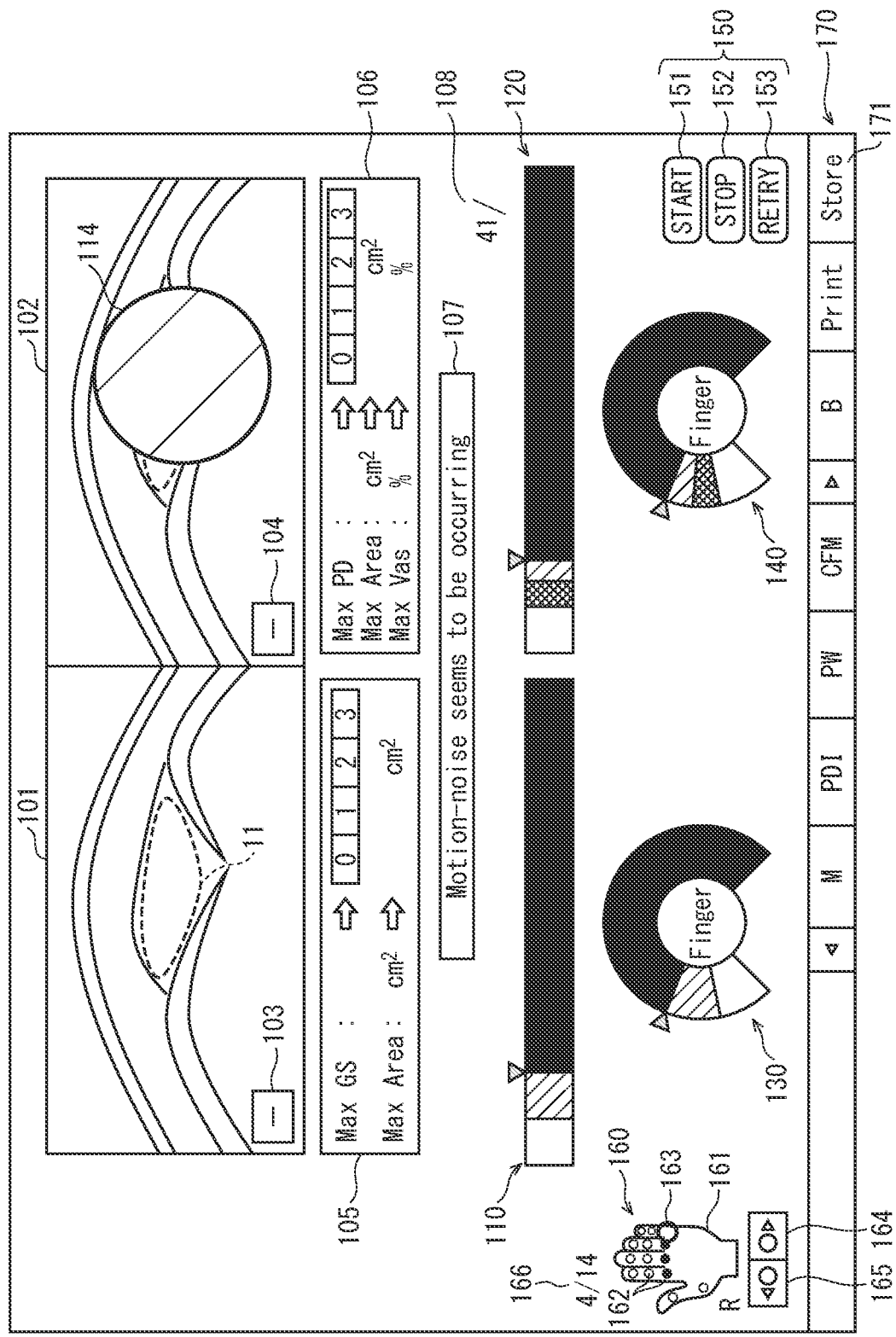
FIG. 27 shows an example of a display screen in which a warning message is displayed indicating that motion-noise is included in a Doppler-mode image.
Figure 28:
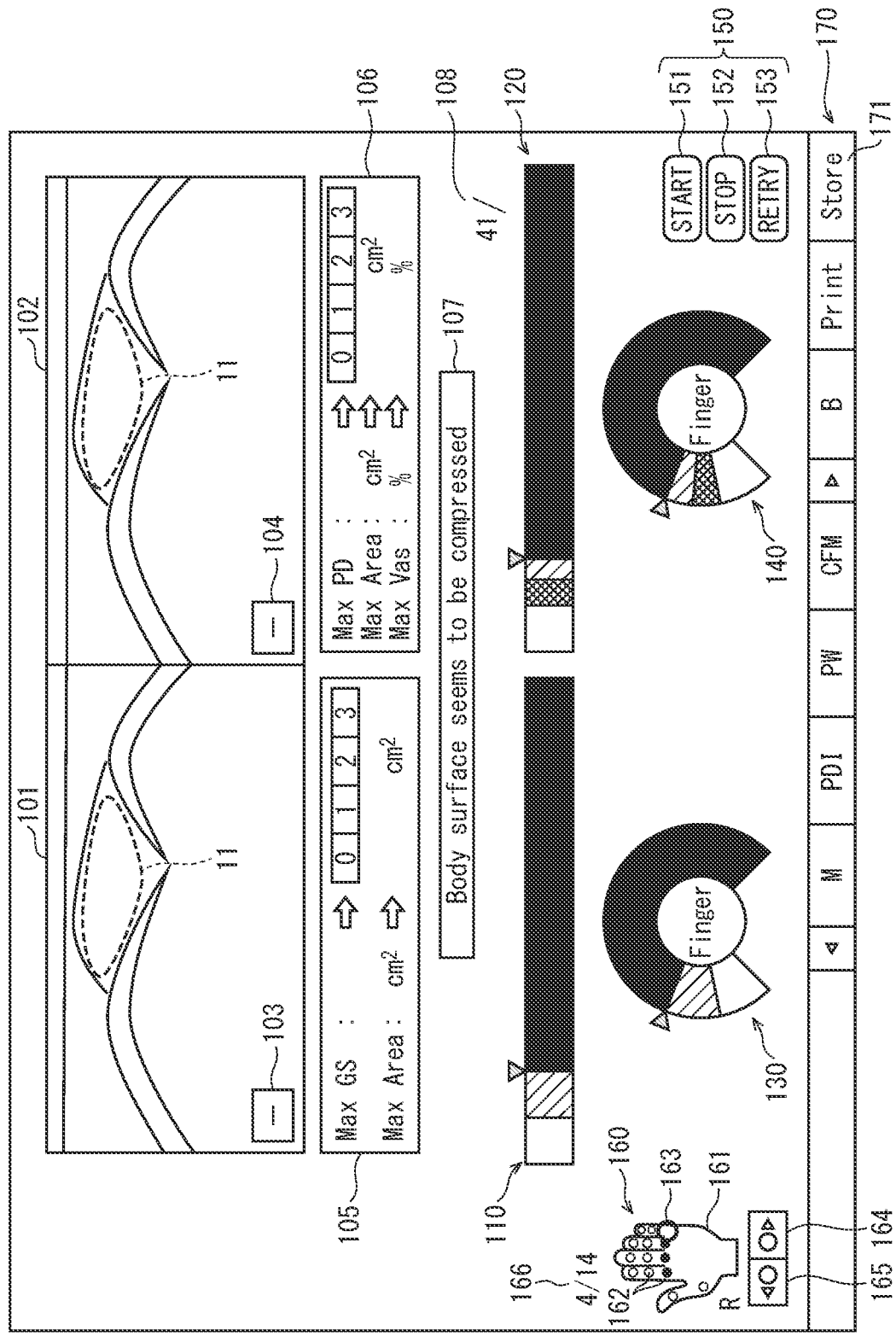
FIG. 28 shows an example of a display screen in which a warning message is displayed indicating that an ultrasound probe is compressing a subject's body surface.

In step S1001 of the flow of FIG. 6, when it is determined that a diagnostic site is not included in an ultrasound image ("No" at step S1001), a warning message indicating that a joint is not included in an ultrasound image is displayed in the message display portion 107, as shown in FIG. 26 (step S1006). Further, in step S1002 of the flow of FIG. 6, when it is determined that a portion caused by motion-noise is included in a Doppler mode image ("Yes" at step S1002), a warning message indicating that motion-noise is included is displayed in the message display portion 107, as shown in FIG. 27 (step S1007). In the step S1003 of the flow of FIG. 6, when it is determined that the ultrasound probe 1001a (see FIG. 2) is compressing the body surface of the subject ("Yes" at step S1003), a warning message indicating that a body surface is being compressed is displayed in the message display portion 107, as shown in FIG. 28. When such a warning message is displayed, the operator can adjust the probe unit 1001 appropriately, by adjusting position or orientation of the probe, or proximity to the body surface of the subject, in order to continue measurement. Alternatively, the operator may press the STOP button 152 to stop measurement, and, after adjusting the probe unit 1001, press the RETRY button 153 to restart measurement.

(2) Diagnostic Image

Figure 29:
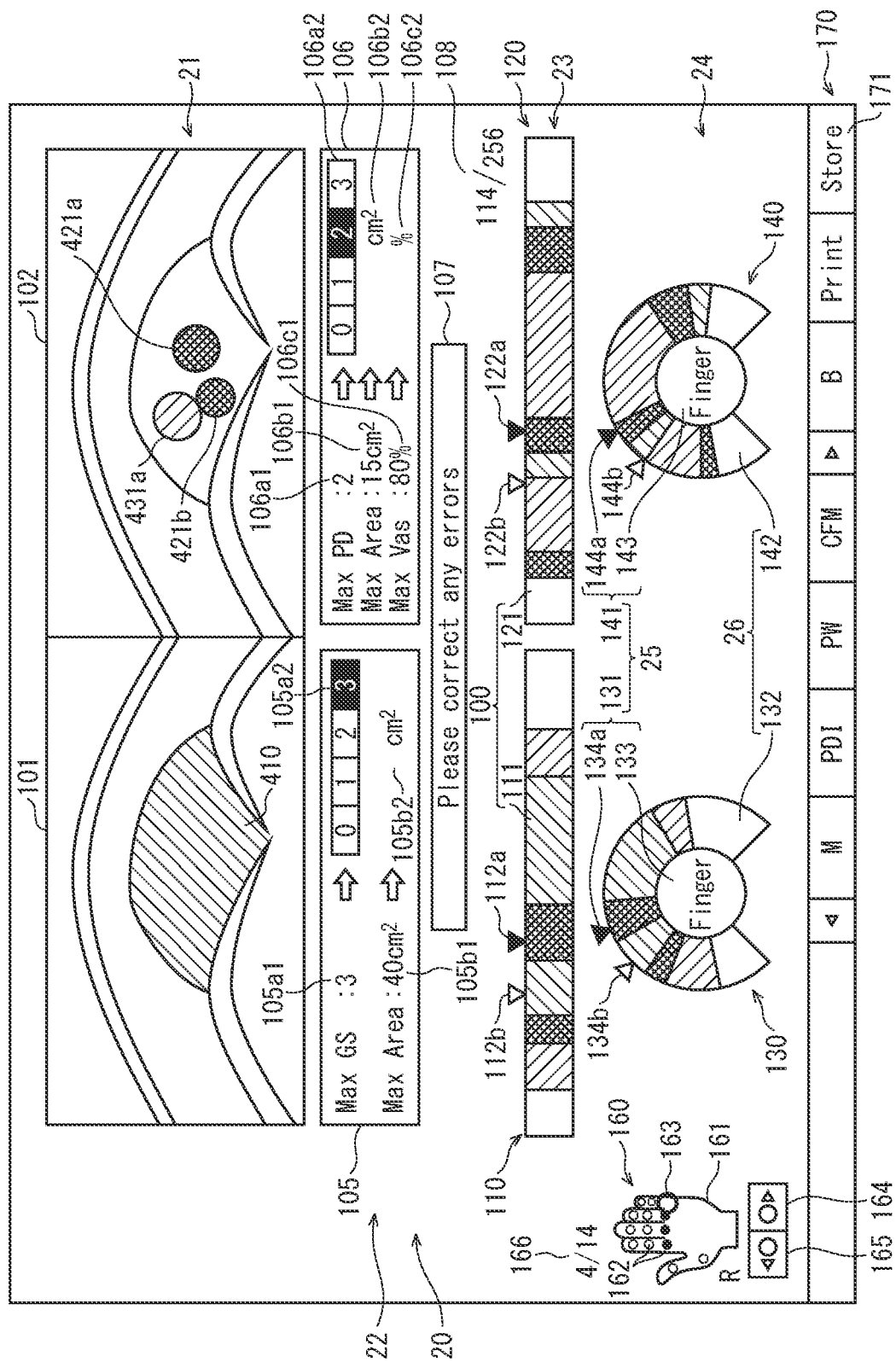
FIG. 29 shows an example of a diagnostic image corresponding to a representative disease frame.

FIG. 29 shows one example of a diagnostic image of a diagnostic site (joint), displayed on the display 1008 (see FIG. 1 and FIG. 2) after measurement of the diagnostic site is completed normally. The diagnostic image includes a disease activity information indicator 20 and an ultrasound image portion 21. The ultrasound image portion 21 includes the B-mode image portion 101 and the Doppler mode image portion 102, the B-mode image portion 101 showing a B-mode image and the Doppler mode image portion 102 showing a Doppler mode image. In a diagnostic image displayed after measurement for one diagnostic site (joint) is normally completed, ultrasound images (B-mode image and Doppler mode image) of a representative disease frame of the diagnostic site are displayed in the ultrasound image portion 21.

As shown in FIG. 29, a synovial thickening region 410 is shown in the B-mode image displayed in the B-mode image portion 101. Further, new blood vessels 421 (421*a*, 421*b*) and a possible new blood vessel 431 (431*a*) are shown in the Doppler mode image displayed in the Doppler mode image portion 102.

The disease activity information indicator 20 includes a disease score information image portion 22, an angle disease information image portion 26, and a bar 100. The disease activity information indicator 20 is not limited to a configuration including all of the disease score information image portion 22, the angle disease information image portion 26, and the bar 100, and may be configured to include only one or two of these.

The disease score information image portion 22 is an image portion displaying information representing a disease score. Information representing a disease score may be a disease score (numerical value), or may be an image visually representing a disease score such as a bar graph or a pie chart. Further, based on the disease score, one or more of color, lightness, saturation, and pattern may indicate different degrees of disease. The disease score information image portion 22 includes a representative swelling score information image portion 105 and a representative inflammation score information image portion 106.

Information representing a representative swelling score (in the present embodiment, a maximum swelling score (Max GS)) calculated for the diagnostic site is displayed in a pre-correction maximum swelling score information image portion 105*a*1 of the representative swelling score information image portion 105. A maximum synovial thickening region area (Max Area), which is a maximum value of area of a region determined to be the synovial thickening region 410 in the diagnostic site, is displayed in a pre-correction maximum synovial thickening region area display portion 105*b*1. The greater the degree of synovial thickening and synovial fluid retention, the larger the synovial thickening region, and therefore the area of the portion determined to be the synovial thickening region 410 increases.

Information representing a representative inflammation score (in the present embodiment, a maximum inflammation score (Max PD)) calculated for the diagnostic site is displayed in a pre-correction inflammation score information image portion 106*a*1 of the representative inflammation score information image portion 106. A maximum area of a region determined to be a new blood vessel 421 in the diagnostic site (Max Area) is displayed in a pre-correction new blood vessel maximum area display portion 106*b*1. As rheumatism advances, new blood vessels occur in greater numbers and increase in size, and therefore a total area of new blood vessels (and possible new blood vessels) increases. A maximum vascularity (Max Vas) calculated in the diagnostic site is displayed in a pre-correction maximum vascularity display portion 106*c*1. Here, vascularity, from the meaning of vascular distribution, is used to mean a ratio (occupancy rate) occupied by a blood flow region.

Bars 100 are included in a time series disease information display portion 23. The time series disease information display portion 23 includes a swelling time series display portion 110 and an inflammation time series display portion 120. The swelling time series display portion 110 includes a bar 111 and the inflammation time series display portion 120 includes a bar 121. The bars 100 includes the bar 111 and the bar 121.

The swelling time series display portion 110 includes the bar 111, which is rectangular, and a time sequence indicator 112*a*, which is triangular. The bar 111 represents an entire sequence of frames of ultrasound diagnostic images acquired in measurement of one diagnostic site. The time sequence indicator 112*a* indicates a position of a representative disease frame in the sequence. In the example shown in FIG. 29, as shown in the frame number display portion 108, the total number of frames in the sequence is 256 and a representative disease frame is the 114th frame in the sequence. Accordingly, the bar 111 represents 256 frames, and the time sequence indicator 112*a* indicates a position corresponding to the 114th frame therein.

Further, a time sequence indicator 112*b* indicates a position corresponding to a representative disease frame previously measured (hereinafter, "previous representative disease frame").

At positions corresponding to each frame in the bar 111, swelling scores of each frame are indicated by differences in at least one of color, lightness, saturation, and pattern. According to the present embodiment, as shown in FIG. 29, swelling scores are divided into four steps, each being indicated by a different pattern (including no pattern). That is, the bar 111 represents the number of frames in the entire sequence, and represents time sequence swelling information indicating changes in swelling score in the sequence.

The inflammation time sequence display portion 120 is configured similarly to the swelling time sequence display portion 110 and has the bar 121, which is rectangular, and a time sequence indicator 122*a*, which is triangular. The bar 121 represents the entire sequence, and the time sequence indicator 122*a* indicates a position of a representative disease frame therein. Further, at positions corresponding to each frame in the bar 121, inflammation scores of each frame are indicated by differences in at least one of color, lightness, saturation, and pattern.

According to the present embodiment, as shown in FIG. 29, inflammation scores are divided into four steps, each being indicated by a different pattern (including no pattern). That is, the bar 121 represents the number of frames in the entire sequence, and represents time sequence inflammation information indicating changes in inflammation score in the sequence.

The bars 100 are not limited to the configurations of the bar 111 and the bar 121, and may be a single bar, or may include another bar indicating information representing a degree of disease other than swelling score and inflammation score. Further, without separating swelling score information and inflammation score information, as information collectively representing a degree of disease, the bars 100 may be treated generically as an image portion representing time series disease degree information indicating changes in degree of disease in the sequence.

The time series indicators 112*a*, 112*b*, 122*a*, 122*b* do not indicate degrees of disease, and therefore the disease activity information indicator 20 includes the bar 111 and the bar 121 and does not include the time series indicators 112a, 112b, 122a, 122b.

Further, shape of the time series indicators 112a, 112b, 122a, 122b is not limited to being triangular, and may be any shape, such as a straight line, arrow, circle, or diamond.

Further, when it is not necessary to distinguish between time series swelling information and time series inflammation information, they are collectively referred to as "time series disease information".

An angle disease information display portion 24 includes a swelling angle disease information display portion 130 and an inflammation angle disease information display portion 140.

The swelling angle disease information display portion 130 includes a swelling angle information image portion 131 and a swelling angle disease information image portion 132.

The swelling angle information image portion 131 includes a subject cross-section icon 133 and an angle indicator 134a. The subject cross-section icon 133 is an icon image that schematically represents a cross-section of the subject in a virtual plane orthogonal to a longitudinal direction of the long subject and passing through the diagnostic site. The angle indicator 134a is a triangular image indicating an angle of the ultrasound probe 1001a (see FIG. 2) relative to the diagnostic site. According to the present embodiment, the cross-section is a section of a finger joint, and represented by a circle. Further, the angle indicator 134a indicates angle information corresponding to a representative disease frame. That is, an angle of the ultrasound probe 1001a relative to the subject when the ultrasound image signal of the representative disease frame is acquired is indicated by a position corresponding to the subject cross-section icon 133. An angle indicator 134b indicates angle information corresponding to the previous representative disease frame.

The swelling angle disease information image portion 132 is configured to indicate the swelling score of a frame of a corresponding angle by differences in at least one of color, lightness, saturation, and pattern, in a border portion around the subject cross-section icon 133. According to the present embodiment, as shown in FIG. 29, swelling scores are divided into four steps, each being indicated by a different pattern (including no pattern). That is, the swelling angle disease information image portion 132 represents a number of frames of the sequence by size of a sector, and also represents angle swelling information that indicates changes in swelling score in the sequence in association with angle.

The angle indicator 134a is positioned outside the swelling angle disease information image portion 132. Further, the swelling angle disease information image portion 132 may entirely surround the subject cross-section icon 133, but need not do so. According to the present embodiment, as shown in FIG. 29, a portion below the subject cross-section icon 133 is not surrounded by the swelling angle disease information image portion 132. Hereinafter, reference to "around" or "surrounding" the subject cross-section icon 133 does not necessarily mean completely surrounding the subject cross-section icon 133.

The inflammation angle disease information display portion 140 includes an inflammation angle information image portion 141 and an inflammation angle disease information image portion 142.

The inflammation angle information image portion 141 includes a subject cross-section icon 143 and an angle indicator 144a. The subject cross-section icon 143 is an icon image that schematically represents a cross-section of the subject, similar to the subject cross-section icon 133. The angle indicator 144a is a triangular image indicating an angle of the ultrasound probe 1001a (see FIG. 2) relative to the diagnostic site, similar to the angle indicator 134a. The angle indicator 144a indicates angle information corresponding to the representative disease frame and the angle indicator 144b indicates angle information corresponding to the previous representative disease frame.

The inflammation angle disease information image portion 142 is configured to indicate the inflammation score of a frame of a corresponding angle by differences in at least one of color, lightness, saturation, and pattern, in a border portion around the subject cross-section icon 143, similarly to the swelling angle disease information image portion 132. According to the present embodiment, as shown in FIG. 29, inflammation scores are divided into four steps, each being indicated by a different pattern (including no pattern). That is, the inflammation angle disease information image portion 142 represents a number of frames of the sequence by size of a sector, and also represents angle inflammation information that indicates changes in inflammation score in the sequence in association with angle.

The angle indicator 144a is positioned outside the inflammation angle disease information image portion 142.

Further, the angle information image portion 25 is composed of the swelling angle information image portion 131 and the inflammation angle information image portion 141. The angle disease information image portion 26 is composed of the swelling angle disease information image portion 132 and the inflammation angle disease information image portion 142.

When there is no particular need to distinguish between angle swelling information representing changes in swelling score across angles and angle inflammation information representing changes in inflammation score across angles, they are collectively referred to as "angle disease information".

Figure 30:
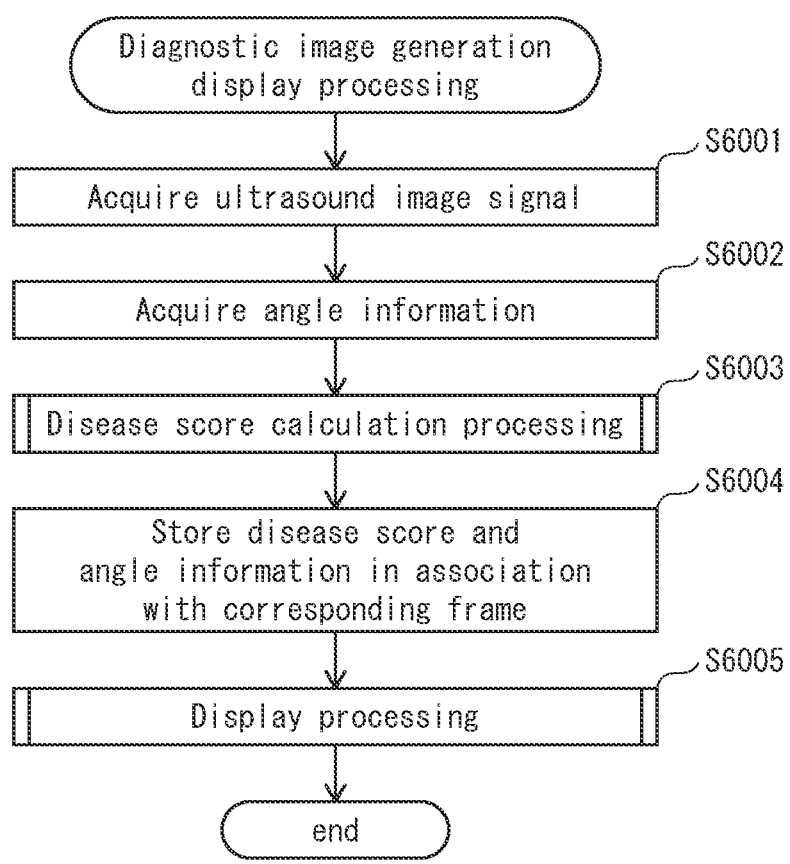
FIG. 30 is a flowchart showing diagnostic image generation display processing.

To continue, the controller 1010 generates a diagnostic image based on a plurality of ultrasound image signal frames acquired via the ultrasound probe 1001a and makes this be displayed on the display 1008. A description of this processing is provided below, with reference to a flowchart. FIG. 30 is a flowchart showing an example of diagnostic image generation display processing. In a main routine (not illustrated) controlling the ultrasound diagnostic device 1100, each time a subroutine of diagnostic image generation display processing is called, the subroutine is executed. According to the present embodiment, when it is determined that measurement for one finger joint (diagnostic site) is completed in step S1005 of the flow in FIG. 6, the subroutine of diagnostic image generation display is called.

First, ultrasound image signals stored in the storage 1020 are acquired (step S6001).

Subsequently, angle information stored in the storage 1020 is acquired (step S6002).

Subsequently, the disease score calculation processing shown in FIG. 6 is executed, based on the ultrasound image signals acquired (step S6003).

Subsequently, calculated disease scores and acquired angle information are associated with corresponding frames and stored in the storage 1020 (step S6004). For example, a frame ID of a corresponding frame is associated with a disease score and angle information and stored in the storage 1020. According to the present embodiment the frame ID is a frame number, but any ID information may be used as the frame ID.

Subsequently, display processing is executed (step S6005). Details of display processing are described below.

Figure 31:
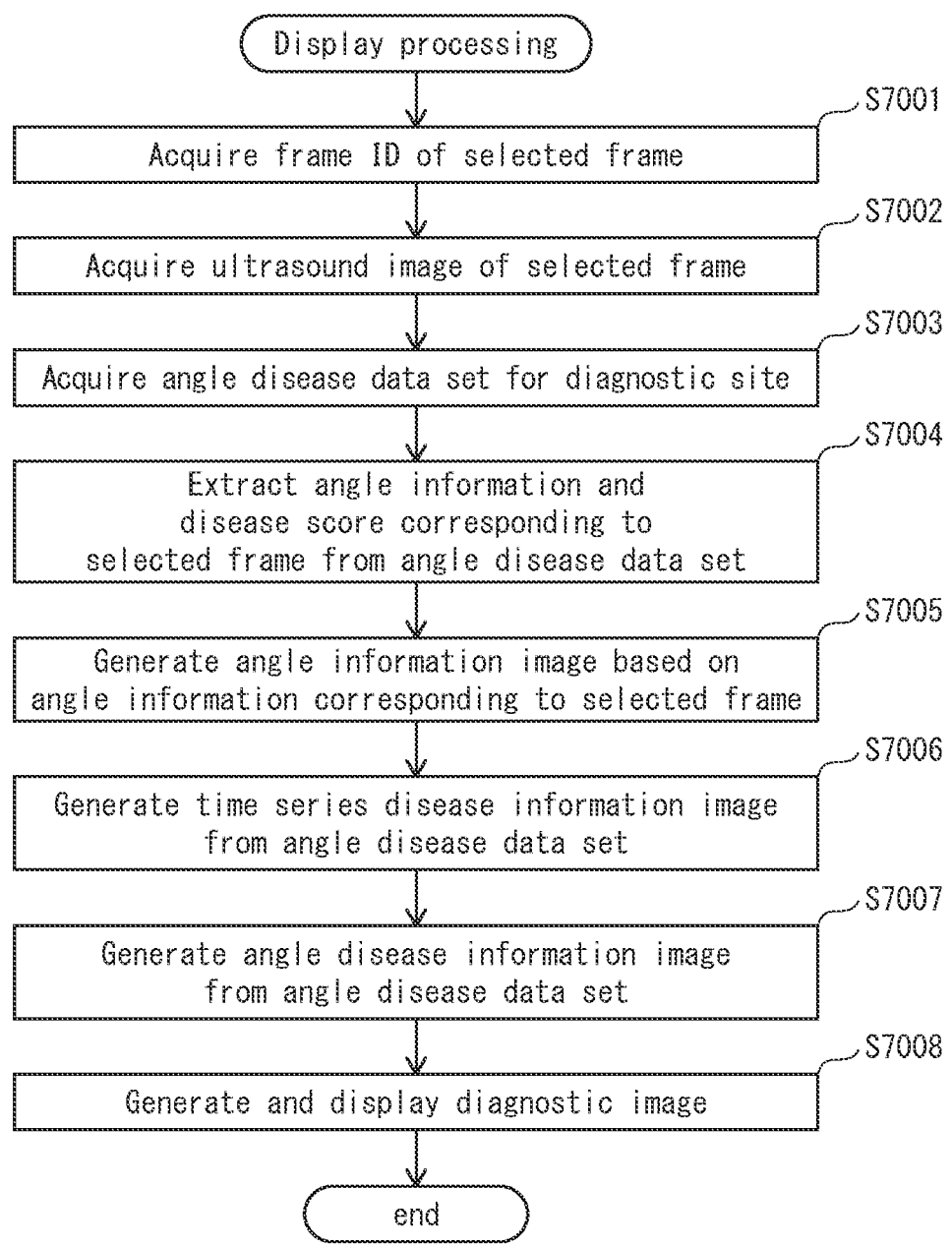
FIG. 31 is a flowchart showing display processing.

FIG. 31 is a flowchart showing the display processing of step S6005 in the flow of FIG. 30.

First, a frame ID of a selected frame is acquired (step S7001). The selected frame here means a representative disease frame.

Subsequently, an ultrasound image of the selected frame is acquired from the storage 1020 (step S7002).

Subsequently, an angle disease data set regarding a diagnostic site that is an object of the display processing is acquired (step S7003). Here, the angle disease data set is a set of all disease scores and angle information (associated with each other for each frame) acquired for one diagnostic site, stored in the storage 1020 for each diagnostic site. Ultrasound images may be included in an angle disease data set, and in such a case, the ultrasound images, disease scores, and angle information are associated with each other for each frame.

Subsequently, angle information and disease score corresponding to the selected frame are extracted from the acquired angle disease data set. The disease score corresponding to the selected frame here means the representative disease score.

Subsequently, an angle information image is generated based on the angle information corresponding to the selected frame (step S7005).

Subsequently, a time sequence disease information image is generated from the angle disease data set (step S7006).

Further, an angle disease information image is generated from the angle disease data set (step S7007).

Subsequently, a diagnostic image is generated that includes an ultrasound image, a representative disease score, an angle information image, a time sequence disease information image, and an angle disease information image, and displayed on the display 1008 (see FIG. 1, FIG. 2) (step S7008).

Note that the flows shown in FIG. 30 and FIG. 31 indicate examples of diagnostic image generation display processing and display processing, but the present invention is not necessarily limited to these examples. For example, in the flow of diagnostic image generation display processing shown in FIG. 30, step S6002 may be after step S6003. Further, for example, in the flow of the display processing shown in FIG. 31, step S7001, step S7002, step S7004, and step S7005 may be after step S7003, step S7006, and step S7007.

(3) Correction

A message prompting correction is displayed in the message display portion 107 when correction is required for any of the synovial thickening region 410 displayed in the B-mode image portion 101, a new blood vessel or possible new blood vessel displayed in the Doppler mode image portion 102, a representative swelling score displayed in the representative swelling score information image portion 105, and a representative inflammation score displayed in the representative inflammation score information image portion 106.

Methods of correcting representative swelling score and representative inflammation score are described below with reference to FIG. 32 to FIG. 35.

Figure 32:
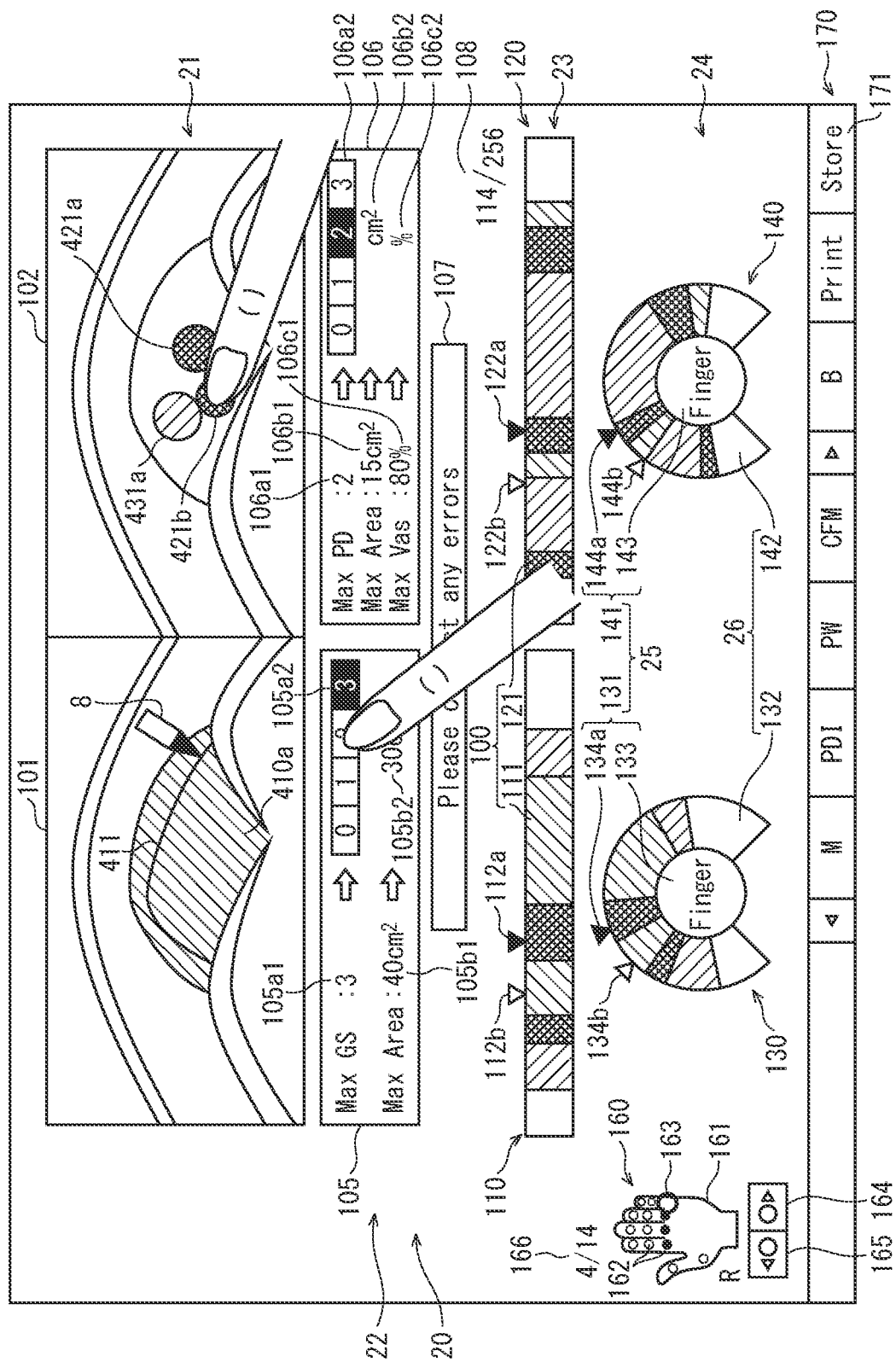
FIG. 32 shows an example of a display image during a correction operation, in order to describe a disease score correction operation.
Figure 33:
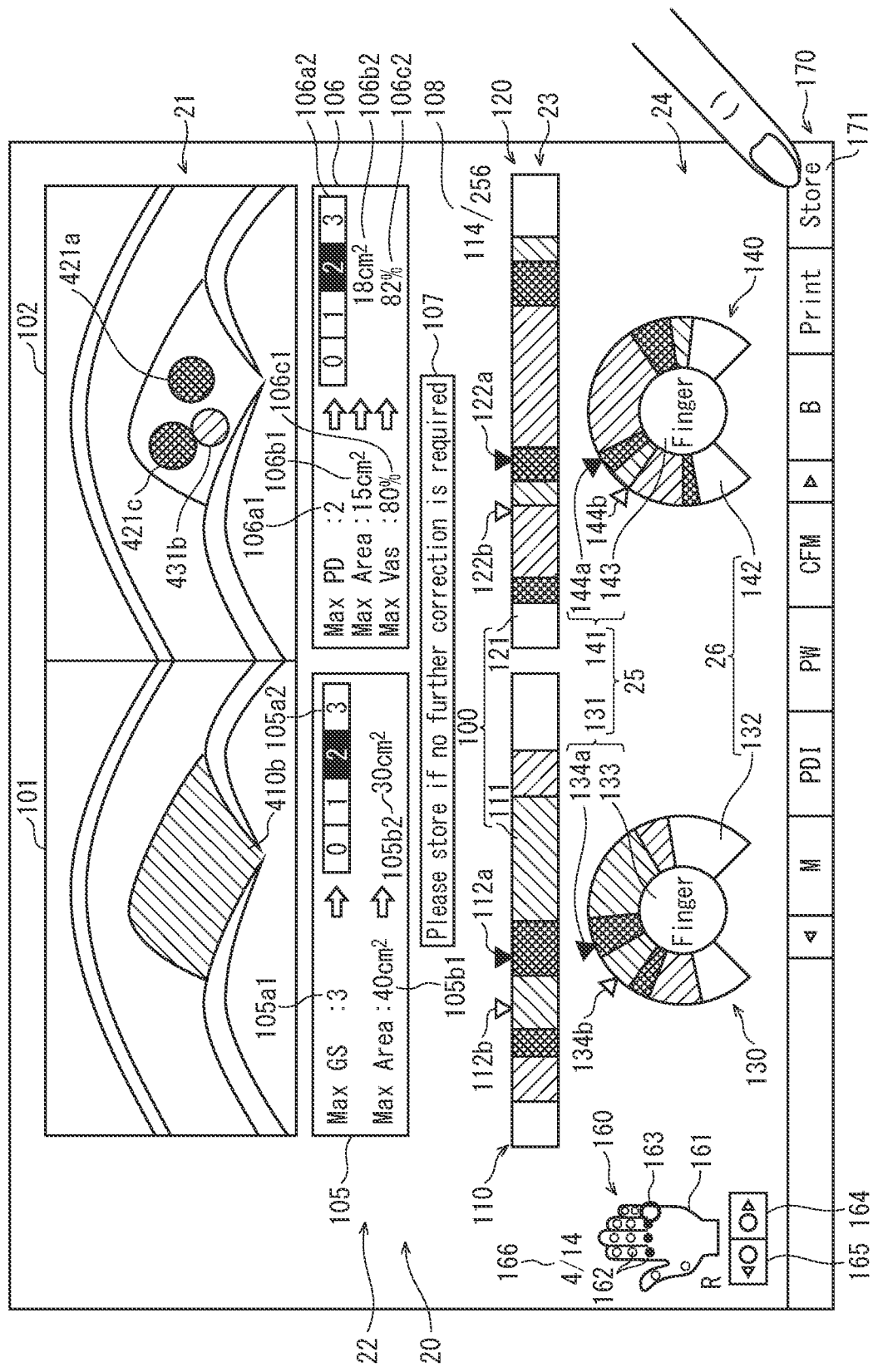
FIG. 33 shows an example of a display image during a correction operation, in order to describe a disease score correction operation.

First, a method of correcting representative swelling score is described. According to the ultrasound diagnostic device 1100 pertaining to the present embodiment, when a portion determined to be the synovial thickening region 410 is too large or too small in the B-mode image displayed in the B-mode image portion 101, a corrected range of the synovial thickening region 410 can be designated by drawing on the touch panel by using a touch pen 8. For example, as shown in FIG. 32, when a synovial thickening region 410a prior to correction is too large, a correct synovial thickening region range is designated by drawing on the touch panel by using the touch pen 8. Thus, as shown in FIG. 33, a synovial thickening region 410b after correction is displayed.

Further, area of the synovial thickening region 410b is automatically recalculated, and a value of maximum synovial thickening region area after correction is displayed in a post-correction maximum synovial thickening region area display portion 105b2. Likewise, Max GS is recalculated, and Max GS after correction is displayed in a post-correction maximum swelling score information image portion 105a2.

Max GS may be manually corrected. For example, as shown in FIG. 32, when a Max GS prior to correction shown in the pre-correction maximum swelling score information image portion 105a1 is determined to be 3, but a correct Max GS is actually 2, touching the post-correction maximum swelling score information image portion 105a2 may highlight a numeral 2 displayed in the post-correction maximum swelling score information image portion 105a2 and correct Max GS to 2, as shown in FIG. 33.

Further, maximum synovial thickening region area can be manually corrected. For example, when a pre-correction maximum synovial thickening region area is 40 $cm^2$, and this is corrected to 30 $cm^2$, the present invention may be configured to allow numerical input by use of a numerical keypad after a touch operation on the post-correction maximum synovial thickening region area portion 105b2.

Further, an automatically corrected Max GS and maximum synovial thickening region area may also be manually correctable.

Note that Max GS may be correctable without correcting the synovial thickening region 410 in the B-mode image. In the case of such a configuration, a case in which an area of a synovial thickening region is large but an overall degree of disease is low can be handled.

The following describes methods of correcting representative inflammation score with reference to FIG. 32 to FIG. 35. First, two cases of correction of a Doppler mode image displayed in the Doppler mode image portion 102 are described, one in which a portion that is not a new blood vessel is mistakenly determined to be the new blood vessel 421, and one in which a portion that is the new blood vessel 421 is mistakenly determined to be the possible new blood vessel 431.

For example, as shown in FIG. 32, the new blood vessel 421a, the new blood vessel 421b, and the possible new blood vessel 431a are displayed in a diagnostic image, and a case is described in which the new blood vessel 421b is actually not a new blood vessel and the possible new blood vessel 431a is actually a new blood vessel. When the new blood vessel 421b is touched on the touch panel, the new blood vessel 421b is corrected to a possible new blood vessel and displayed as a possible new blood vessel 431b, as shown in FIG. 33. Further, when the possible new blood vessel 431a is touched on the touch panel, the possible new blood vessel 431a is corrected to a new blood vessel and displayed as a new blood vessel 421c.

Subsequently, post-correction values of Max PD, maximum new blood vessel area, and Max Vas are recalculated and displayed in a post-correction inflammation score information image portion 106a2, a post-correction maximum new blood vessel area display portion 106b2, and a post-correction maximum vascularity display portion 106c2, respectively.

Note that Max PD, maximum new blood vessel area, and Max Vas may each be manually correctable. Manual correction may be performed similarly to the methods of correcting the representative swelling score information image portion 105, Max GS, and maximum synovial thickening area.

Further, Max PD and Max Vas may be correctable without correcting the new blood vessel 421 or the possible new blood vessel 431 in the Doppler mode image portion 102.

Figure 34:
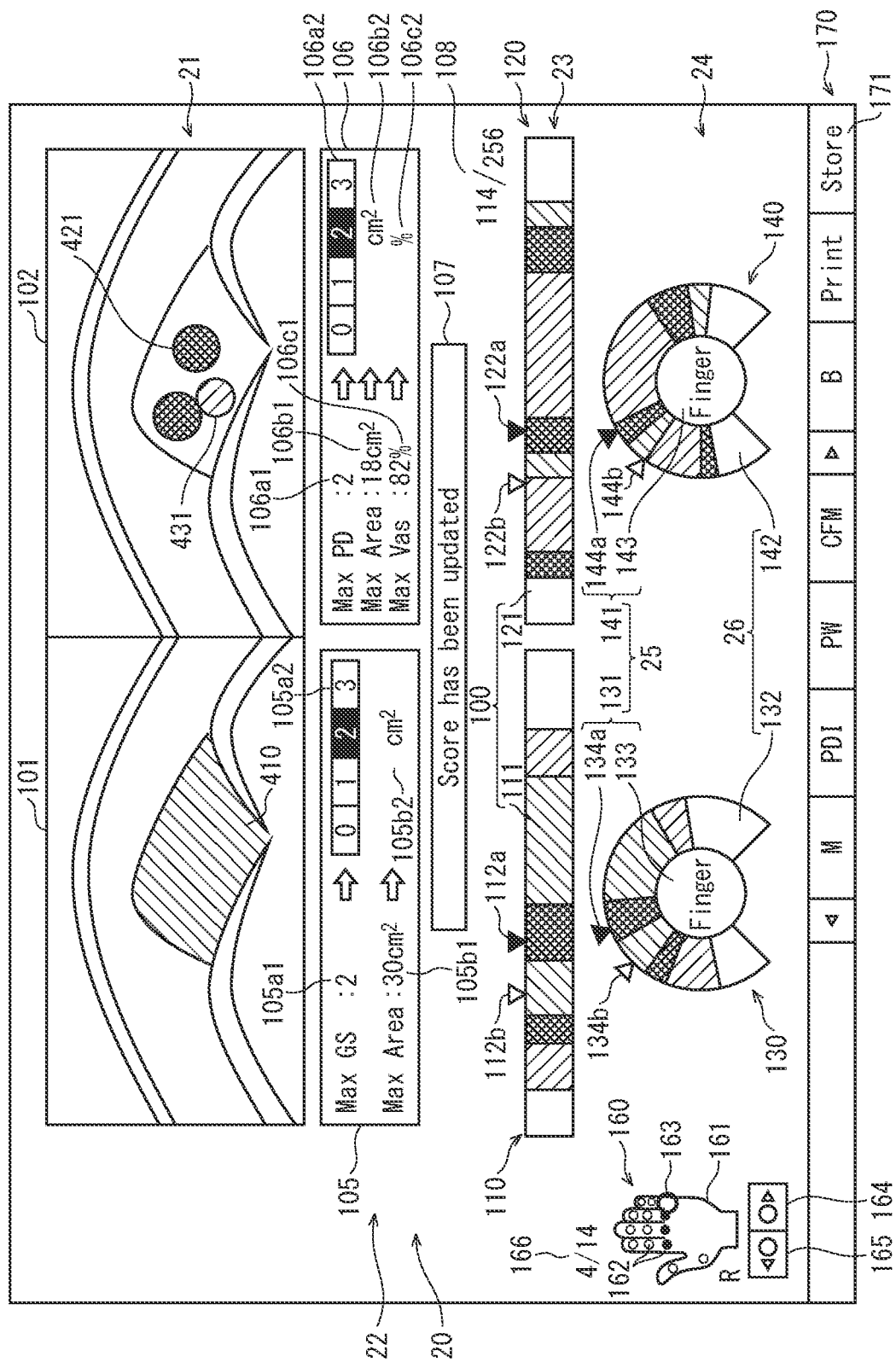
FIG. 34 shows an example of a display image after a disease score correction operation.

When any kind of correction is performed, a message is displayed in the message display portion 107 prompting saving of post-correction data if no further correction is required, as shown in FIG. 33. When all corrections are completed, a touch of a store button 171 of the operation button portion 170 stores post-correction data in the storage 1020 (see FIG. 2). When storing of post-correction data is completed, a message is displayed in the message display portion 107 indicating that storing of post-correction data is completed, as shown in FIG. 34.

Further, when manually selecting another frame as a representative disease frame instead of the frame selected as the representative disease frame, the time series indicator 112a is moved left or right along the bar 111. Accordingly, since a diagnostic image of the destination frame number is displayed, the time series indicator 112a may be stopped at a position of the frame to be manually selected as the representative disease frame. Subsequently, if Max GS, etc., is corrected, correction is performed, then, if the store button 171 is touched, a post-correction frame is stored in the storage 1020 as a representative disease frame and post-correction data is stored in the storage 1020 as disease data of the post-correction representative disease frame.

The time series indicator 112a, the time series indicator 122a, the angle indicator 134a, and the angle indicator 144a move together, and therefore another frame may be selected by moving any of these. In such a case, the angle indicator 134a and the angle indicator 144a can be moved around the periphery of the swelling angular disease information image portion 132 and the inflammation angular disease information image portion 142, respectively.

Further, the time series indicator 112b, the time series indicator 122b, the angle indicator 134b, and the angle indicator 144b, which each indicate position of the previous representative disease frame, can be used as guides when manually selecting a representative disease frame. Further, according to the angle indicator 134b and the angle indicator 144b it is easy to compare disease scores calculated from ultrasound images acquired at a same angle in follow-up observations in periodic examinations or the like.

Shape of the angle indicators 134a, 134b, 144a, 144b is not limited to being triangular, and may be any shape, such as a straight line, arrow, circle, or diamond.

Figure 35:
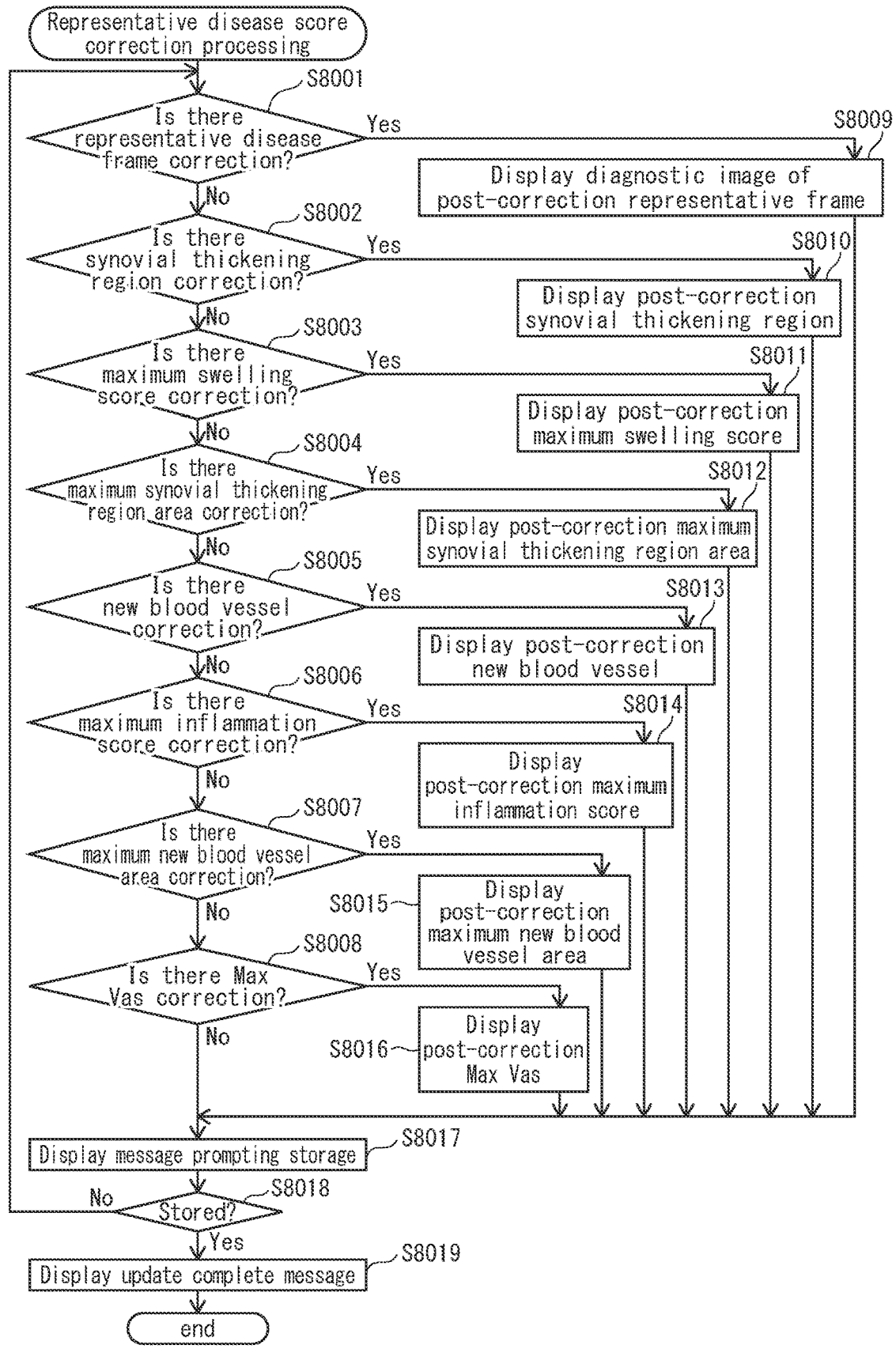
FIG. 35 is a flowchart showing representative disease score correction processing.

The following describes correction processing of representative disease score with reference to a flowchart. FIG. 35 is a flowchart indicating an example of representative disease score correction processing performed by the controller 1010.

First, it is determined whether or not correction of a representative disease frame is received (step S8001). More specifically, with respect to a frame selected as a representative disease frame by the representative disease frame selector 2004 (see FIG. 3), when an operator moves any one of the time series indicators 112a, 122a or the angle indicators 134a, 144a to select and cause display of a diagnostic image of a different frame, it is determined that correction of a representative disease frame is received.

When correction of a representative disease frame is received, a diagnostic image of a post-correction representative disease frame is displayed and a message prompting storing is displayed on the message display portion 107 ("Yes" at step S8001, step S8009, step S8017).

When correction of a representative disease frame is not received in step S8001, whether or not a synovial thickening region is corrected is determined ("No" at step S8001, step S8002). More specifically, it is determined whether or not the synovial thickening region 410 is corrected by the touch pen 8 on the touch panel.

When correction of synovial thickening region is received, a post-correction synovial thickening region is displayed and a message prompting storing is displayed ("Yes" at step S8002, step S8010, step S8017). Note that in display of post-correction synovial thickening region in step S8012, display of recalculation of post-correction disease score and display of recalculated disease score are also included.

When correction of synovial thickening region is not received in step S8002, whether or not correction of maximum swelling score is received is determined ("No" at step S8002, step S8003).

When correction of maximum swelling score is received, a post-correction maximum swelling score is displayed and a message prompting storing is displayed ("Yes" at step S8003, step S8011, step S8017).

When correction of maximum swelling score is not received, whether or not correction of maximum synovial thickening region area is received is determined ("No" at step S8003, step S8004).

When correction of maximum synovial thickening region area is received, a post-correction maximum synovial thickening region area is displayed and a message prompting storing is displayed ("Yes" at step S8004, step S8012, step S8017).

When correction of maximum synovial thickening region area is not received, whether or not correction of a new blood vessel is received is determined ("No" at step S8004, step S8005). More specifically, when an operator touches a new blood vessel or possible new blood vessel on the touch panel, it is determined that correction of a new blood vessel is received.

When correction of a new blood vessel is received, a post-correction new blood vessel is displayed and a message prompting storing is displayed ("Yes" at step S8005, step S8013, step S8017). In display of a post-correction new blood vessel, display of recalculation of a post-correction maximum inflammation score, new blood vessel area, and maximum vascularity, and recalculation results, are also included.

When correction of a new blood vessel is not received in step S8005, whether or not correction of maximum inflammation score is received is determined ("No" at step S8005, step S8006).

When correction of maximum inflammation score is received, a post-correction maximum inflammation score is displayed and a message prompting storing is displayed ("Yes" at step S8006, step S8014, step S8017).

When correction of maximum inflammation score is not received, whether or not correction of maximum new blood vessel area is received is determined ("No" at step S8006, step S8007).

When correction of maximum inflammation score is received, a post-correction maximum inflammation score is displayed and a message prompting storing is displayed ("Yes" at step S8007, step S8015, step S8017).

When correction of maximum new blood vessel area is not received, whether or not correction of maximum vascularity is received is determined ("No" at step S8007, step S8008).

When correction of maximum vascularity is received, a post-correction maximum vascularity is displayed and a message prompting storing is displayed ("Yes" at step S8008, step S8016, step S8017).

When correction of maximum vascularity is not received, a message prompting storing is displayed ("No" at step S8008, step S8017).

After a message prompting storing is displayed in step S8017, whether or not a storing instruction is received is determined (step S8017, step S8018). More specifically, when an operator touches the store button 171, it is determined that a storing instruction is received.

When a storing instruction is not received ("No" at step S8018), processing returns to step S8001 and whether or not correction of a representative frame is received is determined. Until reception of a storing instruction in step S8018 is received, steps S8001 to S8018 are repeated.

When a storing instruction is received, an update complete message is displayed ("Yes" at step S8018, step S8019) and processing ends.

In a main routine (not illustrated) controlling the ultrasound diagnostic device 1100, each time a subroutine of representative disease score correction processing is called, the subroutine is executed. According to the present embodiment, the subroutine of representative disease score correction processing is called by an operator performing a touch operation on the touch panel, with respect to the diagnostic image shown in FIG. 29. In this case, the subroutine of representative disease score correction processing starts even when a touch operation is performed that not a correction, and therefore even if no correction is made an operator touches the store button 171 to acknowledge that there is no problem with the displayed content.

Further, the flow shown in FIG. 35 indicates an example of representative disease score correction processing, but the present invention is not limited thereto. For example, steps S8001 to S8008 need not be performed in this order, and may be performed in a different order.

The flow shown in FIG. 35 is not limited to representative disease score correction and may be used in correction of disease scores for frames other than a representative disease frame.

The above is a description of correction of disease data for one diagnostic site after measuring is complete, but the correction may be performed after completion of measurement for one diagnostic site and may be performed after completion of measurement for all diagnostic sites. When correction is performed after completion of measurement for all diagnostic sites, diagnostic sites to be correction can be selected by touching the next button 164 and the return button 165 of the diagnostic site display portion 160. When the next button 164 is touched, the diagnostic image of the next diagnostic site is displayed, and when the return button 165 is touched, the diagnostic image of the previous diagnostic site is displayed.

Further, when correction is performed after measurement of one diagnostic site is complete, and correction is completed, and measurement of the next diagnostic site is to be performed, touching the next button 164 causes a display screen to be displayed as shown in FIG. 24, and measurement of the next diagnostic site can be performed.

Figure 36:
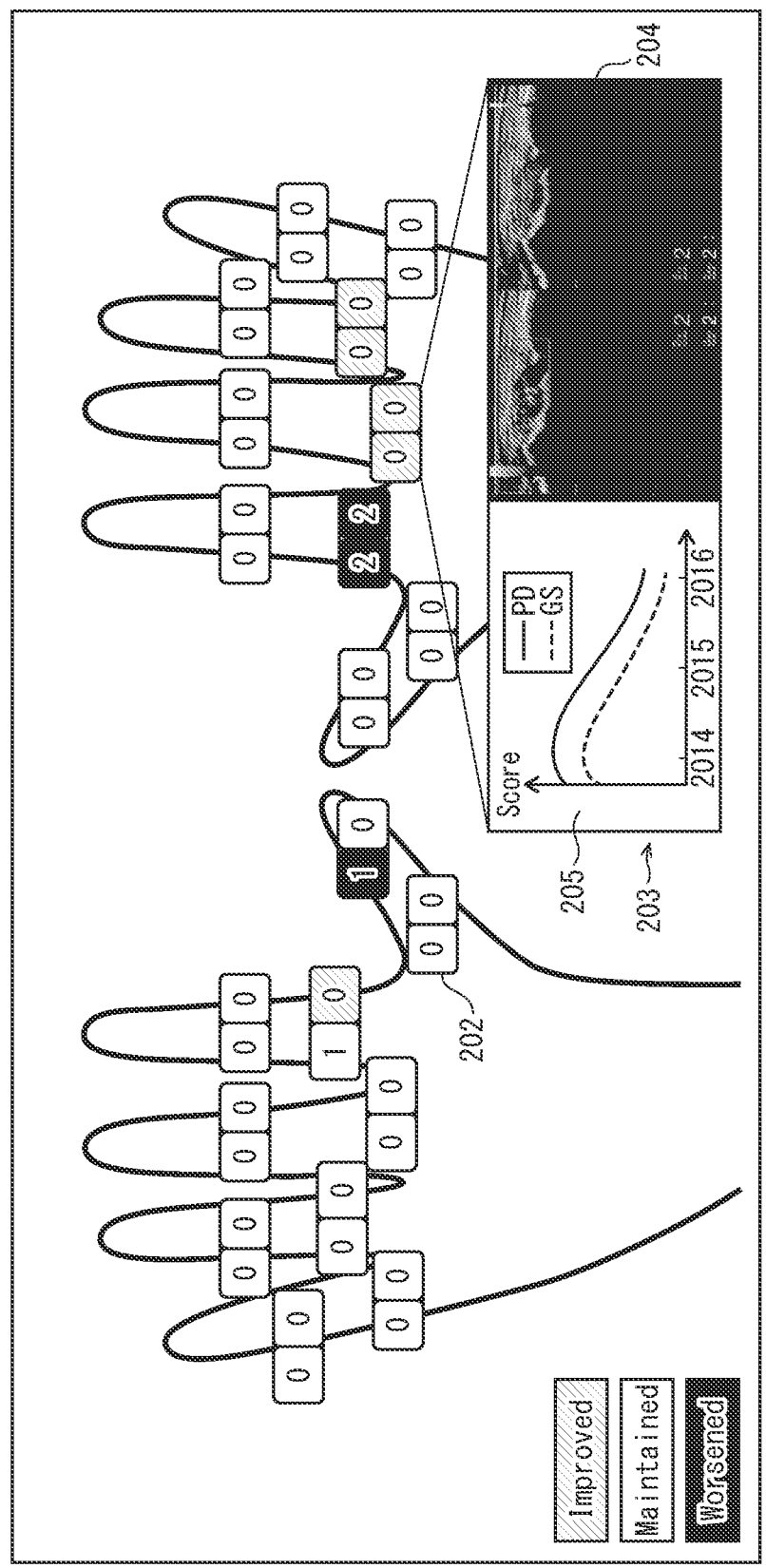
FIG. 36 shows an example of an overall diagnostic image.

(4) Display Screen of Diagnostic Results After Measurement is Complete for All Diagnostic Sites FIG. 36 shows an example of a display screen after measurement is complete for all diagnostic sites. When evaluation is complete for all ultrasound images for all diagnostic sites (finger joints according to the present embodiment), an overall diagnostic image showing an overview of all examinations is displayed.

A diagnostic site icon 202 is displayed in all diagnostic site positions in the overall diagnostic image. A number indicating a representative swelling score of a corresponding diagnostic site is displayed on the left side of the diagnostic site icon 202, and a number indicating a representative inflammation score is displayed on the right side of the diagnostic site icon 202. Further, whether the representative disease score (representative swelling score, representative inflammation score) of each diagnostic site has improved, been maintained, or worsened from the previous representative disease score is represented by at least one of a background color, lightness, saturation, and pattern of the diagnostic site icon 202. According to the embodiment shown in FIG. 36, improvement is represented by hatching, maintained condition is represented by no pattern (solid white), and worsening is represented by no pattern (solid black). Alternatively, for example, blue or light red (low saturation) may represent improvement, white or a midrange saturation of red a maintained condition, and red or dark red (high saturation) worsening. Further, as long as it can be clearly discriminated, at least one of color, lightness, saturation, and pattern of the numbers may be changed instead of the background.

When the diagnostic site icon 202 indicating a disease score of a diagnostic site is touched, a pop-up screen 203 is displayed. The pop-up screen 203 includes an ultrasound image 204 of a representative disease frame of the diagnostic site and a graph 205 representing changes over time of disease score of the diagnostic site.

Note that the progress determiner 1017 (see FIG. 2) determines whether a representative disease score (representative swelling score, representative inflammation score) of each diagnostic site has improved, maintained condition, or worsened in comparison to the previous representative disease score.

<Modifications>

The present invention has been described above based on the ultrasound diagnostic device pertaining to the embodiment. However, the present invention is not limited to the above embodiment, and the following modifications can be implemented.

In order to avoid redundant description, elements that are the same as in the embodiment are assigned the same reference signs and description thereof is omitted.

(Modification 1)

Figure 37:
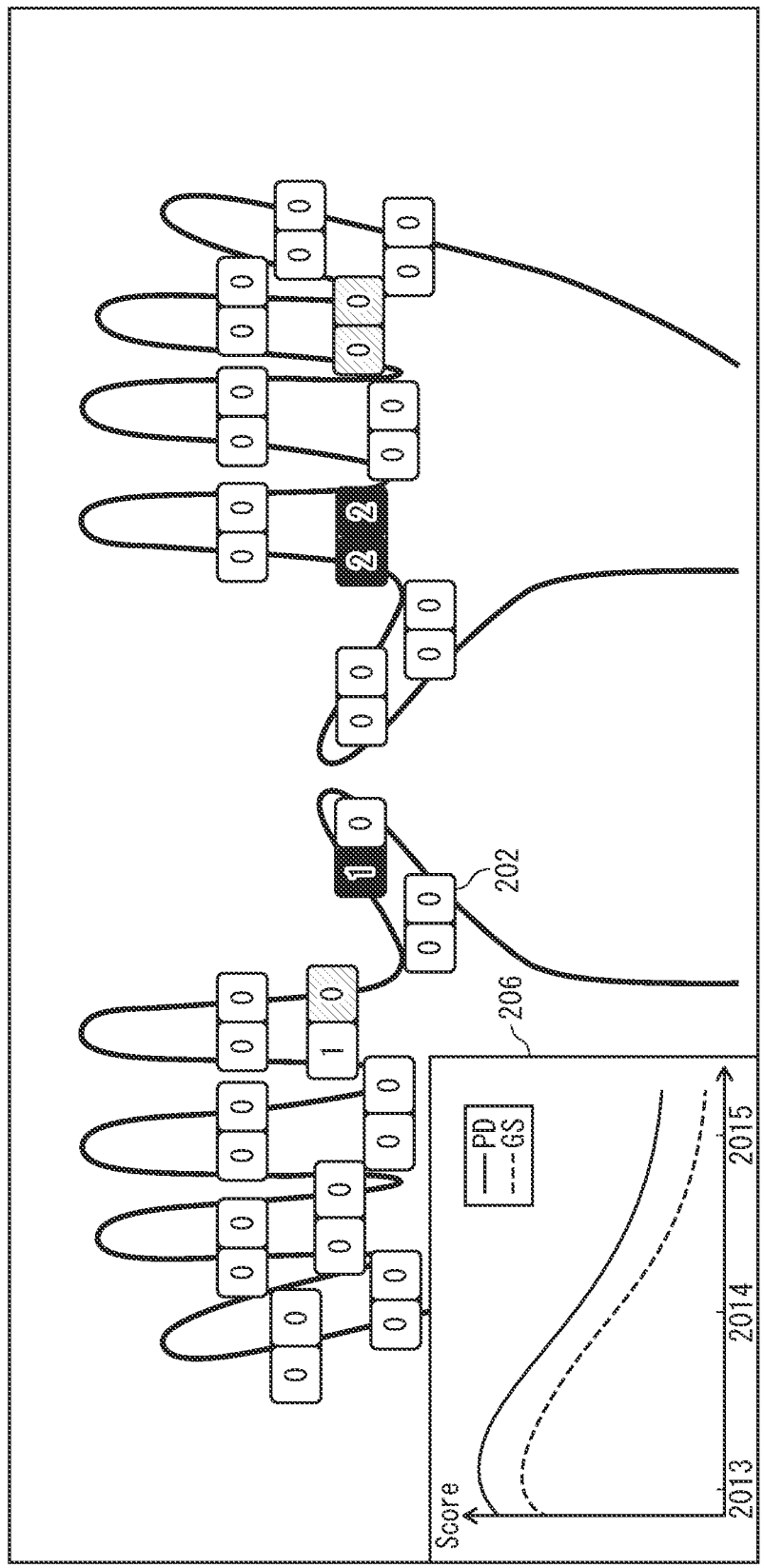
FIG. 37 shows an example of an overall diagnostic image for an ultrasound diagnostic device pertaining to Modification 1.

After completion of measurement of all diagnostic sites, the disease score calculator 2003 (see FIG. 3) may calculate a total disease score that quantitatively represents an overall degree of disease of all diagnostic sites of the subject and, as shown in FIG. 37, in addition to display of disease scores for each diagnostic site, a graph 206 representing change over time of the total disease score may be displayed in the overall diagnostic image. Further, a numerical value of the total disease score may be included in the overall diagnostic image and displayed on the display 1008 (see FIG. 1, FIG. 2).

For the total disease score, a total value, average value, etc., of representative disease scores of all diagnostic sites can be used. Further, the total disease score may be calculated by assigning weight to representative disease scores according to importance of diagnostic sites. In setting importance, a finger joint that has a high frequency of use may be set to a high importance, for example.
(Modification 2)

Figure 38:
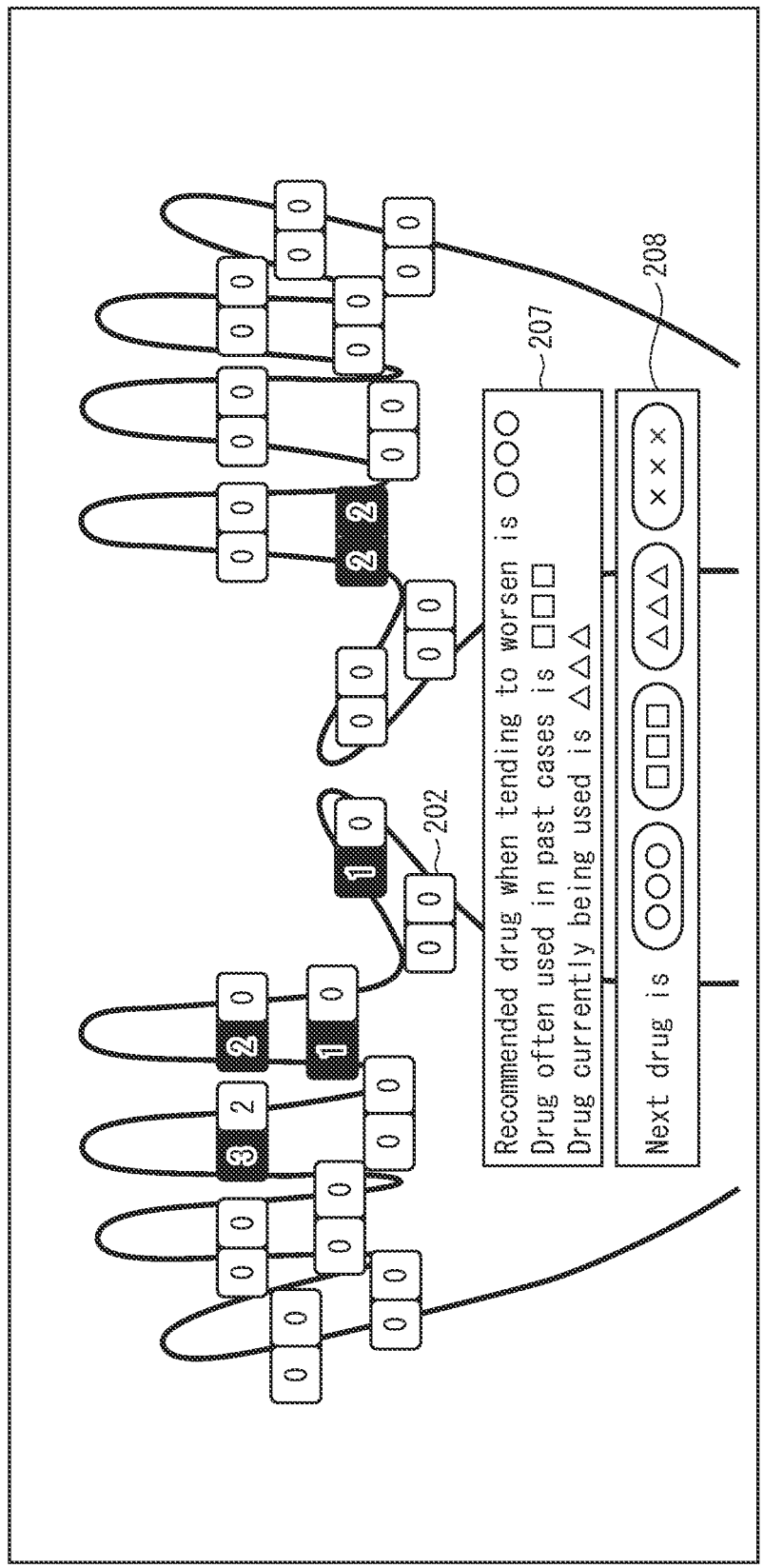
FIG. 38 shows an example of an overall diagnostic image for an ultrasound diagnostic device pertaining to Modification 2.

After measurement of all diagnostic sites is complete, an image portion 207 displaying a recommended drug, a frequently used drug, a currently used drug, etc., and an image portion 208 displaying candidate drugs for prescription may be included in the overall diagnostic image and displayed on the display 1008 (see FIG. 1, FIG. 2), as shown in FIG. 38.

Figure 39:
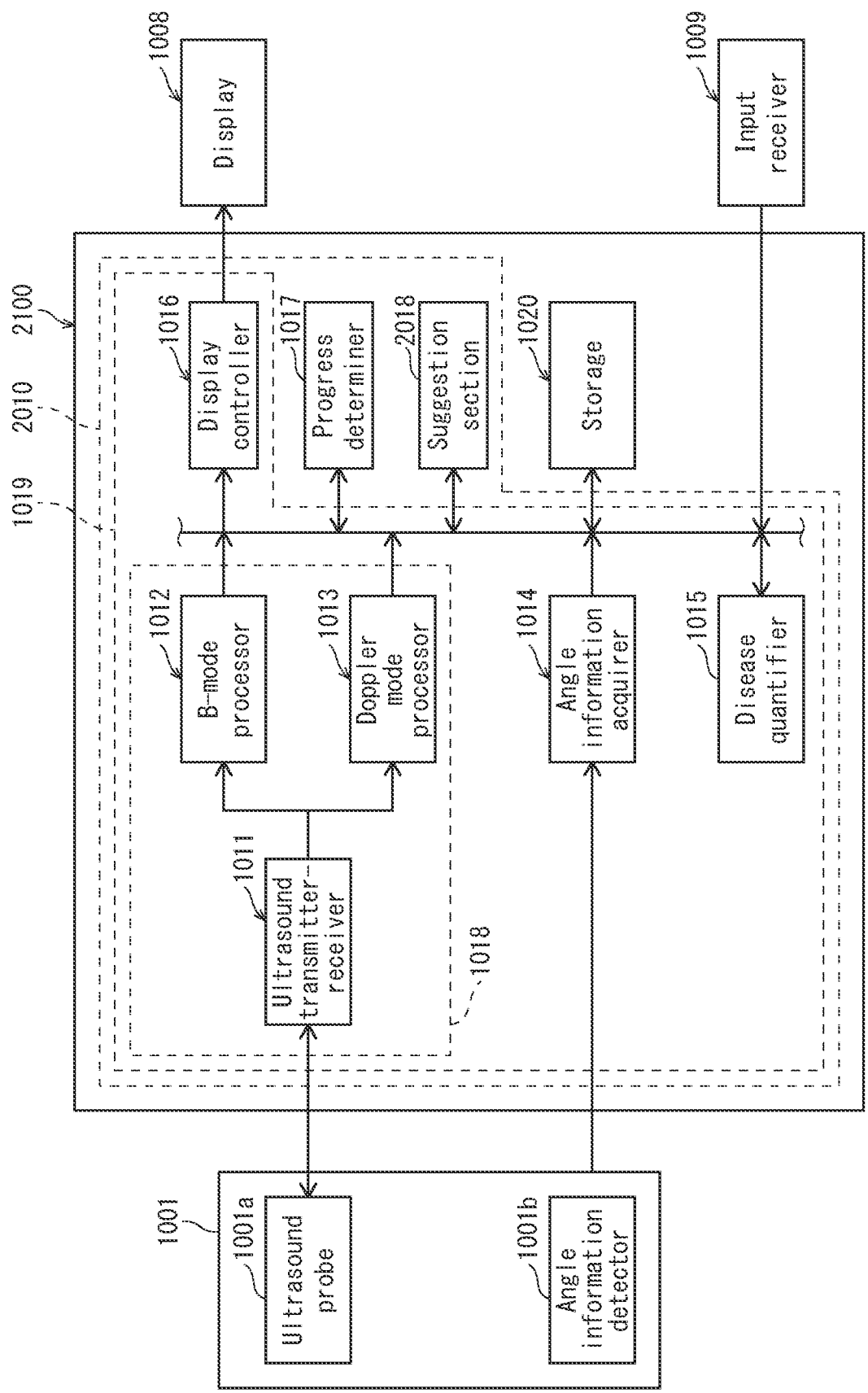
FIG. 39 is a block diagram showing a configuration of an ultrasound diagnostic device pertaining to Modification 2.

FIG. 39 is a block diagram showing a configuration of a controller 2010 of an ultrasound diagnostic device 2100 pertaining to Modification 2. Selection of drugs displayed in the image portion 207 and the image portion 208 is performed by a suggestion section 2018 of the controller 2010. Note that drug information that provides a base for selection of a drug by the suggestion section 2018 is stored in the storage 1020. However, drug information, etc., may be stored in storage media other than the storage 1020 to which the controller 2010 is connected.

Further, a plurality of drug candidates for prescription may be displayed in the image portion 208, and a doctor may touch the touch panel to select a most appropriate drug, the controller 2010 receiving the selection via the touch panel, and the selection of the drug being stored in the storage 1020.

Further, selection of the drug may be transmitted externally to prepare a prescription.
(Modification 3)

According to the embodiment, the subject is a hand and diagnostic sites are finger joints. However, rheumatism does not only occur at finger joints, and the essential configuration of the present invention can be applied to other joints as well. Modification 3 a case in which the subject is a wrist is described as an example. In this case, a plurality of locations of a wrist are diagnostic sites.

Figure 40:
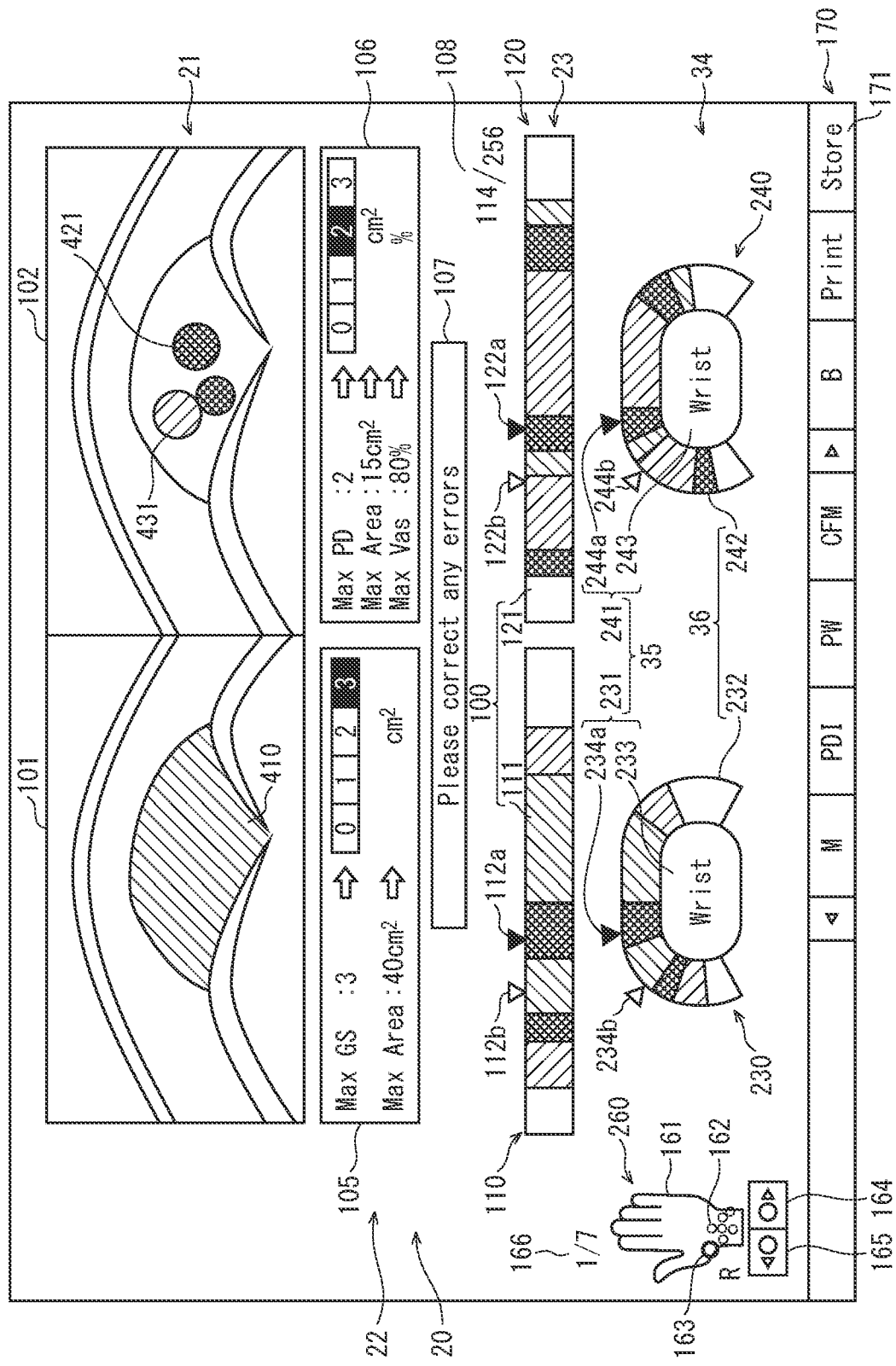
FIG. 40 shows an example of a diagnostic image corresponding to a representative disease frame pertaining to Modification 3.

FIG. 40 shows an example of a diagnostic image pertaining to Modification 3. In the diagnostic image pertaining to Modification 3, differences from a diagnostic image pertaining to the embodiment are an angle disease information display portion 34 (swelling angle disease information display portion 230, inflammation angle disease information display portion 240) and a diagnostic site display portion 260.

A subject cross-section icon 233 of the swelling angle disease information display portion 230 and a subject cross-section icon 243 of the inflammation angle disease information display portion 240 are oval icons indicating a wrist section. The section is perpendicular to the longitudinal direction of the arm and is a virtual plane passing through diagnostic sites of the wrist, i.e., a transverse section. The swelling angle disease information image portion 232 and the inflammation angle disease information image portion 242 are bands around a periphery of the subject cross-section icon 233 of the swelling angle disease information display portion 230 and the subject cross-section icon 243 of the inflammation angle disease information display portion 240, respectively. The subject cross-section icon 233, the subject cross-section icon 243, the swelling angle disease information image portion 232, and the inflammation angle disease information image portion 242 are the same as their equivalents in the embodiment, aside from their shape.

Further, the angle information image portion 35 is composed of the swelling angle information image portion 231 and the inflammation angle information image portion 241. The angle disease information image portion 36 is composed of the swelling angle disease information image portion 232 and the inflammation angle disease information image portion 242.

The diagnostic site display portion 260 is different from the embodiment in that the diagnostic site icons 162 and the measurement diagnostic site icon 163 are positioned on the wrist. Otherwise, the diagnostic site display portion 260 is the same as its equivalent in the embodiment.
(Modification 4)

According to the embodiment described above, in the flow of FIG. 6, the procedure determiner 3004 determines that an image of the object frame is an image obtained by proper procedure when a result of step S1001 is "joint present", a result of step S1002 is "motion-noise absent", and a result of step S1003 is "compression absent", outputs "execute quantification" to the morphometric quantifier 2003A and the inflammation quantifier 2003B, and makes a disease score be calculated. In other cases, a warning message is displayed in the message display portion 107.

However, the procedure determiner 3004 may be configured to determine that an image of an object frame is an image obtained by proper procedure and make a disease score be calculated when a result of step S1001 is "joint present".

Alternatively, the procedure determiner 3004 may determine that an image is obtained by proper procedure and make a disease score be calculated when a result of step S1001 is "joint present" and at least one condition is satisfied of a result of step S1002 being "compression absent" and a result of step S1003 being "motion-noise absent".

Thus, the procedure determiner 3004 more easily determines whether or not an ultrasound image signal of an object frame is an image obtained by proper procedure, and calculation of disease score and selection of an evaluation object frame can be performed more rapidly.
(Modification 5)

Further, disease score is given by Expression 3 and Expression 4 according to the embodiment described above, but as long as a score related to rheumatism is calculated, the present invention is not limited to Expression 3 and Expression 4.
(Modification 6)

Further, according to the embodiment described above, as an example of a disease score quantifying a degree of disease, disease score of rheumatism is selected as an example to describe a method of evaluating disease. However, varieties of disease for which the present invention can be used are not limited to rheumatism, and as long as a degree of disease can be quantified from an ultrasound image, the present invention can be applied to other diseases. For example, the present invention can be used to quantify a degree of cancer by quantifying size of a tumor in an organism and an area ratio of new blood vessels in the tumor from an ultrasound image.
(Modification 7)

According to the ultrasound diagnostic device 1100 pertaining to the embodiment described above, the storage 1020 is included in the ultrasound diagnostic device 1100 as a storage device, but a storage device may be configured to be external to and connectable to the ultrasound diagnostic device 1100 such as semiconductor memory, a hard disk drive, an optical disk drive, a magnetic storage device, and the like.

Further, according to the embodiment described above, the ultrasound probe 1001a and the angle information detector 1001b are integrated with the probe unit 1001 but the present invention is not limited thereto. The ultrasound probe 1001*a* and the angle information detector 1001*b* may be separate devices that are each connected to the ultrasound diagnostic device 1100. For example, an image capture device such as a CCD camera may be used as the angle information detector 1001*b*, the image capture device reading markers on the ultrasound probe 1001*a* to detect angle of the ultrasound probe 1001*a*.

(Modification 8)

According to the embodiment described above, the ultrasound probe is configured with a plurality of piezoelectric elements arranged in one dimension. However, configuration of the ultrasound probe is not limited to this example, and an ultrasound probe configured with a plurality of piezoelectric elements arranged in two dimensions can be used. When using an ultrasound probe that has a two-dimensional arrangement, irradiation position and direction of a transmitted ultrasound beam can be controlled by changing timing of voltage and voltage values applied to each piezoelectric element.

(Modification 9)

Further, the ultrasound probe may include function of a portion of the transmitter-receiver. For example, based on a control signal for generating a transmit electricity signal outputted from the transmitter-receiver, the transmit electricity signal may be generated in the ultrasound probe and the transmit electricity signal converted to ultrasound. In addition, a configuration can be adopted that converts received reflected ultrasound into a received electric signal and generates a receive signal based on the received electric signal in the ultrasound probe.

(Modification 10)

Each processing element included in the ultrasound diagnostic device pertaining to the embodiment can typically be implemented as an LSI, which is an integrated circuit. Each LSI may be an individual chip, or a portion of or all LSI may be included on one chip.

(Modification 11)

For the controller 1010 pertaining to the embodiment described above and the controller 2010, each function block is described as being configured by independent hardware, but the present invention is not limited thereto. For example, functions of function blocks may be implemented by an integrated CPU and software as necessary.

Further, for function blocks of the ultrasound diagnostic device, a part or all functions of the function blocks can typically be implemented as an LSI, which is an integrated circuit. Each LSI may be an individual chip, or a portion of or all LSI may be included on one chip. LSI may refer to an integrated circuit, a system LSI, a super LSI, or an ultra LSI, depending on the level of integration.

Further, methods of circuit integration are not limited to LSI, and implementation may be achieved by a dedicated circuit or general-purpose processor. After LSI manufacture, a field programmable gate array (FPGA) or a reconfigurable processor, in which circuit cell connections and settings in the LSI can be reconfigured, may be used.

Further, if a circuit integration technology is introduced that replaces LSI due to advances in semiconductor technology or another derivative technology, such technology may of course be used to integrate the function blocks.

Further, a portion of or all functions of the ultrasound diagnostic device pertaining to the embodiment may be implemented by executing a program on a processor such as a CPU.

(Modification 12)

Further, the present invention may be a program, and may be a non-transitory computer-readable storage medium on which the program is stored. Further, the program may of course be distributed via a transmission medium such as the Internet. Further, the division of function blocks in the block diagrams is an example, and a plurality of function blocks may be implemented as one function block, one function block may be divided amongst a plurality of function blocks, and part of a function may be implemented by another function block. Further, functions of a plurality of function blocks that have similar functions may be processed in parallel or in time division by a single piece of hardware or software.

(Modification 13)

The order in which steps of each flow of the embodiment are executed is for the purpose of describing the present invention in detail, is not necessarily limited to the order shown in the embodiment, and may be an order other than shown in the embodiment. Further, a portion of the steps may be executed in parallel with other steps.

(Modification 14)

Further, a portion of the functions of the ultrasound diagnostic device pertaining to the embodiment and the modifications may be combined.

Further, the present invention encompasses various modifications that implement changes that a person skilled in the art would conceive of with respect to the embodiment.

<<Summary>>

As described above, the ultrasound diagnostic device pertaining to one aspect of the present invention is an ultrasound diagnostic device for generating a diagnostic image based on a plurality of ultrasound image signal frames acquired from a subject via an ultrasound probe, the ultrasound diagnostic device comprising: an ultrasound signal processing circuit, the ultrasound signal processing circuit comprising: an ultrasound image acquirer that acquires the plurality of ultrasound image signal frames; an angle information acquirer that acquires angle information of an angle of the ultrasound probe relative to the subject when each frame of the plurality of ultrasound image signal frames is being acquired; an evaluation determiner that analyzes the plurality of ultrasound image signal frames, and, when an object image portion that satisfies a predefined condition is included in a frame, determines that the frame is an evaluation object frame; a disease score calculator that calculates a disease score that quantitatively indicates a degree of disease from a signal of the object image portion in the evaluation object frame; and a display controller that generates the diagnostic image and makes the diagnostic image be displayed on a display, wherein the diagnostic image includes an ultrasound image of a frame selected from the plurality of ultrasound image signal frames, a disease activity information indicator that indicates a degree of disease in the selected frame, and an angle information image portion that indicates angle information corresponding to the selected frame.

According to this configuration, when there are a plurality of ultrasound images, an operator can easily search for an appropriate ultrasound image.

Further, according to another example of the ultrasound diagnostic device, the disease activity information indicator indicates the degree of disease for each of the plurality of ultrasound image signal frames in association with angle information corresponding thereto. Here, when the selected frame is an evaluation object frame in the diagnostic image, the disease score may be displayed in the disease activity information indicator indicating the degree of disease in the selected frame.

According to this configuration, an operator can easily recognize an approximate angle of frames indicating a desired degree of disease, and therefore searching for an appropriate diagnostic image can be performed easily.

Further, according to another example, the angle information image portion includes a subject cross-section icon that represents a cross-section of the subject, and an angle indicator that indicates the angle information corresponding to the selected frame according to a position relative to and outside of the subject cross-section icon.

According to this configuration, an operator can intuitively recognize an angle corresponding to a frame, based on position of the angle indictor relative to the subject cross-section icon.

Further, according to another example, the disease activity information indicator includes a border portion around the subject cross-section icon, and the display controller may change at least one of color, lightness, saturation, and pattern in the border portion, based on the disease score at a corresponding angle, thereby indicating the degree of the disease in association with the angle information.

According to this configuration, an operator can easily recognize a relationship between a degree of disease displayed in the border portion and angle of the ultrasound probe indicated by the angle indicator.

Further, according to another example, the disease score calculator performs predefined numerical processing with respect to the disease score for each evaluation object frame, in order to calculate a representative disease score that represents the degree of disease of the object image portion, and selects a representative disease frame corresponding to the representative disease score, and the display controller makes the diagnostic image be displayed that corresponds to the representative disease frame.

According to this configuration, it is possible to calculate a representative disease score based on predefined numerical processing and evaluate a degree of disease among ultrasound images of a plurality of frames taken from multiple directions, and therefore it is possible to reduce examiner dependency in diagnostic results of disease evaluation and degree of disease can be objectively evaluated.

Further, according to another example, the display controller is connected to a storage, the storage stores the disease score and the angle information associated with each ultrasound image signal frame, and the display controller acquires the angle information for the previous representative disease frame from the storage to make a previous angle indicator be displayed in addition to the angle indicator.

According to this configuration, when a representative disease frame is manually selected, an angle of a previous representative disease frame can be considered to make selection easy. Further, comparison with a previous disease score calculated from the ultrasound image acquired at the same angle can easily be performed.

Further, according to another example, the ultrasound signal processing circuit further comprises a progress determiner that acquires the previous representative disease score from the storage, compares the previous representative disease score to the representative disease score, and determines whether the degree of disease has improved, worsened, or remains unchanged, and the display controller acquires a determination result from the progress determiner and makes the determination result be displayed.

According to this configuration, trends in disease progression can easily be understood.

Further, according to another example, the ultrasound signal processing circuit, when the diagnostic image is displayed on the display, upon receiving a correction of the disease score from an operator via the input receiver, stores the disease score that reflects the correction in the storage instead of the disease score prior to the correction.

According to this configuration, when a disease score calculated by the disease score calculator is not correct, an operator can correct it, and therefore a more accurate evaluation of disease activity can be performed.

Further, according to another example, the display controller, upon receiving a selection of an ultrasound image signal frame to be displayed on the display from an operator via the input receiver, makes the diagnostic image corresponding to the selected frame be displayed.

According to this configuration, a diagnostic image of a frame to be checked by an operator can be displayed.

Further, according to another example, the ultrasound signal processing circuit further comprises a suggestion section that suggests a prescription drug based on the determination result, and the display controller makes the prescription drug be displayed.

According to this configuration, drug prescription can easily be performed.

Further, according to another example, the ultrasound signal processing circuit receives a selection by an operator of a suggested prescription drug via the input receiver and stores the selection in the storage.

According to this configuration, a history of prescribed drugs can be created.

Further, according to another example, the plurality of ultrasound image signal frames is acquired continuously, and the diagnostic image includes a bar representing a sequence of the plurality of ultrasound image signal frames and a time sequence indicator that indicates a position along the bar that corresponds to the representative disease frame in the sequence.

According to this configuration, an operator can easily check position of a representative disease frame in a sequence.

Further, according to another example, the display controller makes a previous time sequence indicator corresponding to the previous representative disease frame be displayed in addition to the time sequence indicator corresponding to the representative disease frame.

According to this configuration, when a representative disease frame is manually selected, position of a previous representative disease frame in a sequence can be considered to make selection easy.

Further, according to another example, the disease activity information indicator includes the bar, and represents changes in degree of disease in the bar by changing at least one of color, lightness, saturation, and pattern in the bar based on the disease scores of frames corresponding to the bar.

According to this configuration, when a representative disease frame is manually selected, an operator easily understands where in a sequence a frame is that indicates a desired degree of disease, and therefore searching for an appropriate diagnostic image can easily be performed.

Further, according to another example, the disease activity information indicator indicates the disease score of the selected frame.

According to this configuration, an operator can know the disease score of the selected frame.

Further, according to another example, the ultrasound image acquirer acquires the ultrasound image signal frames for each of a plurality of diagnostic sites, and the display controller makes an overall diagnostic image be displayed, in which the representative disease score of each of the plurality of diagnostic sites is displayed superimposed on a corresponding one of a plurality of diagnostic site icons, each indicating a position of one of the plurality of diagnostic sites of the subject.

According to this configuration, evaluation of disease activity of a plurality of diagnostic sites in a subject can be checked at one time on one screen.

Further, according to another example, the disease score calculator calculates a total disease score quantitatively representing a comprehensive degree of disease of the subject based on the representative disease score of each of the plurality of diagnostic sites, and the display controller makes the total disease score be displayed on the overall diagnostic image.

According to this configuration, degree of disease of the subject as a whole can easily be understood.

Further, according to another example, the display controller acquires the previous total disease score stored in the storage, and makes total disease progression information be displayed on the overall diagnostic image, the total disease progression information indicating change over time of the total disease score.

According to this configuration, it is possible to easily understand whether a disease is worsening, maintaining condition, or improving for the subject as a whole.

Further, according to another example, the predefined numerical processing is processing in which a disease score is selected that matches, or is closest to, at least one value selected from (a) a maximum disease score value indicating a state of greatest disease progression, (b) an average disease score value indicating a state of a mean degree of disease, and (c) a median disease score value indicating a state of a median degree of disease.

According to this configuration, selection criteria based on predefined numerical processing for selecting a most appropriate disease score can be appropriately set based on various conditions such as examination guidelines according to doctors and hospitals, condition of disease, characteristics of subjects, etc.

Further, according to another example, the ultrasound image signal frames include B-mode image signals and Doppler mode image signals.

According to this configuration, it is possible to observe synovial thickening, synovial fluid retention, and bone erosion in a B-mode image and synovial inflammation in a power Doppler image.

Further, according to another example, the disease is rheumatism.

According to this configuration, examination and diagnosis of rheumatism can be performed more effectively by using the ultrasound diagnostic device pertaining to the present invention.

Further, an ultrasound image processing method pertaining to an aspect of the present invention is an ultrasound image processing method for generating a diagnostic image based on a plurality of ultrasound image signal frames acquired from a subject via an ultrasound probe, the ultrasound image processing method comprising: acquiring the plurality of ultrasound image signal frames; acquiring angle information of an angle of the ultrasound probe relative to the subject when each frame of the plurality of ultrasound image signal frames is being acquired; analyzing the plurality of ultrasound image signal frames, and, when an object image portion that satisfies a predefined condition is included in a frame, determining that the frame is an evaluation object frame; calculating a disease score that quantitatively indicates a degree of disease from a signal of the object image portion in the evaluation object frame; and generating the diagnostic image to include an ultrasound image of a frame selected from the plurality of ultrasound image signal frames, a disease activity information indicator that indicates a degree of disease in the selected frame, and an angle information image portion that indicates angle information corresponding to the selected frame, and making the diagnostic image be displayed on a display.

According to this configuration, an ultrasound image processing method is provided that allows an operator to easily search for an ultrasound image frame that indicates a desired degree of disease, based on the disease activity information indicator and the angle information image portion.

Further, according to another example, the disease activity information indicator represents a degree of disease and the angle information for each ultrasound image signal frame.

According to this configuration, an operator can easily recognize an approximate angle of frames indicating a desired degree of disease, and therefore searching for an appropriate ultrasound image frame can be performed easily.

<<Supplement>>

The Embodiment described above is an example of a preferred embodiment of the present invention. The values, shapes, materials, component elements, positions and connections of the component elements, processes, ordering of processes, etc., are only examples and are not intended to limit the scope of the present invention. Further, among the component elements of the embodiment, processes not recited in the independent claims that indicate highest level concepts of the present invention are described as optional elements to improve on the highest level concepts.

Further, in order to aid understanding of the invention, the dimensions of the elements illustrated in the drawings for the embodiment described above may differ from actual dimensions. Further, the present invention is not intended to be limited in scope by the embodiment described above, and can be appropriately modified without departing from the scope of the present invention.

Further, in the ultrasound diagnostic device are members such as circuit elements and lead lines on substrates, but description thereof is omitted, as various configurations are possible based on common knowledge in the technical fields of electrical wiring and circuitry, and such description is not directly relevant to the present invention.

The drawings are schematic diagrams, and are not necessarily exact.

What is claimed is:

1. An ultrasound diagnostic device for generating a diagnostic image based on a plurality of ultrasound image signal frames acquired from a subject via an ultrasound probe, the ultrasound diagnostic device comprising:
    an ultrasound signal processing circuit, the ultrasound signal processing circuit comprising:
    an ultrasound image acquirer that acquires the plurality of ultrasound image signal frames;
    an angle information acquirer that acquires angle information of an angle of the ultrasound probe relative to the subject when each frame of the plurality of ultrasound image signal frames is being acquired;
    an evaluation determiner that analyzes the plurality of ultrasound image signal frames, and, when an object image portion that satisfies a predefined condition is included in a frame, determines that the frame is an evaluation object frame;

a disease score calculator that calculates a disease score that quantitatively indicates a degree of disease from a signal of the object image portion in the evaluation object frame, the disease score comprising: (a) a swelling score, based on image characteristics of a B mode image of an area of interest, and (b) an inflammation score, based on a Doppler image signal indicating blood flow that shows whether or not there is a new blood vessel, wherein the inflammation score is calculated based on an analysis limited to a region that has been identified, using the Doppler image signal, as having a new blood vessel; and a display controller that generates the diagnostic image and makes the diagnostic image be displayed on a display, wherein the diagnostic image includes an ultrasound image of a frame selected from the plurality of ultrasound image signal frames, a disease activity information indicator that indicates a degree of disease in the selected frame, and an angle information image portion that indicates angle information corresponding to the selected frame.

2. The ultrasound diagnostic device of claim 1, wherein the disease activity information indicator indicates the degree of disease for each of the plurality of ultrasound image signal frames in association with angle information corresponding thereto.

3. The ultrasound diagnostic device of claim 1, wherein the angle information image portion includes a subject cross-section icon that represents a cross-section of the subject, and an angle indicator that indicates the angle information corresponding to the selected frame according to a position relative to and outside of the subject cross-section icon.

4. The ultrasound diagnostic device of claim 3, wherein the disease activity information indicator includes a border portion around the subject cross-section icon, and the display controller may change at least one of color, lightness, saturation, and pattern in the border portion, based on the disease score at a corresponding angle, thereby indicating the degree of the disease in association with the angle information.

5. The ultrasound diagnostic device of claim 3, wherein the disease score calculator performs predefined numerical processing with respect to the disease score for each evaluation object frame, in order to calculate a representative disease score that represents the degree of disease of the object image portion, and selects a representative disease frame corresponding to the representative disease score, and the display controller makes the diagnostic image be displayed that corresponds to the representative disease frame.

6. The ultrasound diagnostic device of claim 5, wherein the display controller is connected to a storage, the storage stores the disease score and the angle information associated with each ultrasound image signal frame, and the display controller acquires the angle information for the previous representative disease frame from the storage to make a previous angle indicator be displayed in addition to the angle indicator.

7. The ultrasound diagnostic device of claim 6, wherein the ultrasound signal processing circuit further comprises a progress determiner that acquires the previous representative disease score from the storage, compares the previous representative disease score to the representative disease score, and determines whether the degree of disease has improved, worsened, or remains unchanged, and the display controller acquires a determination result from the progress determiner and makes the determination result be displayed.

8. The ultrasound diagnostic device of claim 6, wherein the ultrasound signal processing circuit, when the diagnostic image is displayed on the display, upon receiving a correction of the disease score from an operator via the input receiver, stores the disease score that reflects the correction in the storage instead of the disease score prior to the correction.

9. The ultrasound diagnostic device of claim 8, wherein the display controller, upon receiving a selection of an ultrasound image signal frame to be displayed on the display from an operator via the input receiver, makes the diagnostic image corresponding to the selected frame be displayed.

10. The ultrasound diagnostic device of claim 7, wherein the ultrasound signal processing circuit further comprises a suggestion section that suggests a prescription drug based on the determination result, and the display controller makes the prescription drug be displayed.

11. The ultrasound diagnostic device of claim 10, wherein the ultrasound signal processing circuit receives a selection by an operator of a suggested prescription drug via the input receiver and stores the selection in the storage.

12. The ultrasound diagnostic device of claim 5, wherein the plurality of ultrasound image signal frames is acquired continuously, and the diagnostic image includes a bar representing a sequence of the plurality of ultrasound image signal frames and a time sequence indicator that indicates a position along the bar that corresponds to the representative disease frame in the sequence.

13. The ultrasound diagnostic device of claim 12, wherein the display controller makes a previous time sequence indicator corresponding to the previous representative disease frame be displayed in addition to the time sequence indicator corresponding to the representative disease frame.

14. The ultrasound diagnostic device of claim 12, wherein the disease activity information indicator includes the bar, and represents changes in degree of disease in the bar by changing at least one of color, lightness, saturation, and pattern in the bar based on the disease scores of frames corresponding to the bar.

15. The ultrasound diagnostic device of claim 1, wherein the disease activity information indicator indicates the disease score of the selected frame.

16. The ultrasound diagnostic device of claim 5, wherein the ultrasound image acquirer acquires the ultrasound image signal frames for each of a plurality of diagnostic sites, and the display controller makes an overall diagnostic image be displayed, in which the representative disease score of each of the plurality of diagnostic sites is displayed superimposed on a corresponding one of a plurality of diagnostic site icons, each indicating a position of one of the plurality of diagnostic sites of the subject.

17. The ultrasound diagnostic device of claim 16, wherein the disease score calculator calculates a total disease score quantitatively representing a comprehensive degree of disease of the subject based on the representative disease score of each of the plurality of diagnostic sites, and the display controller makes the total disease score be displayed on the overall diagnostic image.

18. The ultrasound diagnostic device of claim 17, wherein
the storage stores the total disease score, and
the display controller acquires the previous total disease score stored in the storage, and makes total disease progression information be displayed on the overall diagnostic image, the total disease progression information indicating change over time of the total disease score.

19. The ultrasound diagnostic device of claim 5, wherein
the predefined numerical processing is processing in which a disease score is selected that matches, or is closest to, at least one value selected from (a) a maximum disease score value indicating a state of greatest disease progression, (b) an average disease score value indicating a state of a mean degree of disease, and (c) a median disease score value indicating a state of a median degree of disease.

20. The ultrasound diagnostic device of claim 19, wherein
the ultrasound image signal frames include B-mode image signals and Doppler mode image signals.

21. The ultrasound diagnostic device of claim 1, wherein the disease is rheumatism.

22. An ultrasound image processing method for generating a diagnostic image based on a plurality of ultrasound image signal frames acquired from a subject via an ultrasound probe, the ultrasound image processing method comprising:
acquiring the plurality of ultrasound image signal frames;
acquiring angle information of an angle of the ultrasound probe relative to the subject when each frame of the plurality of ultrasound image signal frames is being acquired;
analyzing the plurality of ultrasound image signal frames, and, when an object image portion that satisfies a predefined condition is included in a frame, determining that the frame is an evaluation object frame;
calculating a disease score that quantitatively indicates a degree of disease from a signal of the object image portion in the evaluation object frame, the disease score comprising: (a) a swelling score, based on image characteristics of a B mode image of an area of interest, and (b) an inflammation score, based on a Doppler image signal indicating blood flow that shows whether or not there is a new blood vessel, wherein the inflammation score is calculated based on an analysis limited to a region that has been identified, using the Doppler image signal, as having a new blood vessel; and
generating the diagnostic image to include an ultrasound image of a frame selected from the plurality of ultrasound image signal frames, a disease activity information indicator that indicates a degree of disease in the selected frame, and an angle information image portion that indicates angle information corresponding to the selected frame, and making the diagnostic image be displayed on a display.

23. The ultrasound image processing method of claim 22, wherein
the disease activity information indicator represents a degree of disease and the angle information for each ultrasound image signal frame.

* * * * *